United States Patent
Hunt et al.

(10) Patent No.: US 11,559,438 B2
(45) Date of Patent: Jan. 24, 2023

(54) INTEGRATED SENSOR ENABLED WOUND MONITORING AND/OR THERAPY DRESSINGS AND SYSTEMS

(71) Applicant: Smith & Nephew PLC, Watford (GB)

(72) Inventors: Allan Kenneth Frazer Grugeon Hunt, Beverly (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 0 days.

(21) Appl. No.: 16/763,950

(22) PCT Filed: Nov. 14, 2018

(86) PCT No.: PCT/EP2018/081198
§ 371 (c)(1),
(2) Date: May 13, 2020

(87) PCT Pub. No.: WO2019/096828
PCT Pub. Date: May 23, 2019

(65) Prior Publication Data
US 2022/0031231 A1 Feb. 3, 2022

Related U.S. Application Data

(60) Provisional application No. 62/586,848, filed on Nov. 15, 2017.

(30) Foreign Application Priority Data

Nov. 15, 2017 (GB) ..................... 1718855
Nov. 15, 2017 (GB) ..................... 1718866
Nov. 15, 2017 (GB) ..................... 1718868

(51) Int. Cl.
*A61M 35/00* (2006.01)
*A61M 1/00* (2006.01)
(Continued)

(52) U.S. Cl.
CPC ...... *A61F 13/00068* (2013.01); *A61B 5/0002* (2013.01); *A61B 5/445* (2013.01);
(Continued)

(58) Field of Classification Search
CPC ........ A61M 35/00; A61M 1/00; A61M 1/962; A61M 1/0058; A61M 2205/3306;
(Continued)

(56) References Cited

U.S. PATENT DOCUMENTS 3,896,802 A 7/1975 Williams
4,334,530 A 6/1982 Hassell
(Continued)

FOREIGN PATENT DOCUMENTS

CN 105232229 A 1/2016
CN 105395184 A 3/2016
(Continued)

OTHER PUBLICATIONS

American Heritage® Dictionary of the English Language, Fifth Edition. Copyright © 2016 (Year: 2016).*
(Continued)

*Primary Examiner* — Tatyana Zalukaeva
*Assistant Examiner* — Ilya Y Treyger
(74) *Attorney, Agent, or Firm* — Knobbe, Martens Olson & Bear, LLP

(57) ABSTRACT

A wound monitoring and/or therapy system can include a substantially stretchable substrate supporting a plurality of electronic components, including sensors, and a plurality of electronic connections that connect at least some of the electronic components. The electronic components can also include a circuit board supporting at least one controller configured to control at least some of the sensors, the circuit board configured to operate without failure when the substrate is flexed as a result of strain. A calibration track can
(Continued)

be positioned on the substrate and connected to a monitoring circuit configured to measure a change in resistance of the calibration track indicative of resistance change of at least some of the plurality of electronic connections. The system can include a controller with a circuit board supporting a plurality of electrical components and an antenna configured to communicate with the substrate, the antenna at least partially enclosing the circuit board.

17 Claims, 30 Drawing Sheets

(51) Int. Cl.
*A61F 13/00* (2006.01)
*A61F 13/02* (2006.01)
*A61B 5/00* (2006.01)

(52) U.S. Cl.
CPC ........ *A61B 5/6802* (2013.01); *A61F 13/0216* (2013.01); *A61F 13/0276* (2013.01); *A61M 1/73* (2021.05); *A61M 1/915* (2021.05); *A61M 1/92* (2021.05); *A61M 1/962* (2021.05); *A61M 1/985* (2021.05); *A61M 2205/3306* (2013.01)

(58) Field of Classification Search
CPC ...... A61F 13/00; A61F 13/02; A61F 13/0216; A61F 13/0276; A61B 5/445; A61B 5/0002; A61B 5/6802
See application file for complete search history.

(56) References Cited

U.S. PATENT DOCUMENTS

| | | |
|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,088,591 B2 | 8/2006 | Kishimoto et al. |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,974,428 B2 | 3/2015 | Freedman et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,380,696 B2 | 6/2016 | Watanabe |
| 9,386,947 B2 | 7/2016 | Johnson |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |

(56) References Cited

U.S. PATENT DOCUMENTS

| | | |
|---|---|---|
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0047517 A1 | 2/2010 | Zama et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh et al. |
| 2016/0022223 A1 | 1/2016 | Grundfest et al. |
| 2016/0029900 A1 | 2/2016 | Laplante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano' et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |

(56) References Cited

U.S. PATENT DOCUMENTS

| | | |
|---|---|---|
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0078499 A1 | 3/2020 | Gadde et al. |
| 2020/0100711 A1 | 4/2020 | Choudhury et al. |
| 2020/0147407 A1 | 5/2020 | Efremkin |
| 2020/0330258 A1 | 10/2020 | Hansen et al. |
| 2022/0079814 A1 | 3/2022 | Chen et al. |

FOREIGN PATENT DOCUMENTS

| | | |
|---|---|---|
| CN | 106102322 A | 11/2016 |
| CN | 109350362 A | 2/2019 |
| DE | 102012211015 A1 | 1/2014 |
| DE | 102013013013 A1 | 2/2015 |
| EP | 2454990 A2 | 5/2012 |
| EP | 2565630 A1 | 3/2013 |
| EP | 3231478 A1 | 10/2017 |
| EP | 3409190 A1 | 12/2018 |
| EP | 3499510 A1 | 6/2019 |
| GB | 2316171 A | 2/1998 |
| GB | 2563602 A | 12/2018 |
| JP | H065485 A | 1/1994 |
| JP | 2009225863 A | 10/2009 |
| KR | 20120119523 A | 10/2012 |
| KR | 101224629 B1 | 1/2013 |
| KR | 20140024743 A | 3/2014 |
| KR | 20140058041 A | 5/2014 |
| KR | 20160071044 A | 6/2016 |
| KR | 20190105898 A | 9/2019 |
| NL | 1027236 C2 | 4/2006 |
| WO | WO-0021433 A1 | 4/2000 |
| WO | WO-0043046 A2 | 7/2000 |
| WO | WO-03067229 A1 | 8/2003 |
| WO | WO-2004006326 A1 | 1/2004 |
| WO | WO-2006041997 A2 | 4/2006 |
| WO | WO-2007030379 A2 | 3/2007 |
| WO | WO-2008006150 A1 | 1/2008 |
| WO | WO-2008010604 A1 | 1/2008 |
| WO | WO-2008030960 A2 | 3/2008 |
| WO | WO-2009052607 A1 | 4/2009 |
| WO | WO-2009111641 A1 | 9/2009 |
| WO | WO-2009120951 A2 | 10/2009 |
| WO | WO-2009141777 A1 | 11/2009 |
| WO | WO-2010020919 A1 | 2/2010 |
| WO | WO-2010105053 A2 | 9/2010 |
| WO | WO-2011082420 A1 | 7/2011 |
| WO | WO-2011113070 A1 | 9/2011 |
| WO | WO-2011123848 A1 | 10/2011 |
| WO | WO-2012141999 A1 | 10/2012 |
| WO | WO-2013026999 A1 | 2/2013 |
| WO | WO-2013044226 A2 | 3/2013 |
| WO | WO-2014036577 A1 | 3/2014 |
| WO | WO-2014172248 A1 | 10/2014 |
| WO | WO-2015112095 A1 | 7/2015 |
| WO | WO-2015168720 A1 | 11/2015 |
| WO | WO-2016025438 A1 | 2/2016 |
| WO | WO-2016030752 A1 | 3/2016 |
| WO | WO-2016058032 A1 | 4/2016 |
| WO | WO-2016073777 A1 | 5/2016 |
| WO | WO-2016100218 A1 | 6/2016 |
| WO | WO-2016109744 A1 | 7/2016 |
| WO | WO-2016110564 A1 | 7/2016 |
| WO | WO-2016187136 A1 | 11/2016 |
| WO | WO-2016205872 A1 | 12/2016 |
| WO | WO-2016205881 A1 | 12/2016 |
| WO | WO-2017021006 A1 | 2/2017 |
| WO | WO-2017021965 A2 | 2/2017 |
| WO | WO-2017033058 A1 | 3/2017 |
| WO | WO-2017037479 A1 | 3/2017 |
| WO | WO-2017041014 A1 | 3/2017 |
| WO | WO-2017041385 A1 | 3/2017 |
| WO | WO-2017041386 A1 | 3/2017 |
| WO | WO-2017041387 A1 | 3/2017 |
| WO | WO-2017119996 A1 | 7/2017 |
| WO | WO-2017205728 A1 | 11/2017 |
| WO | WO-2017214188 A1 | 12/2017 |
| WO | WO-2018035612 A1 | 3/2018 |
| WO | WO-2018060417 A1 | 4/2018 |
| WO | WO-2018064569 A1 | 4/2018 |
| WO | WO-2018115461 A1 | 6/2018 |
| WO | WO-2018144938 A1 | 8/2018 |
| WO | WO-2018144941 A1 | 8/2018 |
| WO | WO-2018144943 A1 | 8/2018 |
| WO | WO-2018144946 A1 | 8/2018 |
| WO | WO-2018162728 A2 | 9/2018 |
| WO | WO-2018162732 A1 | 9/2018 |
| WO | WO-2018162735 A1 | 9/2018 |
| WO | WO-2018162736 A1 | 9/2018 |
| WO | WO-2018185138 A1 | 10/2018 |
| WO | WO-2018189265 A1 | 10/2018 |
| WO | WO-2018209090 A1 | 11/2018 |
| WO | WO-2018210692 A1 | 11/2018 |
| WO | WO-2018211458 A1 | 11/2018 |
| WO | WO-2018234443 A1 | 12/2018 |
| WO | WO-2019020550 A2 | 1/2019 |
| WO | WO-2019020551 A1 | 1/2019 |
| WO | WO-2019020666 A1 | 1/2019 |
| WO | WO-2019030384 A2 | 2/2019 |
| WO | WO-2019048624 A1 | 3/2019 |
| WO | WO-2019048626 A1 | 3/2019 |
| WO | WO-2019048638 A1 | 3/2019 |
| WO | WO-2019063481 A1 | 4/2019 |
| WO | WO-2019063488 A2 | 4/2019 |
| WO | WO-2019067264 A1 | 4/2019 |
| WO | WO-2019072531 A1 | 4/2019 |
| WO | WO-2019076967 A2 | 4/2019 |
| WO | WO-2019096828 A1 | 5/2019 |
| WO | WO-2019140441 A2 | 7/2019 |
| WO | WO-2019140444 A1 | 7/2019 |
| WO | WO-2019140448 A1 | 7/2019 |
| WO | WO-2019140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |

(56) References Cited

FOREIGN PATENT DOCUMENTS

| WO | WO-2019238196 A1 | 12/2019 |
|---|---|---|
| WO | WO-2019238197 A1 | 12/2019 |
| WO | WO-2019238198 A1 | 12/2019 |
| WO | WO-2020043806 A1 | 3/2020 |

OTHER PUBLICATIONS

"AN11276 NTAG Antenna Design Guide," NXP Semiconductors, released on Apr. 27, 2016, 47 pages.

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M.F., et al., "Low Cost Inkjet Printed Smart Bandage for Wireless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17, No. 3, May 1, 2013, pp. 591-599.

Iannetta Jr. R.A., et al., "Successful Case Histories of Polymer Based Circuitry on Flexible Film Substrates," Electro/94 International Conference Proceedings Combined Volumes. IEEE, XP010149465, May 10-12, 1994, pp. 885-889.

International Preliminary Report on Patentability for Application No. PCT/EP2018/081198, dated May 28, 2020, 9 pages.

International Search Report and Written Opinion for Application No. PCT/EP2018/081198, dated Feb. 28, 2019, 17 pages.

Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for μTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mostafalu P., et al., "Wireless Flexible Smart Bandage for Continuous Monitoring of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Conformal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

Mehmood N., et al., "Applications of Modern Sensors and Wireless Technology in Effective Wound Management: Modern Sensors and Wireless Technology," Journal of Biomedical Materials Research Part B, vol. 102, May 1, 2014, XP055739544, pp. 885-895.

\* cited by examiner

320

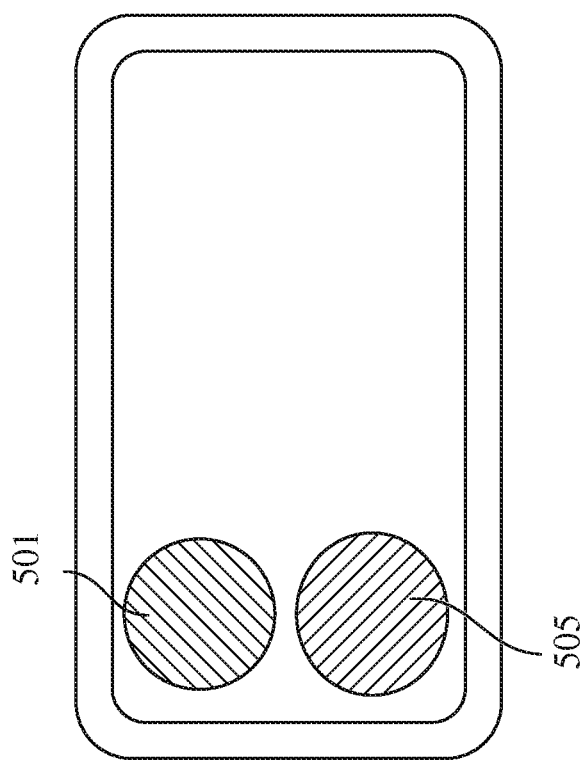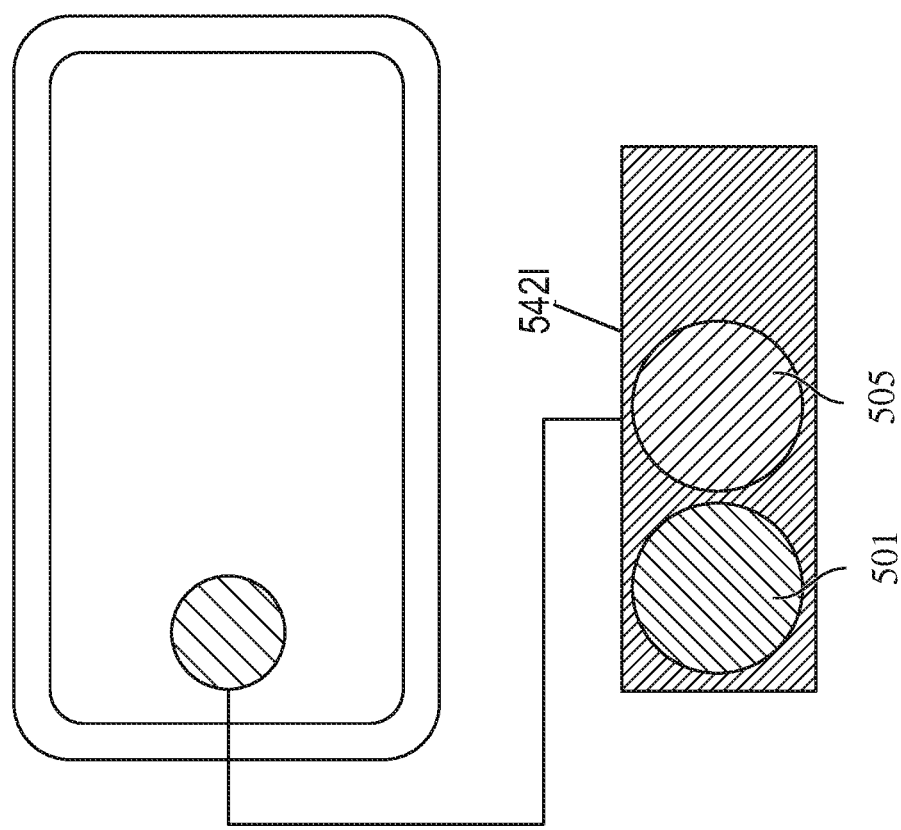

INTEGRATED SENSOR ENABLED WOUND MONITORING AND/OR THERAPY DRESSINGS AND SYSTEMS

INCORPORATION BY REFERENCE TO ANY PRIORITY APPLICATIONS

This Application is a U.S. national stage application of International Patent Application No. PCT/EP2018/081198, filed Nov. 14, 2018, which claims priority to U.S. Provisional Application No. 62/586,848, filed on Nov. 15, 2017, entitled "INTEGRATED SENSOR ENABLED WOUND THERAPY DRESSINGS AND SYSTEMS." This Application also claims priority to U.K. Patent Application No. 1718866.5, filed on Nov. 15, 2017, entitled "INTEGRATED SENSOR ENABLED WOUND THERAPY DRESSINGS AND SYSTEM." This Application also claims priority to U.K. Patent Application No. 1718855.8, filed on Nov. 15, 2017, entitled "SENSOR ENABLED WOUND THERAPY DRESSINGS SYSTEMS AND MONITORING ELECTRICAL IMPEDANCE CHANGES." This Application also claims priority to U.K. Patent Application No. 1718868.1, filed on Nov. 15, 2017, entitled "ANTENNAS FOR SENSOR ENABLED WOUND THERAPY DRESSINGS AND SYSTEMS." The disclosures of these prior applications are hereby incorporated by reference in their entireties and should be considered a part of this specification.

TECHNICAL FIELD

Embodiments of the present disclosure relate to apparatuses, systems, and methods for the monitoring and/or treatment of tissues via sensor-enabled monitoring alone or in combination with various therapy regimes.

DESCRIPTION OF THE RELATED ART

Nearly all areas of medicine may benefit from improved information regarding the state of the tissue, organ, or system to be treated, particularly if such information is gathered in real-time during treatment. Many types of treatments are still routinely performed without the use of sensor data collection; instead, such treatments rely upon visual inspection by a caregiver or other limited means rather than quantitative sensor data. For example, in the case of wound treatment via dressings and/or negative pressure wound therapy, data collection is generally limited to visual inspection by a caregiver and often the underlying wounded tissue may be obscured by bandages or other visual impediments. Even intact, unwounded skin may have underlying damage that is not visible to the naked eye, such as a compromised vascular or deeper tissue damage that may lead to an ulcer. Similar to wound treatment, during orthopedic treatments requiring the immobilization of a limb with a cast or other encasement, only limited information is gathered on the underlying tissue. In instances of internal tissue repair, such as a bone plate, continued direct sensor-driven data collection is not performed. Further, braces and/or sleeves used to support musculoskeletal function do not monitor the functions of the underlying muscles or the movement of the limbs. Outside of direct treatments, common hospital room items such as beds and blankets could be improved by adding capability to monitor patient parameters.

Therefore, there is a need for improved sensor monitoring, particularly through the use of sensor-enabled substrates which can be incorporated into existing monitoring and/or treatment regimes.

SUMMARY

In some cases, a wound monitoring and/or therapy system includes a wound dressing configured to be positioned over a wound, the wound dressing including a substantially stretchable substrate supporting a plurality of electronic components and a plurality of electronic connections that connect at least some of the plurality of the electronic components. The plurality of electronic components can include a plurality of sensors configured to obtain measurement data of at least one of the wound or periwound. The plurality of electronic components can include at least one controller positioned on a circuit board, the at least one controller configured to control at least some of the plurality of sensors, the circuit board formed from reinforced material and configured to operate without failure when the circuit board is flexed as a result of strain on the wound dressing.

The system of any of preceding paragraphs or any of the systems described herein can include one or more of the following features. The material of the circuit board may have been reinforced by being subjected to compression in order to increase resiliency of the material of the circuit board to flexing. The material of the circuit board may have been reinforced by being pre-strained. The wound dressing can include a coating covering at least some of the plurality of electronic components and at least some of the plurality of electronic connections, and the material of the circuit board may have been reinforced by the coating compressing the material of the circuit board when being applied to the wound dressing. The coating can be hydrophobic and/or bio compatible. The wound dressing can further include an antenna configured to communicate measurement data to a remote computing device.

The system of any of preceding paragraphs or any of the systems described herein can include one or more of the following features. The system can include a power source positioned on the substrate, the power source configured to power the plurality of electronic components. The power source may not be enclosed in a separate casing or enclosure. The substrate can include first and second portions, and the power source can include an anode supported by the first portion of the substrate and a cathode supported by the second portion of the substrate, and the power source can further include an electrolyte layer positioned between the anode and cathode. The anode can be positioned on a first electronic connection of the plurality of electronic connections and the cathode can be positioned on a second electronic connection of the plurality of electronic connections.

The system of any of preceding paragraphs or any of the systems described herein can include one or more of the following features. The at least one controller is configured to be activated by one or more of: flexing the wound dressing, activating an activation switch, bursting a bubble of conductive material, charging a transistor, initiating a magnetic trigger, or triggering a piezoelectric element. The system may not be configured to be physically connected to an external controller that controls any of the plurality of sensors or receives any of the measurement data. The substrate can include a plurality of perforations configured to allow fluid to pass through the substrate. The system can include a negative pressure source configured to be fluidically connected to the wound dressing, the negative pressure source configured to supply negative pressure to the wound.

In some cases, a wound monitoring and/or therapy system includes a wound dressing configured to be positioned over a wound, the wound dressing including a substantially stretchable substrate supporting a plurality of electronic components and a plurality of electronic connections that connect at least some of the plurality of the electronic components, the plurality of electronic components including a plurality of sensors configured to obtain measurement data of at least one of the wound or periwound. The system can include a control module configured to be connected to the wound dressing, the control module including at least one controller configured to obtain the measurement data from the plurality of sensors and a power source configured to provide power to the at least one controller and the plurality of sensors, the at least one controller and power source enclosed in an enclosure.

The system of any of preceding paragraphs or any of the systems described herein can include one or more of the following features. The enclosure can include a first portion supporting the at least one controller and power source and a second portion configured to be attached to at least one pin positioned on the first portion. The enclosure can be configured to substantially shield the at least one controller from at least one of electromagnetic interference (EMI) or electrostatic discharge (ESD).

In some cases, a method of manufacturing a wound dressing configured to be positioned over a wound and be used in a wound monitoring and/or therapy system includes pre-straining a circuit board including a controller by at least one of: stretching at least a portion of a substantially flexible substrate of the wound dressing, positioning the circuit board on at least the portion of the substrate, and subsequently relaxing at least the portion of the substrate or compressing the circuit board and subsequently positioning the circuit board on the substrate. The substrate can support a plurality of sensors configured to obtain measurement data of at least one of the wound or periwound and a plurality of electronic connections that connect at least some of the plurality of the sensors and the controller, and wherein the controller is configured to control at least some of the plurality of sensors. Pre-straining the circuit board can increase resiliency of the circuit board to flexing and can cause the circuit board to operate without failure when the circuit board is flexed as a result of strain being applied to the substrate.

The method of any of preceding paragraphs or any of the methods described herein can include one or more of the following features. Pre-straining the circuit board can include positioning the circuit board on the substrate, covering at least a portion of the substrate including the circuit board with coating, and causing the coating to shrink by curing the coating, thereby applying compression to at least the portion of the substrate including the circuit board. Coating can be at least one of biocompatible or hydrophobic.

In some cases, a wound monitoring and/or therapy apparatus includes a wound dressing configured to be positioned in contact with a wound, the wound dressing including a substantially stretchable substrate supporting a plurality of sensors configured to obtain measurements of at least one of the wound or periwound and a plurality of conductive tracks electrically connecting the plurality of sensors and at least one calibration track positioned on the substrate, the at least one calibration track electrically connected to a monitoring circuit configured to measure a first change in resistance of the at least one calibration track, the first change in resistance of the at least one calibration track corresponding to a change in resistance of at least some of the plurality of conductive tracks.

The apparatus of any of preceding paragraphs or any of the systems and/or apparatuses described herein can include one or more of the following features. The at least one calibration track can surround at least a portion of a perimeter of the substrate. The at least one calibration track can include a plurality of calibration tracks, and each of the calibration tracks can be associated with a particular sensor of the plurality of sensors. The monitoring circuit is can be configured to measure a baseline resistance of the at least one calibration track when the substrate is not stretched and determine the first change in resistance of the at least one calibration track based on a difference between the baseline resistance and resistance of the at least one calibration track due to stretching and/or tearing of the substrate. The monitoring circuit can be further configured to adjust a measurement obtained by a sensor of a plurality of sensors based on the first change in resistance.

The apparatus of any of preceding paragraphs or any of the systems and/or apparatuses described herein can include one or more of the following features. The apparatus can include a controller configured to, in response to a determination that the first change in resistance exceeds a threshold, control at least some of the plurality of sensors to defer the one or more measurements. The controller can be further configured to control the at least some of the plurality of sensors to obtain one or more measurements in response to a determination that a second change in resistance is below the threshold, the second change in resistance measured subsequent to the measurement of the first change in resistance. At least some of the plurality of sensors can include one or more sensors configured to measure impedance. The at least one calibration track can include a plurality of calibration tracks configured to measure a plurality of first changes in resistance associated with a plurality of different regions of the substrate. The at least one calibration track can be configured to be connected to a different power supply than the plurality of sensors.

In some cases, a method of operating a wound monitoring and/or therapy apparatus including a wound dressing including a substantially stretchable substrate supporting a plurality of sensors configured to obtain measurements of at least one of a wound or periwound and a plurality of conductive tracks electrically connecting the plurality of sensors can include, with a monitoring circuit of the wound monitoring apparatus, measuring a first change in resistance of at least one calibration track positioned on the substrate, the first change in resistance of the at least one calibration track corresponding to a change in resistance of at least some of the plurality of conductive tracks.

The method of any of preceding paragraphs or any of the methods described herein can include one or more of the following features. The at least one calibration track can surround at least a portion of a perimeter of the substrate. The at least one calibration track can include a plurality of calibration tracks, and wherein each of the calibration tracks is associated with a particular sensor of the plurality of sensors or wherein the plurality of calibration tracks is associated with measuring changes in resistance in plurality of different regions of the substrate. The method can include measuring a baseline resistance of the at least one calibration track when an intact substrate is not stretched and determining the first change in resistance of the at least one calibration track based on a difference between the baseline resistance and resistance of the at least one calibration track due to stretching and/or tearing of the substrate.

The method of any of preceding paragraphs or any of the methods described herein can include one or more of the following features. The method can further include adjusting a measurement obtained by a sensor of the plurality of sensors based on the first change in resistance. The method can further include, by a controller of the wound monitoring apparatus, receiving the first change in resistance from the monitoring circuit, determining that the first change in resistance exceeds a threshold, and controlling at least some of the plurality of sensors to defer obtaining one or more measurements. The method can further include, by the controller, determining that a second change in resistance measured subsequent to the measurement of the first change in resistance is below the threshold and controlling the at least some of the plurality of sensors to obtain one or more measurements. At least some of the plurality of sensors can include one or more sensors configured to measure impedance.

In some cases, a wound monitoring and/or therapy apparatus includes a wound dressing configured to be positioned in contact with a wound, the wound dressing including a substantially stretchable substrate supporting a plurality of sensors configured to obtain measurements of the wound and a controller configured to be electrically connected to the wound dressing and further configured to receive the measurements obtained by the plurality of sensors of the wound dressing, the controller including a circuit board supporting a plurality of electrical components and an antenna configured to communicate with at least one of the wound dressing or a remote computing device, wherein the antenna at least partially encloses the circuit board supporting the plurality of electrical components.

The apparatus of any of preceding paragraphs or any of the systems and/or apparatuses described herein can include one or more of the following features. The antenna can enclose an entire region of the circuit board supporting the plurality of electrical components except a portion of the region that includes a plurality of connections configured to be electrically connected to the wound dressing. The antenna can enclose an entire region of the circuit board supporting the plurality of electrical components.

In some cases, a wound monitoring and/or therapy apparatus includes a wound dressing configured to be positioned in contact with a wound, the wound dressing including a substantially stretchable substrate supporting a plurality of sensors configured to obtain measurements of the wound and a controller configured to be electrically connected to the wound dressing and further configured to receive the measurements obtained by the plurality of sensors of the wound dressing, the controller including a circuit board supporting a plurality of electrical components and an antenna configured to communicate with at least one of the wound dressing or a remote computing device, wherein the antenna is positioned in a first region of the circuit board different from a second region where the plurality of electrical components are positioned.

The apparatus of any of preceding paragraphs or any of the systems and/or apparatuses described herein can include one or more of the following features. The antenna can substantially enclose the entire first region. The antenna can be C-shaped. The antenna can be L-shaped. The antenna can be rectangular, square or round. The antenna can be positioned remotely from the plurality of electrical components. The substrate can further support a plurality of conductive tracks electrically connecting the plurality of sensors, and wherein at least some of the conductive tracks are configured to be electrically connected to the controller. The antenna can include multiple loops. The antenna can include three loops.

The apparatus of any of preceding paragraphs or any of the systems and/or apparatuses described herein can include one or more of the following features. The circuit board can include multiple layers, and the multiple layers of the multilayered circuit board can support the antenna. The circuit board can include one or more vias configured to interconnect the antenna on each of the multiple layers. The antenna can be configured as a near-field antenna. The antenna can be positioned within a region of the controller defined by an external rectangle of 50×27 mm and an internal rectangle of 35×13 mm, and the internal rectangle can be centered in the external rectangle. The antenna can include 3 mm corner radii. The antenna can be located within a region of the controller defined by an external circle with diameter 41 mm and an internal circle with diameter 24 mm, and the internal circle can be concentric with the external circle. The antenna can include copper wire or etched or printed antenna material.

BRIEF DESCRIPTION OF THE DRAWINGS

Embodiments of the present disclosure will now be described hereinafter, by way of example only, with reference to the accompanying drawings in which:

FIGS. 5A-5J illustrate sensor enabled wound dressings according to some embodiments;

DETAILED DESCRIPTION

Figure 1A:
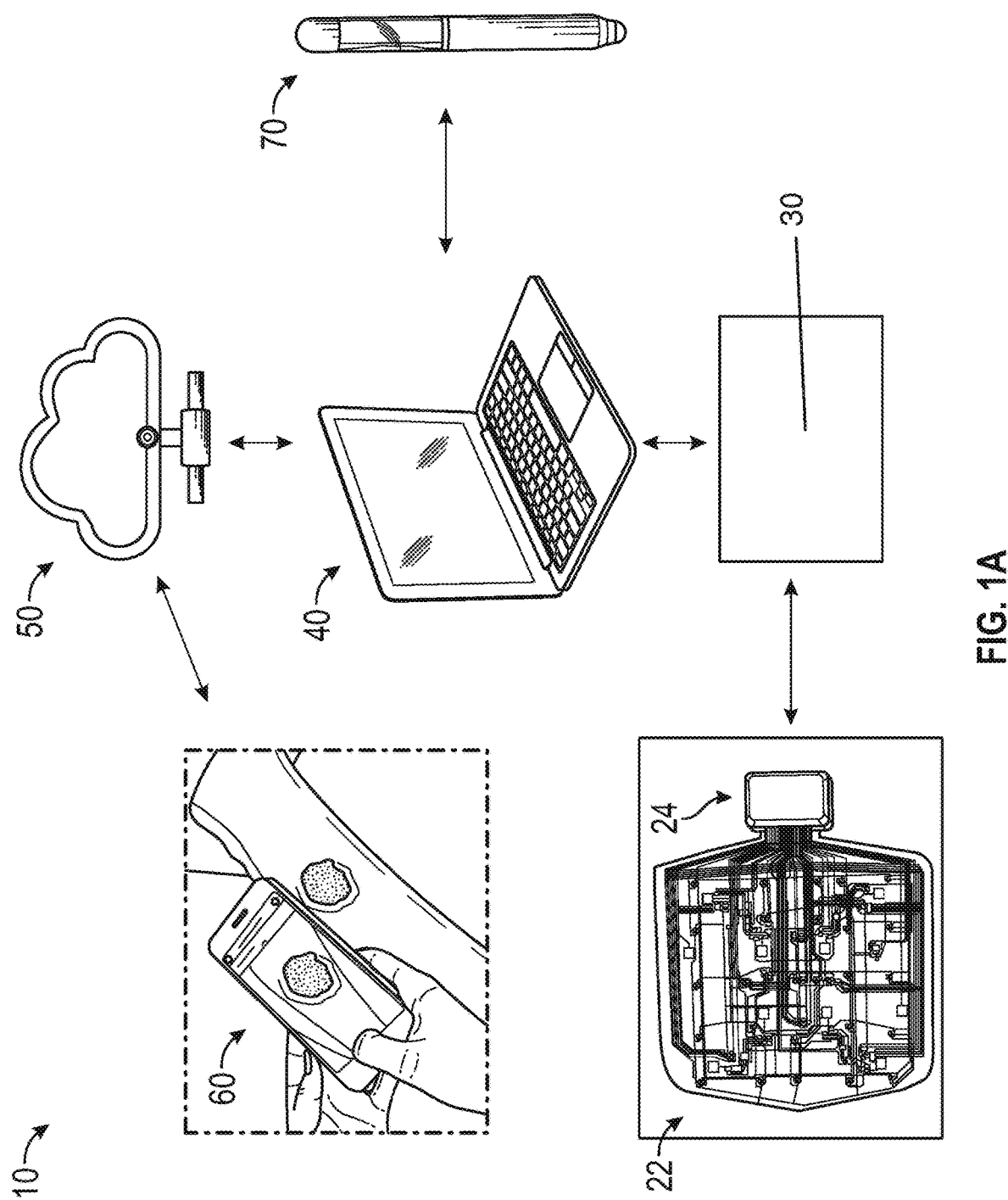
FIG. 1A illustrates a wound monitoring and therapy system according to some embodiments.

Embodiments disclosed herein relate to apparatuses and methods of monitoring and treating biological tissue with sensor-enabled substrates. The embodiments disclosed herein are not limited to treatment or monitoring of a particular type of tissue or injury, instead the sensor-enabled technologies disclosed herein are broadly applicable to any type of therapy that may benefit from sensor-enabled substrates. Some implementations utilize sensors and data collection relied upon by health care providers to make both diagnostic and patient management decisions.

Some embodiments disclosed herein relate to the use of sensors mounted on or embedded within substrates configured to be used in the treatment of both intact and damaged human or animal tissue. Such sensors may collect information about the surrounding tissue and transmit such information to a computing device or a caregiver to be utilized in further treatment. In certain embodiments, such sensors may be attached to the skin anywhere on the body, including areas for monitoring arthritis, temperature, or other areas that may be prone to problems and require monitoring. Sensors disclosed herein may also incorporate markers, such as radiopaque markers, to indicate the presence of the device, for example prior to performing an MRI or other technique.

The sensor embodiments disclosed herein may be used in combination with clothing. Non-limiting examples of clothing for use with embodiments of the sensors disclosed herein include shirts, pants, trousers, dresses, undergarments, outer-garments, gloves, shoes, hats, and other suitable garments. In certain embodiments, the sensor embodiments disclosed herein may be welded into or laminated into/onto the particular garments. The sensor embodiments may be printed directly onto the garment and/or embedded into the fabric. Breathable and printable materials such as microporous membranes may also be suitable.

Sensor embodiments disclosed herein may be incorporated into cushioning or bed padding, such as within a hospital bed, to monitor patient characteristics, such as any characteristic disclosed herein. In certain embodiments, a disposable film containing such sensors could be placed over the hospital bedding and removed/replaced as needed.

In some implementations, the sensor embodiments disclosed herein may incorporate energy harvesting, such that the sensor embodiments are self-sustaining. For example, energy may be harvested from thermal energy sources, kinetic energy sources, chemical gradients, or any suitable energy source.

The sensor embodiments disclosed herein may be utilized in rehabilitation devices and treatments, including sports medicine. For example, the sensor embodiments disclosed herein may be used in braces, sleeves, wraps, supports, and other suitable items. Similarly, the sensor embodiments disclosed herein may be incorporated into sporting equipment, such as helmets, sleeves, and/or pads. For example, such sensor embodiments may be incorporated into a protective helmet to monitor characteristics such as acceleration, which may be useful in concussion diagnosis.

The sensor embodiments disclosed herein may be used in coordination with surgical devices, for example, the NAVIO surgical system by Smith & Nephew Inc. In implementations, the sensor embodiments disclosed herein may be in communication with such surgical devices to guide placement of the surgical devices. In some implementations, the sensor embodiments disclosed herein may monitor blood flow to or away from the potential surgical site or ensure that there is no blood flow to a surgical site. Further surgical data may be collected to aid in the prevention of scarring and monitor areas away from the impacted area.

To further aid in surgical techniques, the sensors disclosed herein may be incorporated into a surgical drape to provide information regarding tissue under the drape that may not be immediately visible to the naked eye. For example, a sensor embedded flexible drape may have sensors positioned advantageously to provide improved area-focused data collection. In certain implementations, the sensor embodiments disclosed herein may be incorporated into the border or interior of a drape to create fencing to limit/control the surgical theater.

Sensor embodiments as disclosed herein may also be utilized for pre-surgical assessment. For example, such sensor embodiments may be used to collect information about a potential surgical site, such as by monitoring skin and the underlying tissues for a possible incision site. For example, perfusion levels or other suitable characteristics may be monitored at the surface of the skin and deeper in the tissue to assess whether an individual patient may be at risk for surgical complications. Sensor embodiments such as those disclosed herein may be used to evaluate the presence of microbial infection and provide an indication for the use of antimicrobials. Further, sensor embodiments disclosed herein may collect further information in deeper tissue, such as identifying pressure ulcer damage and/or the fatty tissue levels.

The sensor embodiments disclosed herein may be utilized in cardiovascular monitoring. For example, such sensor embodiments may be incorporated into a flexible cardiovascular monitor that may be placed against the skin to monitor characteristics of the cardiovascular system and communicate such information to another device and/or a caregiver. For example, such a device may monitor pulse rate, oxygenation of the blood, and/or electrical activity of the heart. Similarly, the sensor embodiments disclosed herein may be utilized for neurophysiological applications, such as monitoring electrical activity of neurons.

The sensor embodiments disclosed herein may be incorporated into implantable devices, such as implantable orthopedic implants, including flexible implants. Such sensor embodiments may be configured to collect information regarding the implant site and transmit this information to an external source. In some embodiments, an internal source may also provide power for such an implant.

The sensor embodiments disclosed herein may also be utilized for monitoring biochemical activity on the surface of the skin or below the surface of the skin, such as lactose buildup in muscle or sweat production on the surface of the skin. In some embodiments, other characteristics may be monitored, such as glucose concentration, urine concentration, tissue pressure, skin temperature, skin surface conductivity, skin surface resistivity, skin hydration, skin maceration, and/or skin ripping.

Sensor embodiments as disclosed herein may be incorporated into Ear, Nose, and Throat (ENT) applications. For example, such sensor embodiments may be utilized to monitor recovery from ENT-related surgery, such as wound monitoring within the sinus passage.

As described in greater detail below, the sensor embodiments disclosed herein may encompass sensor printing technology with encapsulation, such as encapsulation with a polymer film Such a film may be constructed using any polymer described herein, such as polyurethane. Encapsulation of the sensor embodiments may provide waterproofing of the electronics and protection from local tissue, local fluids, and other sources of potential damage.

In certain embodiments, the sensors disclosed herein may be incorporated into an organ protection layer such as disclosed below. Such a sensor-embedded organ protection layer may both protect the organ of interest and confirm that the organ protection layer is in position and providing protection. Further, a sensor-embedded organ protection layer may be utilized to monitor the underlying organ, such as by monitoring blood flow, oxygenation, and other suitable markers of organ health. In some embodiments, a sensor-enabled organ protection layer may be used to monitor a transplanted organ, such as by monitoring the fat and muscle content of the organ. Further, sensor-enabled organ protection layers may be used to monitor an organ during and after transplant, such as during rehabilitation of the organ.

The sensor embodiments disclosed herein may be incorporated into treatments for wounds (disclosed in greater detail below) or in a variety of other applications. Non-limiting examples of additional applications for the sensor embodiments disclosed herein include: monitoring and treatment of intact skin, cardiovascular applications such as monitoring blood flow, orthopedic applications such as monitoring limb movement and bone repair, neurophysiological applications such as monitoring electrical impulses, and any other tissue, organ, system, or condition that may benefit from improved sensor-enabled monitoring.

Wound Therapy

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein) wound with or without reduced pressure, including for example a source of negative pressure and wound dressing components and apparatuses. The apparatuses and components comprising the wound overlay and packing materials or internal layers, if any, are sometimes collectively referred to herein as dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body. The disclosed technology embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure and/or traditional advanced wound care, which is not aided by the using of applied negative pressure (may also be referred to as non-negative pressure therapy).

Advanced wound care may include use of an absorbent dressing, an occlusive dressing, use of an antimicrobial and/or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent. Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

In some embodiments, the disclosed technology may be used in conjunction with a non-negative pressure dressing. A non-negative pressure wound dressing suitable for providing protection at a wound site may comprise:

an absorbent layer for absorbing wound exudate and an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film Typically, the translucent film has a moisture vapour permeability of 500 g/m2/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm2.

The support layer may have a tensile strength from 0.05 to 0.06 Nm.

The support layer may have a thickness of from 50 to 150 µm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm2/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm2 of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm2 and 55 gm2, such as 35 gm2.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm2 and 250 gm2, or about 200 gm2.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments other compression bandage systems such as those disclosed in U.S. Pat. No. 6,759,566 and US 2002/0099318, the entirety of each of which is hereby incorporated by reference.

Negative Pressure Wound Dressing

In some embodiments, treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

Negative pressure therapy can be used for the treatment of open or chronic wounds that are too large to spontaneously close or otherwise fail to heal by means of applying negative pressure to the site of the wound. Topical negative pressure (TNP) therapy or negative pressure wound therapy (NPWT) involves placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines or bacteria.

Some of the dressings used in NPWT can include many different types of materials and layers, for example, gauze, pads, foam pads or multi-layer wound dressings. One example of a multi-layer wound dressing is the PICO dressing, available from Smith & Nephew, includes a wound contact layer and a superabsorbent layer beneath a backing layer to provide a canister-less system for treating a wound with NPWT. The wound dressing may be sealed to a suction port providing connection to a length of tubing, which may be used to pump fluid out of the dressing or to transmit negative pressure from a pump to the wound dressing. Additionally, RENASYS-F, RENASYS-G, RENASYS-AB, and RENASYS-F/AB, available from Smith & Nephew, are additional examples of NPWT wound dressings and systems. Another example of a multi-layer wound dressing is the ALLEVYN Life dressing, available from Smith & Nephew, which includes a moist wound environment dressing that is used to treat the wound without the use of negative pressure.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg In addition, negative pressure that is "less" or "smaller" than X mmHg corresponds to pressure that is closer to atmospheric pressure (such as, −40 mmHg is less than −60 mmHg). Negative pressure that is "more" or "greater" than −X mmHg corresponds to pressure that is further from atmospheric pressure (such as, −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg Note that these pressures are relative to normal ambient atmospheric pressure, which can be 760 mmHg Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which is hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS," the disclosure of which is hereby incorporated by reference in its entirety.

Sensor Enabled Wound Monitoring and Therapy System

FIG. 1A illustrates a wound monitoring and therapy system 10 according to some embodiments. The system includes a sensor enabled wound dressing 22 connected to a controller 24. As is described herein, the dressing 22 can be placed on or in a wound of a patient and can utilize various sensors embedded or otherwise placed in the dressing 22 to collect measurement data from one or more of the wound or areas surrounding the wound, such as the periwound. The controller 24 can receive, store, and process data collected by the dressing 22. To facilitate communication, the dressing 22 can include one or more communication modules, such as one or more antennas as described herein. In some cases, the controller 24 can transmit one or more of commands and data to the dressing 22.

In some embodiments, wound dressing 22 can be disposable and controller 24 can be reusable. In some embodiments, wound dressing 22 can be reusable. In some embodiments, wound dressing 22 can be re-sterilized or otherwise sanitized or disinfected. In some embodiments, controller 24 can be disposable. In some embodiments, wound dressing 22 and controller 24 can be permanently connected and the combined wound dressing and control box be disposable, or reusable or re-sterilized or otherwise sanitized or disinfected. The controller 24 can include a power source (such as a battery), one or more processors, one or more storage elements, and a communication device. In some embodiments, the controller 24 can include one or more sensors, such as a temperature sensor or optical sensor to gather information on patient or environmental conditions located away from the wound dressing. In some embodiments, the one or more sensors of the controller 24 can include an accelerometer, motion sensor or gyroscope. In some embodiments, the wound dressing 22 can include one or more indicators to communicate information to a user. The indicators can be visual, audible, haptic and/or tactile. Communicated information can include measurement data, wound status, or the like.

The controller 24 can communicate data to a communication device 30 as requested, periodically, or the like. Communication can be performed over a wired or wireless interface, such as via near field communication (NFC), RFID, or the like when the communication device is placed in communication range. For example, communication range can be close proximity, such as within approximately 3 cm or less or more, to the controller 24. Communication device 30 can be placed in communication range by a clinician, such as during initialization and at the end of treatment. The controller 24 can respond with data to a command from the communication device 30 requesting data. The communication device 30 can be connected via a wired or wireless interface to a computing device 40, such as a personal computer, tablet, smartphone, or the like. For example, wired USB protocol can be used for communication data between devices 30 and 40. Computing device 40 can further process data collected by the dressing 22. For example, the computing device 40 can aggregate data collected from the dressing 22 and perfusion determination device 70, which is configured to determine skin perfusion pressure and communicate data to the computing device 40 via a wired or wireless interface. For example, wired USB protocol can be used for communication between devices 70 and 40.

Computing device 40 can be configured to communicate via a wired or wireless interface with a remote computing device 50 that stores and processes medical data. In some embodiments, remote computing device 50 can be a cloud computing device, which includes one or more of remote storage, server, processing device, or any means of information storage. For example, remote computing device 50 can process and store medical data according with one or more applicable security and privacy standards, such as Health Insurance Portability & Accountability Act (HIPPA), European Union's Directive on Data Protection, or the like. Remote computing device 50 can make data provided by one or more of the computing device 40 or the mobile device 60 available for remote accessing and viewing, such as on a mobile device 60. In certain implementations, additional data can be added for storage on the remote computing device 50. For example, additional data can be added by the mobile device 60 via a dedicated app, web browser interface, or the like. The remote computing device 50 can process the data from one or more of the wound dressing 22, perfusion determination device 70, or the mobile device and assess or determine treatment plan, such as suggest or adjust one or more treatment therapies.

As described herein, mobile device 60 can take one or more images of a patient's wound. Such data can be transmitted via wired or wireless interface to the remote computing device 50. Although a smartphone is illustrated, mobile device 60 can be any suitable computing device that includes imaging functionality, such as a camera. Mobile device 60 can also collect additional data, such as data input by a healthcare provider in response to a questionnaire.

Various components illustrated in FIG. 1A are described in more detail in other portions of the present disclosure.

Figure 1B:
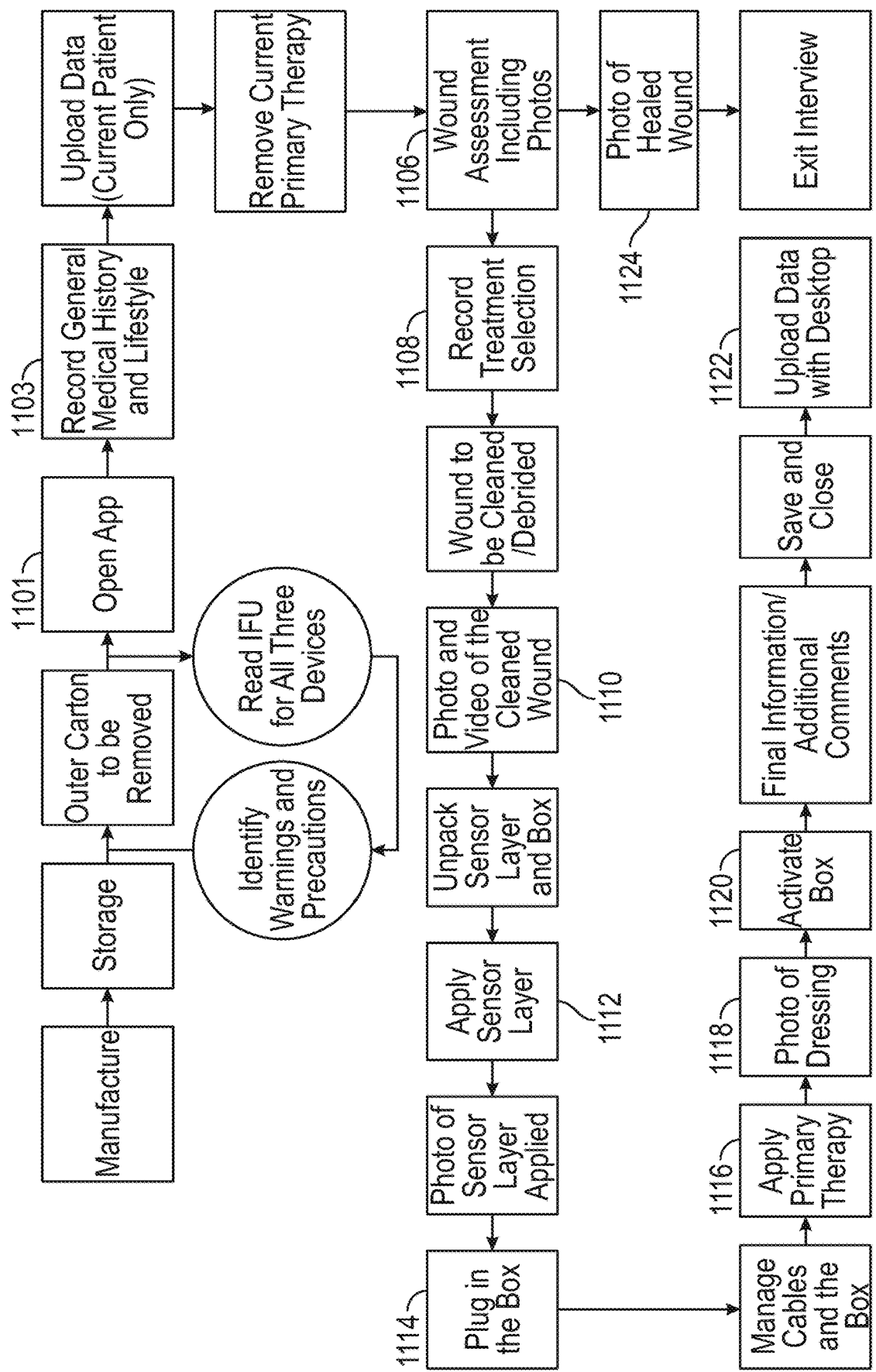
FIG. 1B illustrate the use of a wound monitoring and therapy system according to some embodiments.

FIG. 1B illustrates the use of a wound monitoring and therapy system, such as the system 10, according to some embodiments. As is illustrated, in blocks 1101 and 1103, a user (such as, healthcare provider (HCP)), can provide information regarding patient's medical history and lifestyle. Such information can be provided via the mobile device 60 for storage on the remote computing device 50 as described herein (such as, via an app). In block 1106, assessment of the wound can be performed. For example, images of the wound can be taken by the mobile device 60 and uploaded to the remote computing device 50 as described herein. Alternatively or additionally, skin perfusion pressure can be measured by the device 70 and uploaded to the remote computing device 50 as described herein.

In block 1108, treatment decision of the user can be recorded. For example, one or more treatment therapies can be selected, such as negative pressure wound therapy. In block 1110, additional images of the clean and, if applicable, debrided wound can be taken and uploaded to the remote computing device. In block 1112, wound dressing 22 can be placed in or on wound of the patient. In block 1114, controller 24 can be connected to the wound dressing 22, in cases where the wound dressing and controller are separate. The wound dressing can be initialized as described herein. In block 1116, one or more selected therapies can be applied. In block 1118, images of the wound covered by the wound dressing 22 can be taken and uploaded. In block 1120, measurement data from the wound dressing 22 can be collected and stored, as described herein. This step can be performed as many times as suitable while the wound dressing 22 is applied to the patient. Upon completion of therapy, in block 1122, measurement data can be uploaded to the remote computing device 50 as described herein. In block 1124, images of healed wound can be taken.

In some embodiments, one or more images of the wound can be processed using Eulerian magnification techniques described in International Patent Application No. PCT/EP2018/062207, titled NEGATIVE PRESSURE WOUND THERAPY SYSTEM USING EULERIAN VIDEO MAGNIFICATION, filed on 11 May 2018, which claims the benefit of U.S. Provisional Patent Application No. 62/506,524, titled NEGATIVE PRESSURE WOUND THERAPY SYSTEM USING EULERIAN VIDEO MAGNIFICATION, filed on 15 May 2017, and International Patent Application No. PCT/EP2018/062206, titled WOUND ANALYSIS DEVICE AND METHOD, filed on 11 May 2018, which claims the benefit of U.S. Provisional Patent Application No. 62/506,551, titled WOUND ANALYSIS DEVICE AND METHOD, filed on 15 May 2017, each of which is incorporated by reference in its entirety. Eulerian magnification techniques can be implemented by any of the components of the system 10, such as the mobile device 60 or remote computing device 50.

Sensor Enabled Wound Dressing

Figure 1C:
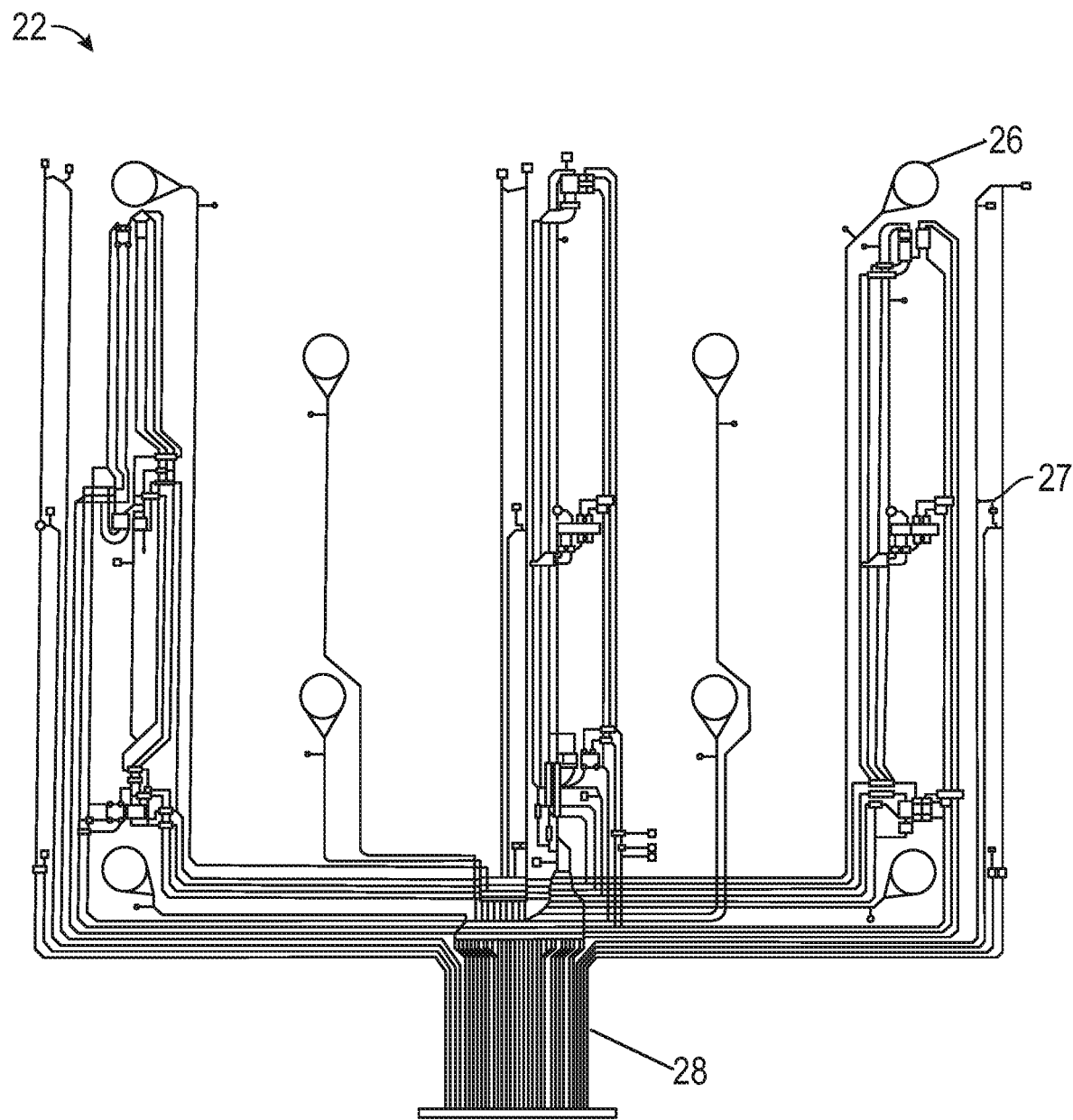
FIG. 1C illustrates a sensor enabled wound dressing according to some embodiments.

FIG. 1C illustrates sensor enabled wound dressing 22 according to some embodiments. As described herein, the wound dressing 22 can include a substantially flexible substrate that can include a wound contact layer having one or more features of any of the wound contact layers described herein. As is used herein, "wound contact layer" can imply the wound contact layer together with the substrate, and "substrate" can imply both the substrate and wound contact layer together. The wound dressing 22 can include any of the wound dressing layers described herein. The entire wound dressing 22 can be substantially flexible. As is illustrated, one or more sensors 26 connected by one or more electronic connections or tracks 27 are positioned or embedded in the wound dressing 22. In some embodiments, one or more sensors of the wound dressing 22 can measure one or more of impedance, temperature, optical properties, or the like. In some embodiments, one or more sensors of the wound dressing 22 or any other wound dressing disclosed herein can measure one or more of impedance, temperature, pH, pressure (such as, by using a strain gauge), elasticity of tissue (such as, by using an ultrasound sensor, piezoelectric transducer, or the like, blood flow (such as, by measuring the Doppler effect), color, or light. One or more sensors can be electronic or non-electronic. Examples of non-electronic sensors include sensors that change color as a function of pH or when stretched, strained, or otherwise subjected to pressure. Measurements of such sensors can be obtained through visual monitoring, which can be performed automatically, such as by using a camera or by using one or more optical sensors. The one or more sensors and connections can be positioned on the wound contact layer. Also illustrated is a connector 28 for connecting to wound dressing 22 to the controller 24. The connector 28 includes one or more electrical connections or tracks. In some implementations, borders or edges of the wound contact layer can be smoothed by cuts, have smooth contours, include fibers, and/or the like to improve patient comfort.

In some embodiments, the dressing can include one or more antennas for wireless communication. For example, one or more antennas can be printed as one or more connections or traces on the wound contact layer. The one or more antennas can be used to communicate measurement data collected by the one or more sensors without the controller 24. The one or more antennas can additionally be used to receive power wirelessly from a power source. In certain cases, the one or more antenna traces can be positioned on a substantially non-stretchable material (as described herein) such that the resonant frequencies of the one or more antennas remain fixed when the wound dressing 22 is placed under stress when in use on a patient. Fixing the one or more resonant frequencies can be advantageous for certain communication protocols, such as RFID.

Negative Pressure Wound Therapy System

Figure 2A:
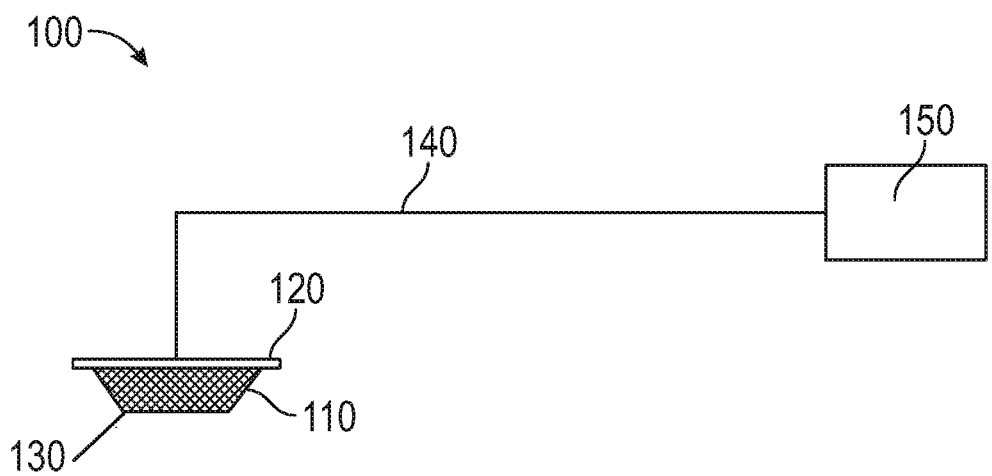
FIG. 2A illustrates a negative pressure wound treatment system according to some embodiments.

FIG. 2A illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as a wound dressing. The wound dressing may include one or more sensors as described herein. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 2A, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2011/0213287, 2011/0282309, 2012/0116334, 2012/0136325, and 2013/0110058, which are incorporated by reference in their entirety. In other embodiments, other suitable wound dressings can be utilized.

Wound Dressing Overview

Figure 2B:
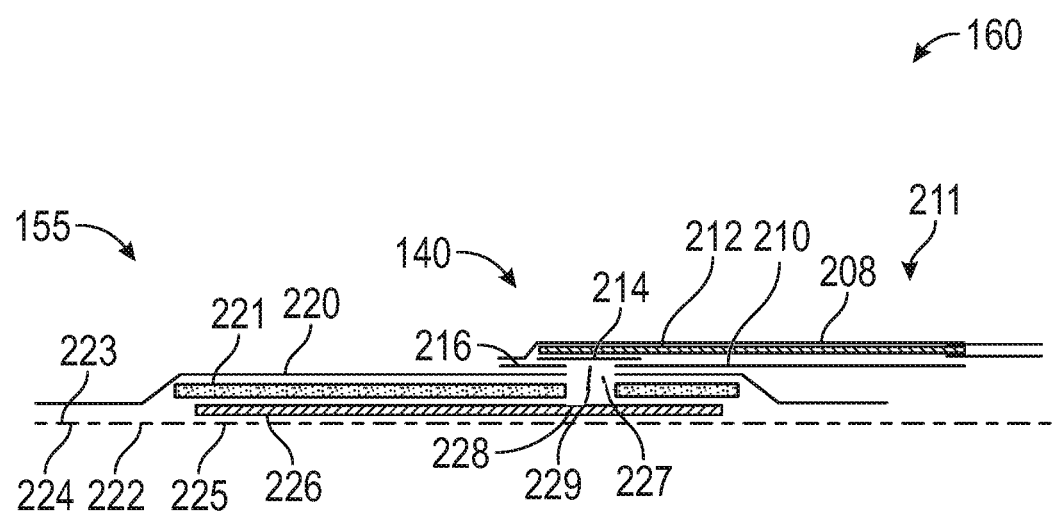
FIG. 2B illustrates a wound dressing according to some embodiments.

FIG. 2B illustrates a cross-section through a wound dressing 155 according to some embodiments. FIG. 2B also illustrates a fluidic connector 160 according to some embodiments. The wound dressing 155 can be similar to the wound dressing described in International Patent Publication WO2013175306 A2, which is incorporated by reference in its entirety. Alternatively, the wound dressing 155 can be any wound dressing embodiment disclosed herein or any combination of features of any number of wound dressing embodiments disclosed herein, can be located over a wound site to be treated. The wound dressing 155 may be placed as to form a sealed cavity over the wound, such as the wound cavity 110. In some embodiments, the wound dressing 155 includes a top or cover layer, or backing layer 220 attached to an optional wound contact layer 222, both of which are described in greater detail below. These two layers 220, 222 can be joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the layer 222. The wound contact layer 222 helps prevent tissue ingrowth into the other material of the wound dressing. In some embodiments, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 155 while also creating an air tight seal around the absorbent pad in order to maintain negative pressure at the wound. In some embodiments, the wound contact layer is configured to allow unidirectional or substantially one-way or unidirectional flow of fluid through the wound contact layer when negative pressure is applied to the wound. For example, the wound contact layer can permit fluid to flow away from the wound through the wound contact layer, but not allow fluid to flow back toward the wound. In certain case, the perforations in the wound contact layer are configured to permit such one-way or unidirectional flow of fluid through the wound contact layer.

Some embodiments of the wound contact layer 222 may also act as a carrier for an optional lower and upper adhesive layer (not shown). For example, a lower pressure sensitive adhesive may be provided on the lower surface 224 of the wound dressing 155 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 155 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 can ensure that an open air channel can be maintained to communicate negative pressure over the wound area even when the absorbent layer has absorbed substantial amounts of exudates. The layer 226 can remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

In some embodiments, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. An additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material can be provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

The material of the absorbent layer 221 may also prevent liquid collected in the wound dressing 155 from flowing freely within the dressing, and can act so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 or Chem-Posite™ 11C-450. In some embodiments, the absorbent layer 221 may comprise a composite comprising superabsorbent powder, fibrous material such as cellulose, and bonding fibers. In a some embodiments, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 can be provided in the backing layer 220 to allow a negative pressure to be applied to the dressing 155. In some embodiments, the fluidic connector 160 is attached or sealed to the top of the backing layer 220 over the orifice 227 made into the dressing 155, and communicates negative pressure through the orifice 227. A length of tubing may be coupled at a first end to the fluidic connector 160 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 160 may be adhered and sealed to the backing layer 220 using an adhesive such as an acrylic, cyanoacrylate, epoxy, UV curable or hot melt adhesive. The fluidic connector 160 may be formed from a soft polymer, for example a polyethylene, a polyvinyl chloride, a silicone or polyurethane having a hardness of 30 to 90 on the Shore A scale. In some embodiments, the fluidic connector 160 may be made from a soft or conformable material.

In some embodiments, the absorbent layer 221 includes at least one through hole 228 located so as to underlie the fluidic connector 160. The through hole 228 may in some embodiments be the same size as the opening 227 in the backing layer, or may be bigger or smaller. As illustrated in FIG. 2B a single through hole can be used to produce an opening underlying the fluidic connector 160. It will be appreciated that multiple openings could alternatively be utilized. Additionally should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 can be provided in the absorbent layer 221 beneath the orifice 227 such that the orifice is connected directly to the transmission layer 226 as illustrated in FIG. 2B. This allows the negative pressure applied to the fluidic connector 160 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is can be gas impermeable, but moisture vapor permeable, and can extend across the width of the wound dressing 155. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 can be sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 can include two layers; a polyurethane film and an adhesive pattern spread onto the film. The polyurethane film can be moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 155 comprises an aperture 228 in the absorbent layer 221 situated underneath the fluidic connector 160. In use, for example when negative pressure is applied to the dressing 155, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

For example, in embodiments with a single fluidic connector 160 and through hole, it may be preferable for the fluidic connector 160 and through hole to be located in an off-center position. Such a location may permit the dressing 155 to be positioned onto a patient such that the fluidic connector 160 is raised in relation to the remainder of the dressing 155. So positioned, the fluidic connector 160 and the filter 214 may be less likely to come into contact with wound fluids that could prematurely occlude the filter 214 so as to impair the transmission of negative pressure to the wound site.

Turning now to the fluidic connector 160, some embodiments include a sealing surface 216, a bridge 211 with a proximal end (closer to the negative pressure source) and a distal end 140, and a filter 214. The sealing surface 216 can form the applicator that is sealed to the top surface of the wound dressing. In some embodiments a bottom layer of the fluidic connector 160 may comprise the sealing surface 216. The fluidic connector 160 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 160 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 155 similar to the suction adapter as described in U.S. Pat. No. 8,801,685, which is incorporated by reference herein in its entirety.

In some embodiment, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected can be suited to channeling wound exudate away from the wound and for transmitting negative pressure or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between −40 to −150 mmHg In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system can be conformable and soft, which may help to avoid pressure ulcers and other complications which may result from a wound treatment system being pressed against the skin of a patient.

In some embodiments, the filter element 214 is impermeable to liquids, but permeable to gases, and is provided to act as a liquid bather and to ensure that no liquids are able to escape from the wound dressing 155. The filter element 214 may also function as a bacterial barrier. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port or the cover film over the orifice. For example, the filter element 214 may be molded into the fluidic connector 160, or may be adhered to one or both of the top of the cover layer and bottom of the suction adapter 160 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments, filter element 214 comprises a support layer and an acrylic co-polymer membrane formed on the support layer. In some embodiments, the wound dressing 155 according to certain embodiments uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 155 may comprise spacer elements 215 in conjunction with the fluidic connector 160 and the filter 214. With the addition of such spacer elements 215 the fluidic connector 160 and filter 214 may be supported out of direct contact with the absorbent layer 220 or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described herein, some wound dressings comprise a perforated wound contact layer, which can include silicone adhesive on the wound- or skin-contact face and/or acrylic adhesive on the reverse. The wound contact layer can be perforated to match any pattern suitable for a particular wound. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Wound Dressing with Sensors

As described herein, a wound dressing that incorporates a number of sensors can be utilized in order to monitor characteristics of a wound as it heals. Collecting data from the wounds that heal well, and from those that do not, can provide useful insights towards identifying measurands to indicate whether a wound is on a healing or non-healing trajectory. Any of the disclosed wound dressings, such as wound dressing 22 can include one or more of the following features or any other features disclosed herein.

Figure 3:
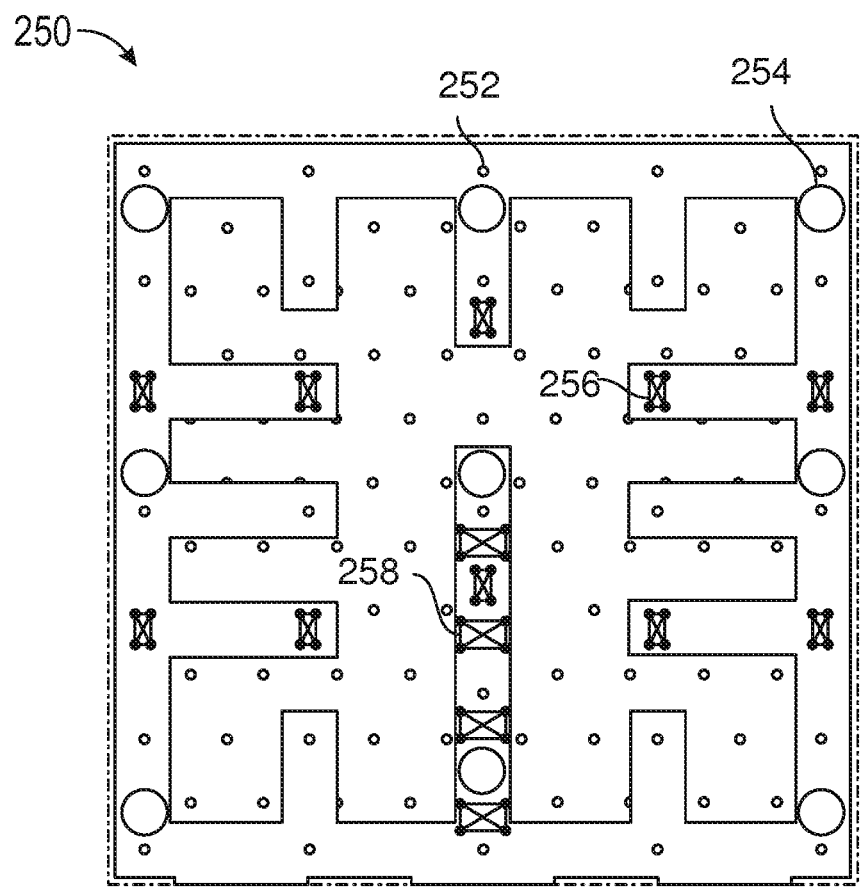
FIG. 3 illustrates a sensor array illustrating the sensor placement incorporated into a wound dressing according to some embodiments.
Figure 4A:
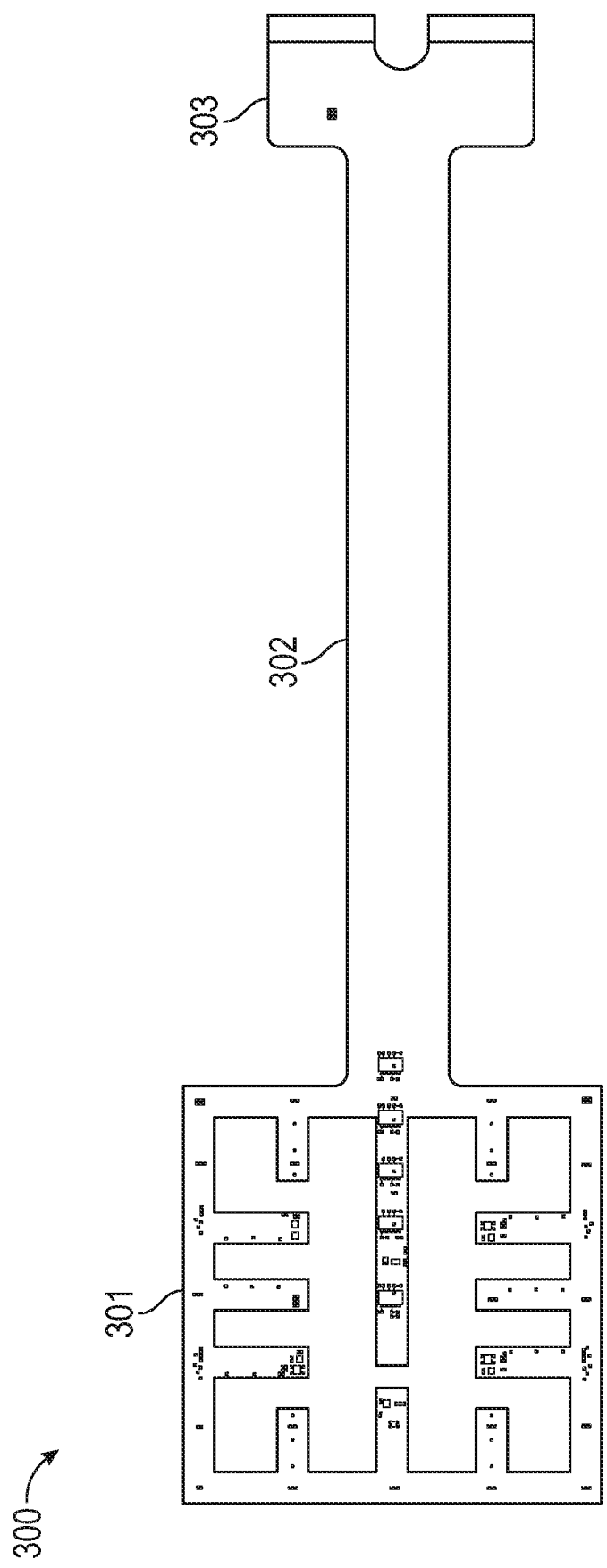
FIG. 4A illustrates a flexible sensor array including a sensor array portion, a tail portion and a connector pad end portion according to some embodiments.

In some implementations, a number of sensor technologies can be used in wound dressings or one or more components forming part of an overall wound dressing apparatus. For example, as illustrated in FIGS. 3 and 4D, which depict wound dressings 250 and 320 with sensor arrays according to some embodiments, one or more sensors can be incorporated onto or into a wound contact layer, which may be a perforated wound contact layer as shown in FIG. 4D. In some embodiments, as illustrated in FIG. 3, the wound dressing 250 can include temperature sensors 252, conductivity sensors 254, optical sensors 256, and/or SpO2 sensors 258. The wound contact layer in FIGS. 3 and 4D is illustrated as having a square shape, but it will be appreciated that the wound contact layer may have other shapes such as rectangular, circular, oval, etc. In some embodiments, the sensor integrated wound contact layer can be provided as an individual material layer that is placed over the wound area and then covered by a wound dressing apparatus or components of a wound dressing apparatus, such as gauze, foam or other wound packing material, a superabsorbent layer, a drape, a fully integrated dressing like the Pico or Allevyn Life dressing, etc. In other embodiments, the sensor integrated wound contact layer may be part of a single unit dressing such as described herein.

The sensor-integrated wound contact layer can be placed in contact with the wound and will allow fluid to pass through the contact layer while causing little to no damage to the tissue in the wound. The sensor-integrated wound contact layer can be made of a flexible material such as silicone and can incorporate antimicrobials or other therapeutic agents known in the art. In some embodiments, the sensor-integrated wound contact layer can incorporate adhesives that adhere to wet or dry tissue. In some embodiments, the sensors or sensor array can be incorporated into or encapsulated within other components of the wound dressing such as the absorbent layer or spacer layer described above.

As shown in FIGS. 3 and 4D, five sensors can be used, including, for instance, sensors for temperature (such as, 25 thermistor sensors, in a 5×5 array, ~20 mm pitch), oxygen saturation or SpO2 (such as, 4 or 5 SpO2 sensors, in a single line from the center of the wound contact layer to the edge thereof, 10 mm pitch), tissue color (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and conductivity (such as, 9 conductivity contacts, in a 3×3 array, ~40 mm pitch). As shown in FIG. 4A, the SpO2 sensors can be arranged in a single line from the center of or near the center of the wound contact layer to the edge of the wound contact layer. The line of SpO2 sensors can allow the sensor to take measurements in the middle of the wound, at the edge or the wound, or on intact skin to measure changes between the various regions. In some embodiments, the wound contact layer or sensor array can be larger than the size of the wound to cover the entire surface area of the wound as well as the surrounding intact skin. The larger size of the wound contact layer and/or sensor array and the multiple sensors can provide more information about the wound area than if the sensor was only placed in the center of the wound or in only one area at a time.

The sensors can be incorporated onto flexible circuit boards formed of flexible polymers including polyamide, polyimide (PI), polyester, polyethylene naphthalate (PEN), polyetherimide (PEI), along with various fluoropolymers (FEP) and copolymers, or any material known in the art. The sensor array can be incorporated into a two-layer flexible circuit. In some embodiments, the circuit board can be a multi-layer flexible circuit board. In some embodiments, these flexible circuits can be incorporated into any layer of the wound dressing. In some embodiments, a flexible circuit can be incorporated into a wound contact layer. For example, the flexible circuit can be incorporated into a wound contact layer similar to the wound contact layer described with reference to FIG. 2B. The wound contact layer can have cutouts or slits that allow for one or more sensors to protrude out of the lower surface of the wound contact layer and contact the wound area directly.

In some embodiments, the sensor-integrated wound contact layer can include a first and second wound contact layer with the flexible circuit board sandwiched between the two layers of wound contact layer material. The first wound contact layer has a lower surface intended to be in contact with the wound and an upper surface intended to be in contact with flexible circuit board. The second wound contact layer has a lower surface intended to be in contact with the flexible circuit board and an upper surface intended to be in contact with a wound dressings or one or more components forming part of an overall wound dressing apparatus. The upper surface of the first wound contact layer and the lower surface of the second wound contact layer can be adhered together with the flexible circuit board sandwiched between the two layers.

In some embodiments, the one or more sensors of the flexible circuit board can be fully encapsulated or covered by the wound contact layers to prevent contact with moisture or fluid in the wound. In some embodiments, the first wound contact layer can have cutouts or slits that allow for one or more sensors to protrude out of the lower surface and contact the wound area directly. For example, the one or more SpO2 sensors as shown in FIG. 4D are shown protruding out the bottom surface of the wound contact layer. In some embodiments, the SpO2 sensors can be mounted directly on a lower surface of the first wound contact layer. Some or all of the sensors and electrical or electronic components may be potted or encapsulated (for example, rendered waterproof or liquid-proof) with a polymer, for example, silicone or epoxy based polymers. The encapsulation with a polymer can prevent ingress of fluid and leaching of chemicals from the components. In some embodiments, the wound contact layer material can seal the components from water ingress and leaching of chemicals.

In some embodiments, gathering and processing information related to the wound can utilize three components, including a sensor array, a control or processing module, and software. These components are described in more detail herein.

FIG. 4A illustrates a flexible sensor array circuit board 300 that includes a sensor array portion 301, a tail portion 302, and a connector pad end portion 303 according to some embodiments. The sensor array portion 301 can include the sensors and associated circuitry. The sensor array circuit board 300 can include a long tail portion 302 extending from the sensor array portion 301. The connector pad end portion 303 can be enabled to connect to a control module or other processing unit to receive the data from the sensor array circuit. The long tail portion 302 can allow the control module to be placed distant from the wound, such as for example in a more convenient location away from the wound.

Figure 4B:
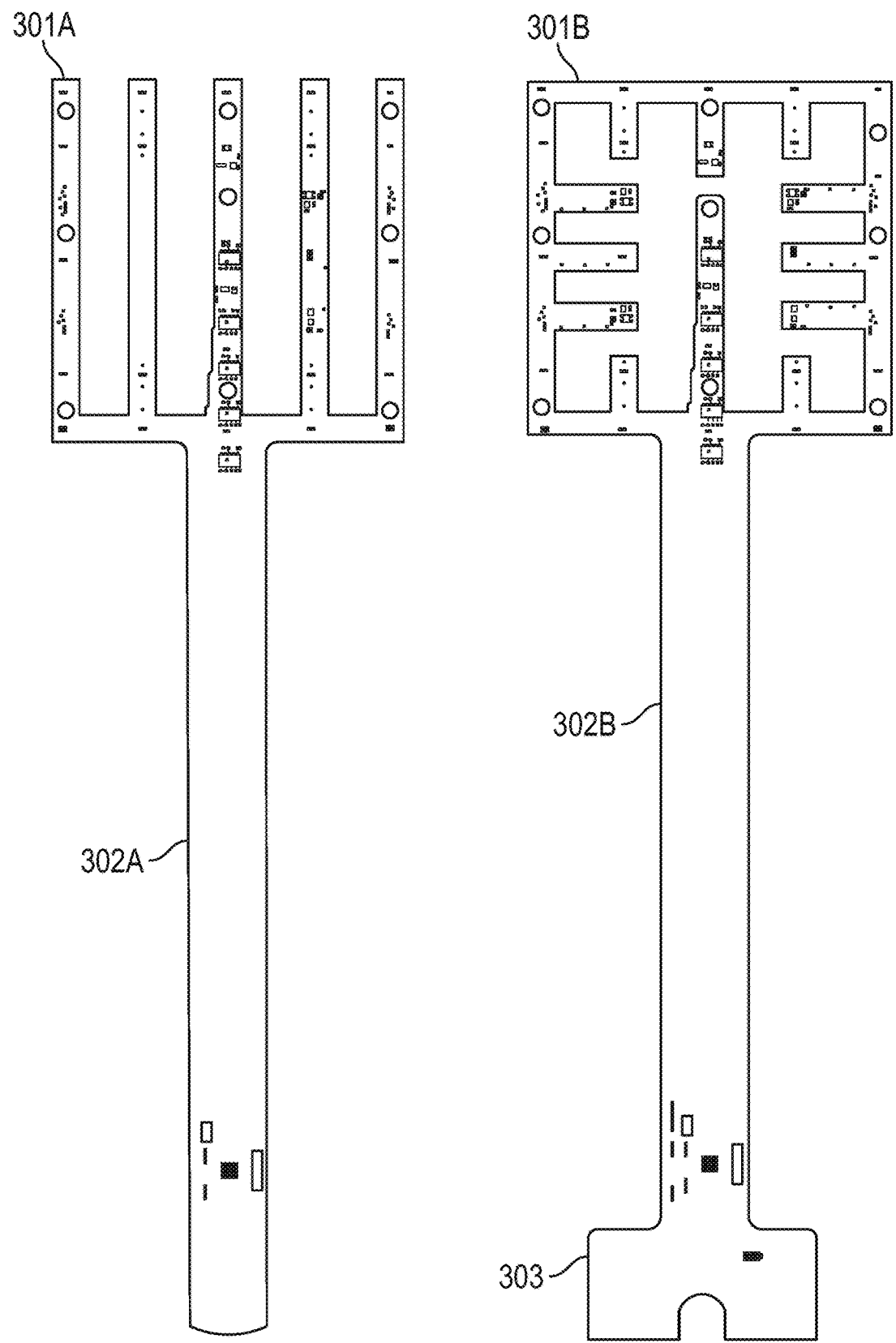
FIG. 4B illustrates flexible circuit boards with different sensor array geometries according to some embodiments.
Figure 4B:
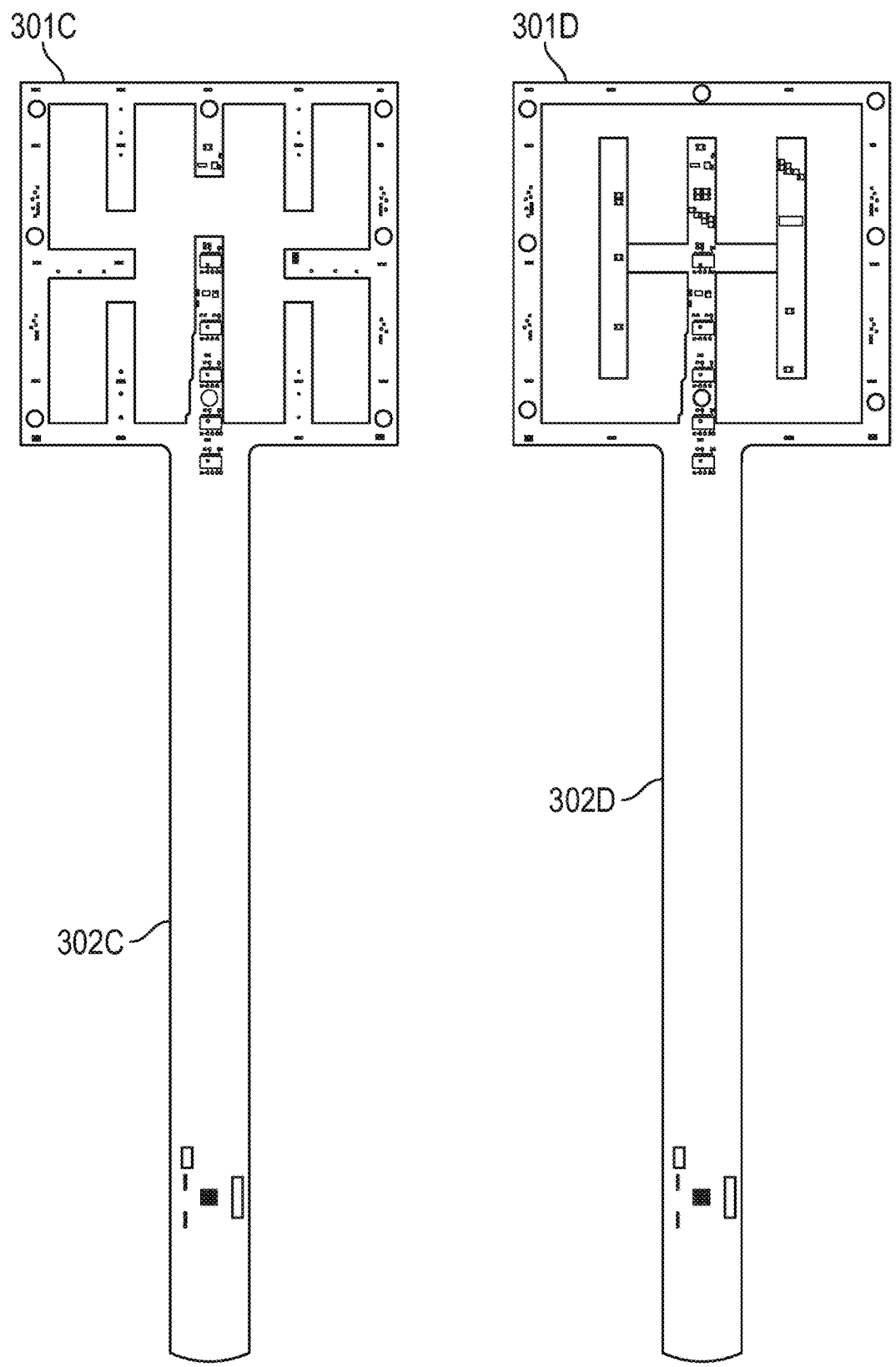

FIG. 4B illustrates embodiments of the flexible circuit boards with four different sensor array geometries 301A, 301B, 301C, and 301D according to some embodiments. The illustrated embodiments include tail portions 302A, 302B, 302C, and 302D. In some embodiments, flexible circuit boards include a short portion or no tail portion. In some embodiments, four different sensor array geometries shown can be implemented in flexible circuits. While FIG. 4B show four different sensor array formats and configurations, the design 301B and 302B also includes the connector pads end portion 303 configured to provide electrical or electronic connection between the sponsor array 301B and a control module. One or more of the designs in 301A, 301C, or 301D can also include a connector pads end portion, such as the portion 303, to allow flexible circuit boards 301A, 301C, or 301D to communicate with a control module or other processing unit. In some embodiments, the sensor array communicates with the control module wirelessly and the tail portion may be omitted.

Figure 4C:
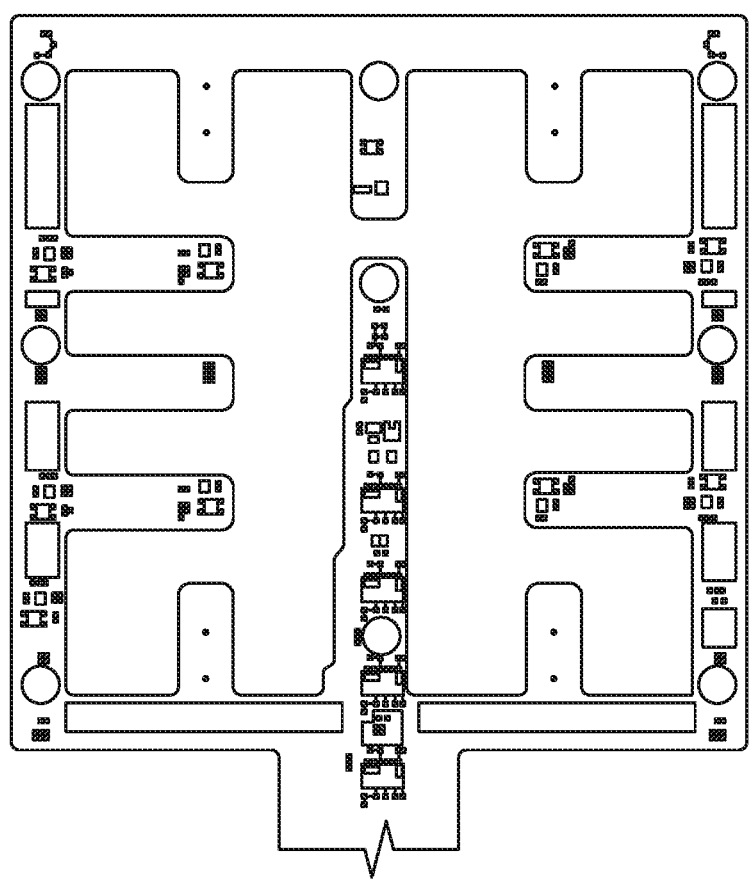
FIG. 4C illustrates the sensor array portion 301B of a sensor array shown in FIG. 4B.
Figure 4D:
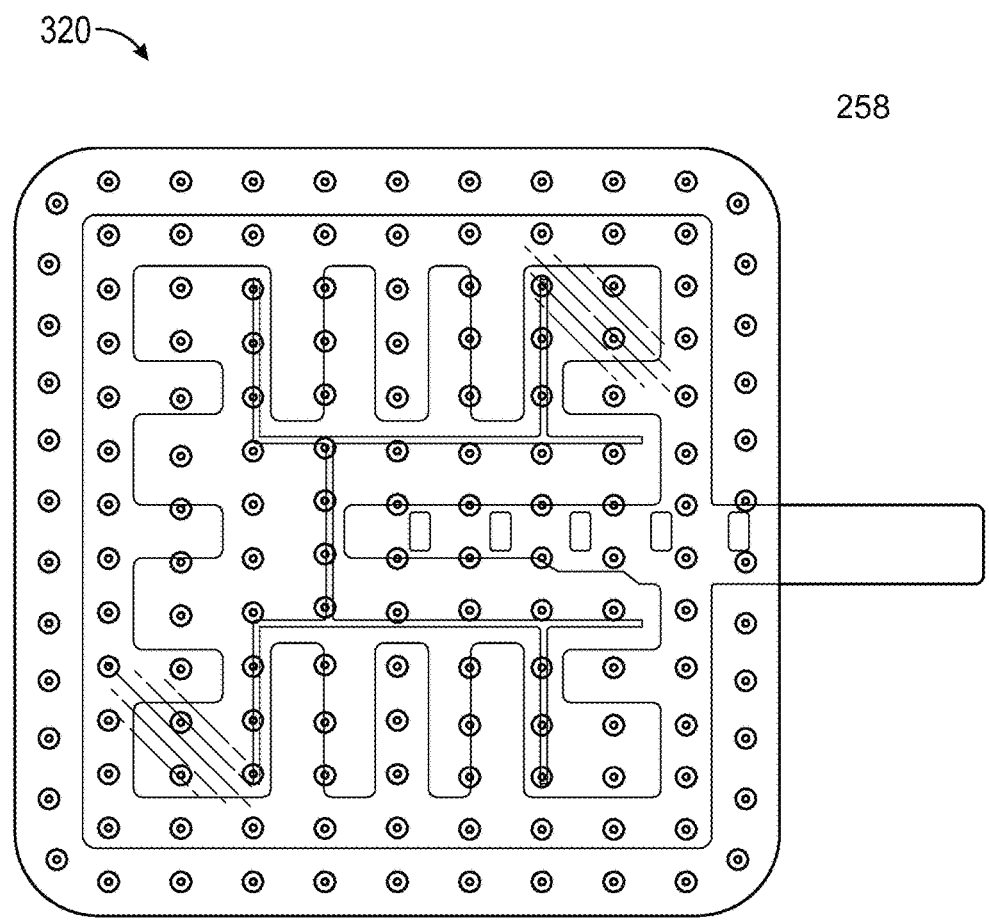
FIG. 4D illustrates a flexible sensor array incorporated into a perforated wound contact layer according to some embodiments.

FIG. 4C shows the sensor array portion 301B of the sensor array design of FIG. 4B in more detail. In any one or more of the embodiments of FIG. 3 or 4A-4D, the sensor array portion can include a plurality of portions that extend either around a perimeter of a wound dressing component such as a wound contact layer, or inward from an outer edge of the wound dressing component. For example, the illustrated embodiments include a plurality of linearly extending portions that may be parallel to edges of a wound dressing component, and in some embodiments, follow the entire perimeter of the wound dressing component. In some embodiments, the sensor array portion may comprise a first plurality of parallel linearly extending portions that are perpendicular to a second plurality of parallel linearly extending portions. These linearly extending portions may also have different lengths and may extend inward to different locations within an interior of a wound dressing component. The sensor array portion preferably does not cover the entire wound dressing component, so that gaps are formed between portions of the sensor array. As shown in FIG. 3, this allows some, and possibly a majority of the wound dressing component to be uncovered by the sensor array. For example, for a perforated wound contact layer as shown in FIGS. 3 and 4D, the sensor array portion 301 may not block a majority of the perforations in the wound contact layer. In some embodiments, the sensor array may also be perforated or shaped to match the perforations in the wound contact layer to minimize the blocking of perforations to fluid flow.

FIG. 4D illustrates a flexible sensor array incorporated into a perforated wound contact layer 320 according to some embodiments. As is illustrated, the sensor array can be sandwiched between two films or wound contact layers. The wound contact layers can have perforations formed as slits or holes as described herein that are small enough to help prevent tissue ingrowth into the wound dressing while allowing wound exudate to flow into the dressing. In some embodiments, the wound contact layers can have one or more slits that increase flexibility of the wound contact layer with integrated sensor array. In some embodiments, one of the wound contact layers can have extra cut outs to accommodate the sensors so that they can contact the skin directly.

Connectivity for the sensor array can vary depending on the various sensors and sensor array designs utilized. In some embodiments, for example as shown in FIG. 4B, a total of 79 connections can be used to connect the components of the sensor array. The sensor arrays can be terminated in two parallel 40-way 0.5 mm pitch Flat Flexible Cable (FFC) contact surfaces, with terminals on the top surface, designed to be connected to an FFC connector such as Molex 54104-4031.

In some embodiments, one or more of the sensors, such as thermistors, conductivity sensors, SpO2 sensors, color sensors, or the like can be used on the sensor array to provide information relating to conditions of the wound and/or periwound. Any of the sensor array and/or individual sensors disclosed herein can assist a clinician in monitoring the status of the wound, which can include healing of the wound and/or non-healing of the wound (such as, static, degrading, or the like). The one or more sensors can operate individually or in coordination with each other to provide data relating to the wound and wound healing characteristics.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. In some embodiments, an ambient sensor measuring ambient air temperature can also be used to assist in eliminating problems associated with environment temperature shifts.

Optical sensors can be used to measure wound appearance using an RGB sensor with an illumination source. In some embodiments, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomize the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofluorescence. Autofluorescence is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

Conductivity sensors can be used to determine the difference between living and dead tissue or to show a change in impedance due to a wound being opened up in morbid tissue. Conductivity sensors can include Ag/AgCl electrodes and an impedance analyser. The conductivity sensors can be used to measure the change of impedance of a region of wound growth by measuring the impedance of the surrounding tissue/area. In some embodiments, the sensor array can utilize conductivity sensors to measure the change in conductivity on perimeter electrodes due to a wound size or wound shape change. In some embodiments, the conductivity sensors can be used in the wound bed or on the perimeter of the wound.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some embodiments, the thermistors can be arranged in groups of five. Each thermistor is nominally 10 k$\Omega$, and each group of five has a common ground. There are five groups of thermistors, giving a total of 30 connections. In some embodiments, there can be nine conductivity terminals. Each conductivity terminal requires one connection, giving a total of 9 connections. In some embodiments, there can be five SpO2 sensors. Each SpO2 sensor requires three connections, plus power and ground (these are covered separately), giving a total of 15 connections. In some embodiments, there can be 10 color sensors. Each color sensor comprises an RGB LED and an RGB photodiode. Each color sensor requires six connections, however five of these are common to every sensor, giving a total of 15 connections. Power and ground are considered separately. In some embodiments, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some embodiments, the sensor array can include 25 thermistor (Murata NCP15WB473E03RC), 9 conductivity terminal, 5 SpO2 (ADPD144RI), 10 RGB LED (such as KPTF-1616RGBC-13), 10 RGB Color Sensor, 10 FET, a printed circuit board (PCB), and an assembly.

As described herein, a control module can be used to interface with the sensor array. Controller 24 can include one or more of the following features. In some embodiments, the control module can contain a power source, such as batteries, and electronics to drive the sensors. The control module can also log data at appropriate intervals and allow data transfer to an external computing device, such as a personal computer (PC) as shown in FIG. 1A. The control module can be customized to have various features depending on the sensors used in the sensor array and the data collected by the sensors. In some embodiments, the control module can be comfortable enough and small enough to be worn continuously for several weeks. In some embodiments, the control module can be positioned near the wound dressing or on the wound dressing. In some embodiments, the control module can be positioned in a remote location from the wound dressing and accompanying sensor array. The control module can communicate with the sensor array and wound dressing through electrical wires or through wireless communication whether positioned on the dressing, near the dressing, or remote from the wound dressing. In some embodiments, the control module can be adapted to be utilized with different sensor arrays and can enable easy replacement of the sensor array.

In some embodiments, the control module can include various requirements and combination of features including but not limited to the features listed in Table 1 below.

TABLE 1

OPTIONAL FEATURES FOR CONTROL MODULE 7 day operation from a single set of batteries
28 day local, non-volatile, storage capacity
Easy to charge, or to replace battery TABLE 1-continued

OPTIONAL FEATURES FOR CONTROL MODULE

Figure 4E:
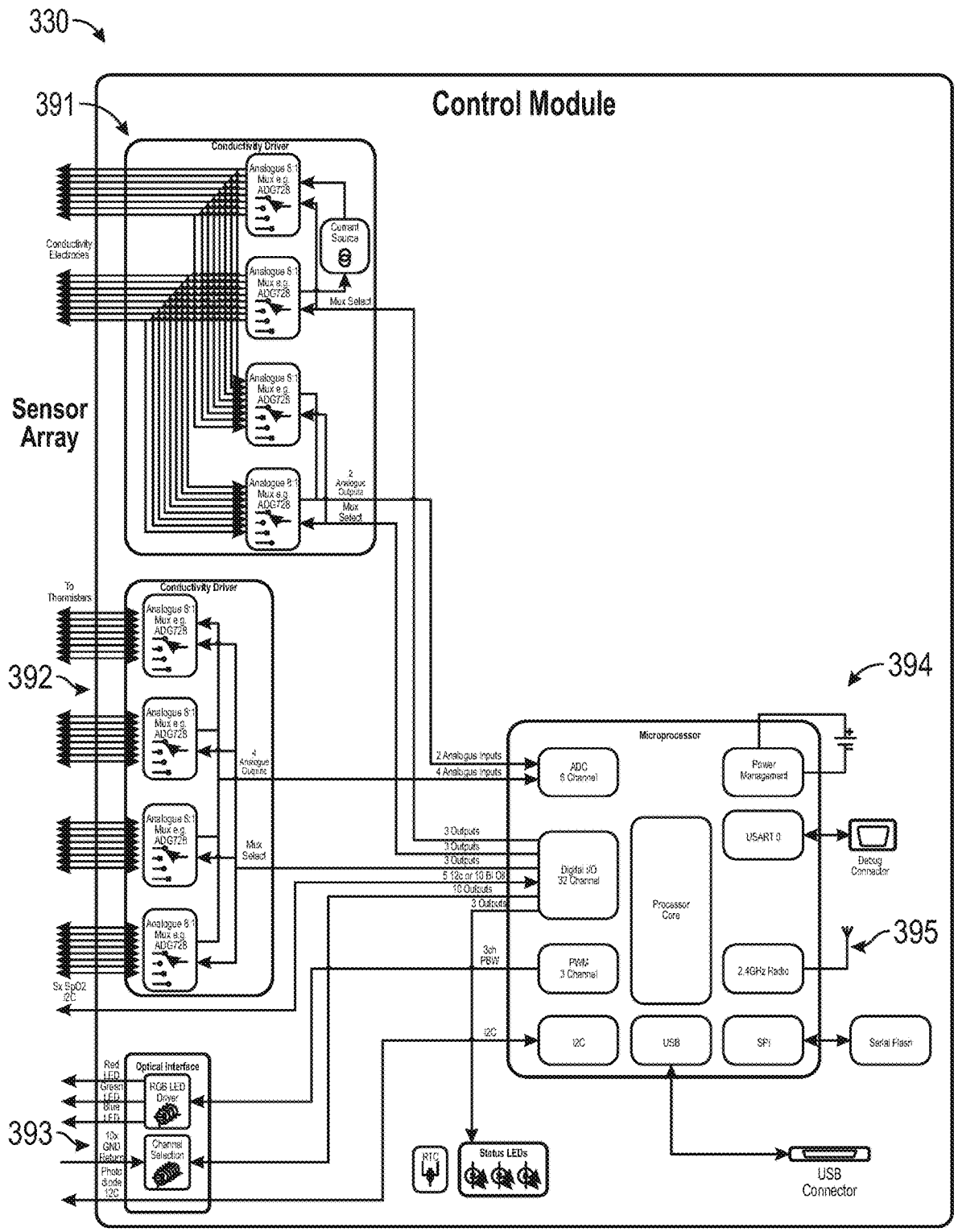
FIG. 4E illustrates a control module according to some embodiments.

Wireless link to PC/tablet (such as Bluetooth)
Wired link to PC (optional, micro-USB)
Drive electronics for thermistors
Drive electronics for conductivity sensors
Drive electronics for optical sensors
Drive electronics for SpO2 sensors
Power management
Real Time Clock (RTC) to allow accurate data logging, and correlation with other measurands
Ability to change sample rates and intervals (useful for SpO2) for each sensor
Indication of status via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low FIG. 4E illustrates a block diagram 330 of a control module according to some embodiments. Controller 24 can include one or more of the illustrated and described features. The block diagram of the control module includes a conductivity driver box 391 displaying features of the conductivity driver. Box 392 shows the features of the thermistor interface and box 393 shows the features of the optical interface. The control module can include a controller or microprocessor with features similar to those shown in box 394. Real time clock (RTC), Status LEDs, USB connector, Serial Flash, and Debug Connector can be included as features of the control module as shown in FIG. 4E.

In some embodiments, the microprocessor can have one or more of the following features: 2.4 GHz or another suitable frequency radio 395 (either integrated, or external) with a suitable antenna or antennas; Supplied Bluetooth software stack; SPI interface; USB (or UART for external USB driver); I2C; 3 channel PWM; 32 GPIO; or 6-channel ADC. In some embodiments, the device can require at least 48 I/O pins or possibly more due to banking limitations. Bluetooth stack typically requires ~20 kB on-board Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

In some embodiment, the control module can include a memory component where the amount of local storage depends on the sample rate and resolution of the sensors. For example, an estimated data requirement of 256 Mb (32 MB) can be met by using a serial Flash device from a number of manufacturers (Micron, Spansion).

The control module can utilize one or more analogue switches. In some embodiments, analogue switches with good on resistance and reasonable bandwidth can be used. For example, Analog Devices' ADG72 or NXP's NX3L4051HR can be used. Based on the initial system architecture, 8 of these will be required.

The control module can incorporate a power source, such as a battery. For example a 300mWh/day battery can be used. For 7 days this is 2100mWh. This could be provided by: a 10 days, non-rechargeable, ER14250 (14.5 mm diameter×25 mm) LiSOCl2 cell; or a 7 days, rechargeable, Li 14500 (14.5 mm diameter×500 mm) Li-Ion.

The control module can incorporate a real time clock (RTC). The RTC can be chosen from any RTC devices with crystal. The control module can also include miscellaneous resistors, capacitors, connectors, charge controllers, and other power supplies.

The PCB of the control module can be a 4-layer board, approximately 50 mm×20 mm, or 25 mm×40 mm. The type of PCB used can be largely driven by connection requirements to sensor array.

The enclosure of the control module can be a two part moulding, with clip features to allow easy access for changing sensor arrays or batteries.

The data collected through the sensor array can be passed through the control module and processed by host software. The software may be executed on a computing or processing device (see FIG. 1A). The processing device can be a PC, tablet, smartphone, or other computer capable of running host software. The processing device executing the software can be in communication with the control module through electrical wires or through wireless communication. In some embodiments, the software may be configured to provide access to the data held on the control module, but not to perform big-data analysis. The host software can include an interface to the control module via Bluetooth or USB. In some embodiments, the host software can read the status of control module, download logged data from control module, upload sample rate control to control module, convert data from control module into format suitable for processing by big-data analysis engine, or upload data to cloud (see FIG. 1A) for processing by analysis engine.

The software may be developed for PC (Windows/Linux), tablet or smartphone (Android/iOS), or for multiple platforms.

Additional embodiments of wound dressing with sensors and other related systems are disclosed in International Application No. PCT/IB2017/000693, filed on May 12, 2017, titled SENSOR ENABLED WOUND MONITORING AND THERAPY APPARATUS, the disclosure of which is hereby incorporated by reference in its entirety.

In some embodiments, a source of negative pressure (such as a pump) and some or all other components of the topical negative pressure system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the topical negative pressure system.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Component Positioning in Sensor Enabled Wound Dressing

In some embodiments, electrical or electronic components, such as sensors, connections, or the like, can be placed or positioned on or embedded in one or more wound dressing components, which can be placed in or on the wound, skin, or both the wound and the skin. For example, one or more electronic components can be positioned on a substrate side that faces the wound, such as the lower surface 224 of the wound contact layer 222 in FIG. 2B. The substrate can be flexible, elastic, or stretchable or substantially flexible, elastic, or stretchable in order to conform to or cover the wound. For example, the wound contact layer can be made from a stretchable or substantially stretchable material, such as one or more of polyurethane, thermoplastic polyurethane (TPU), silicone, polycarbonate, polyethylene, polyimide, polyamide, polyester, polyethelene tetraphthalate (PET), polybutalene tetraphthalate (PBT), polyethylene naphthalate (PEN), polyetherimide (PEI), along with various fluoropolymers (FEP) and copolymers, or another suitable material. In some instances, one or more electronic components can be alternatively or additionally placed or positioned on or embedded in any one or more of a transmission layer, absorbent layer, backing layer, or any other suitable layer of the wound dressing.

In some implementations, while it may be desirable for the wound contact layer to be stretchable to better conform to or cover the wound, at least some of the electronic components may not be stretchable or flexible. In such instances, undesirable or excessive localized strain or stress may be exerted on the one or more electronic components, such as on the supporting area or mountings of an electronic component, when the wound is dressed with the wound dressing and the wound contact layer is positioned in or over the wound. For example, such stress can be due to patient movement, changes in the shape or size of the wound (such as, due to its healing), or the like. Such stress may cause movement, dislodgment, or malfunction of the one or more electronic components (for example, creation of an open circuit from a pin or another connector becoming disconnected). Alternatively or additionally, it may be desirable to maintain the position of one or more electronic components, such as one or more sensors, in the same or substantially same location or region on the wound contact layer with respect to the wound (such as, in contact with the wound) so that measurements collected by the one or more electronic components accurately capture changes over time in the same or substantially same location or region of the wound. While the surface of the stretchable wound contact layer may move when, for example, the patient moves, it may be desirable to have the one or more electronic components be located in the same location or region with respect to the wound.

In some embodiments, one or more stiff, rigid, or non-stretchable or substantially stiff, rigid, or non-stretchable regions, such as one or more regions of non-stretchable or substantially non-stretchable material, can be mounted, positioned, or placed on the wound contact layer (or another suitable wound dressing component) for supporting one or more electronic components. Mounting, positioning, or placing one or more electronic components in the one or more non-stretchable or substantially non-stretchable regions can prevent formation of localized stress or assist with maintenance of the position of the one or more electronic components with respect to the wound. In some instances, one or more electronic components can be alternatively or additionally be flexible, such as mounted or printed on or supported by one or more flexible materials. For example, flexible plastic sheets or substrates, such as polyimide, polyether ether ketone (PEEK), polyester, silicone, or the like, can be used.

Component Arrangement in Sensor Enabled Wound Dressing

Various layouts or arrangements of sensor enabled wound dressings are contemplated, for example, as illustrated in FIGS. 5A-5J as well as illustrated and described elsewhere the present disclosure. Any of the wound dressings illustrated in FIGS. 5A-5J can be disposable. Component arrangements described below (or elsewhere in this disclosure) are not limited to being positioned on a wound dressing. In some implementations, the components can be arranged on another dressing, structure, or substrate or could be provided separately for being positioned over any wound, as broadly defined herein. Component arrangements can be used for one or more of preventing or treating a wound.

Figure 5B:
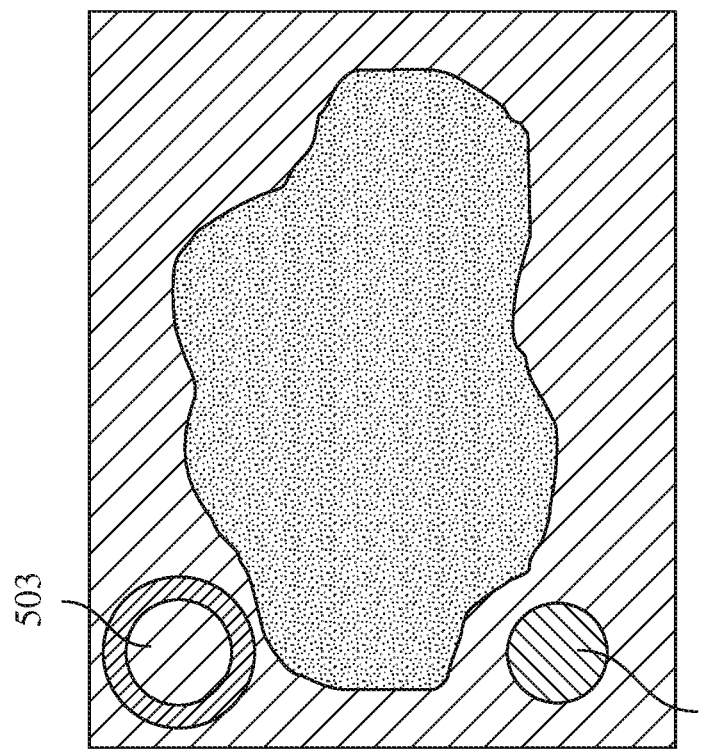
Figure 5A:
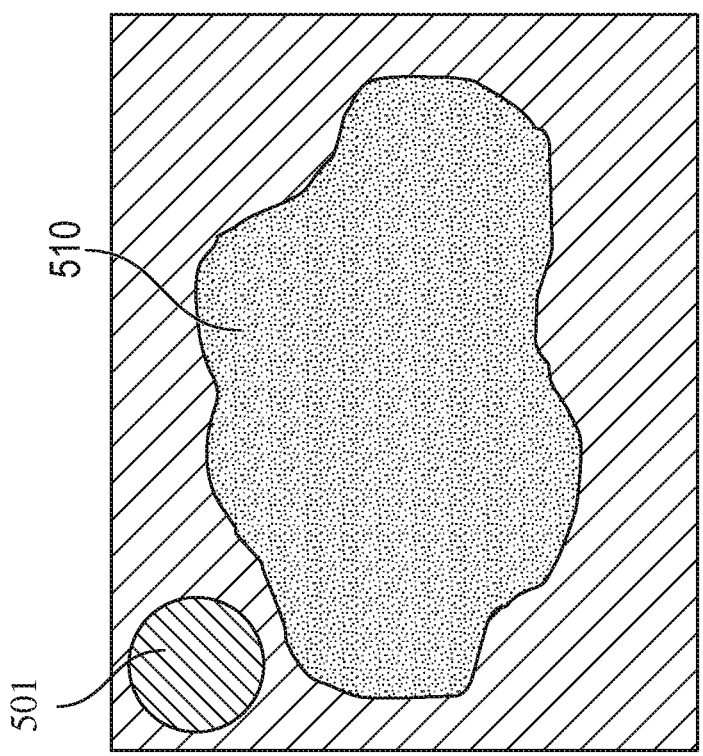

FIG. 5A illustrates a sensor enabled wound dressing that includes a power source 501, such as a battery, positioned in or on the dressing according to some embodiments. In this and other embodiments described herein, outline 510 represents contours of a wound. FIG. 5B illustrates a sensor enabled wound dressing that includes a power source and a charger, such as a coil 503, configured to recharge the power source according to some embodiments. For example, power can be transmitted to the charger wirelessly or via a wire in order to recharge the power source 501. For instance, power can be transmitted wirelessly, such as via inductive coupling, capacitive coupling, magnetodynamic coupling, far field transmission, or the like. As another example, energy harvesting can be additionally or alternatively utilized for recharging the power source 501. The power source 501 and charger in FIG. 5B are positioned on or in the dressing. In some implementations, the illustrated coil 503 can function as an antenna for transmitting and/or receiving data wirelessly.

Figure 5D:
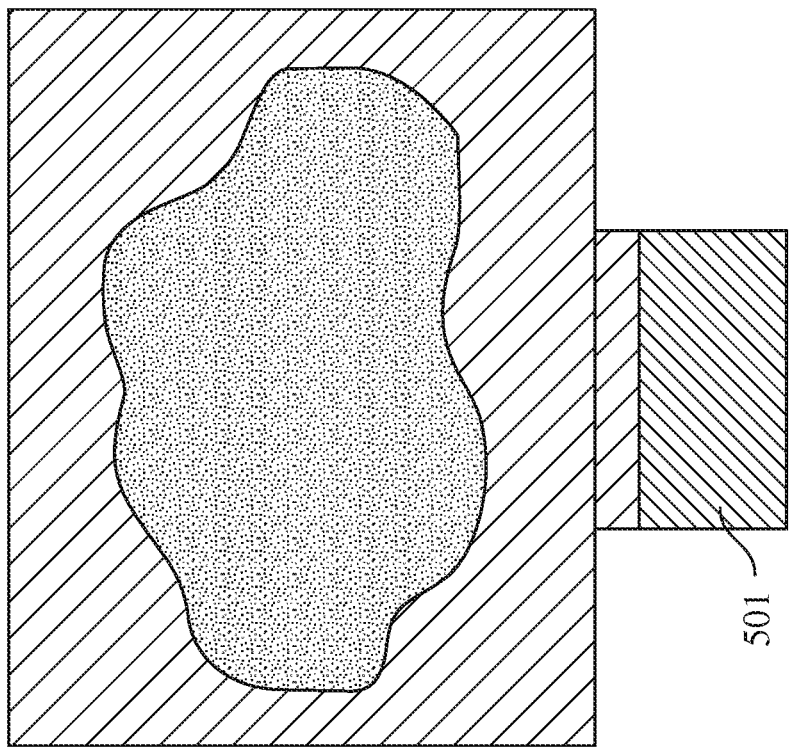
Figure 5C:
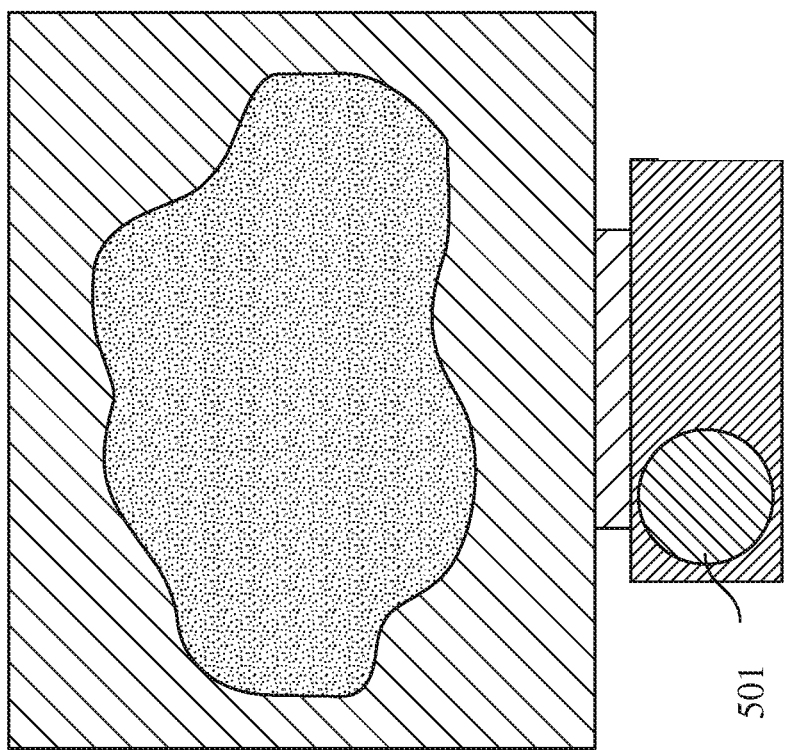

FIG. 5C illustrates a sensor enabled wound dressing configured to be connected to a reusable controller, such as the controller 24, according to some embodiments. The controller includes a power source 501, such as a battery. The power source 501 can be rechargeable. FIG. 5D illustrates a reusable sensor enabled wound dressing configured to be connected to a power source 501, such as a battery, located outside the dressing according to some embodiments. The illustrated power source 501 can be rechargeable or replaceable.

Figure 5F:
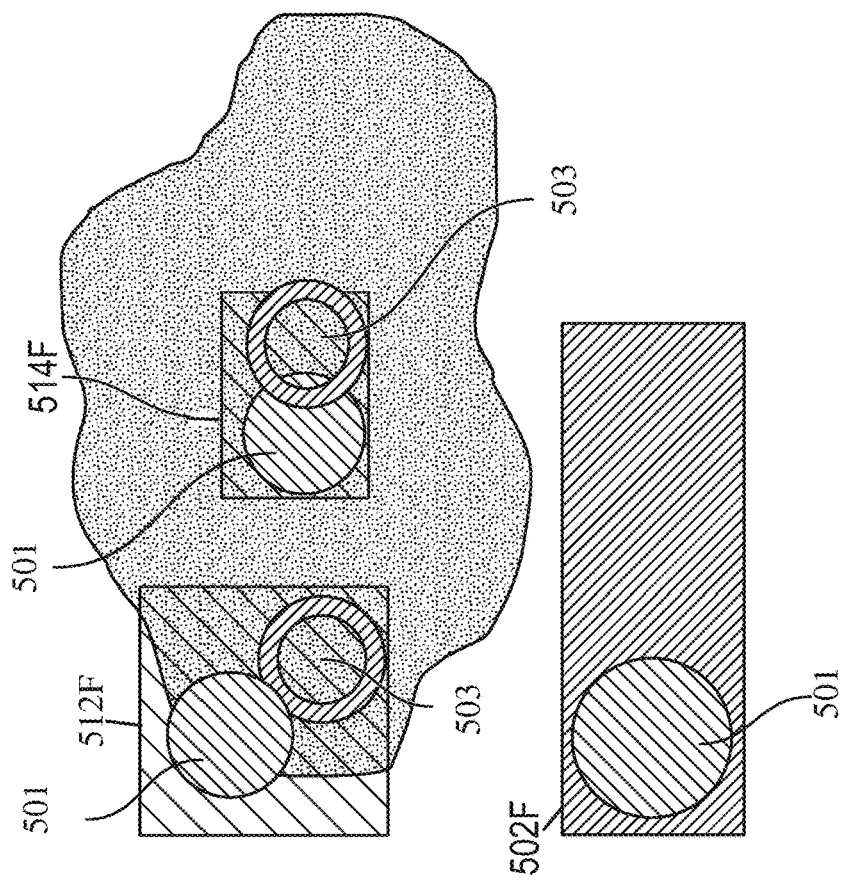
Figure 5E:
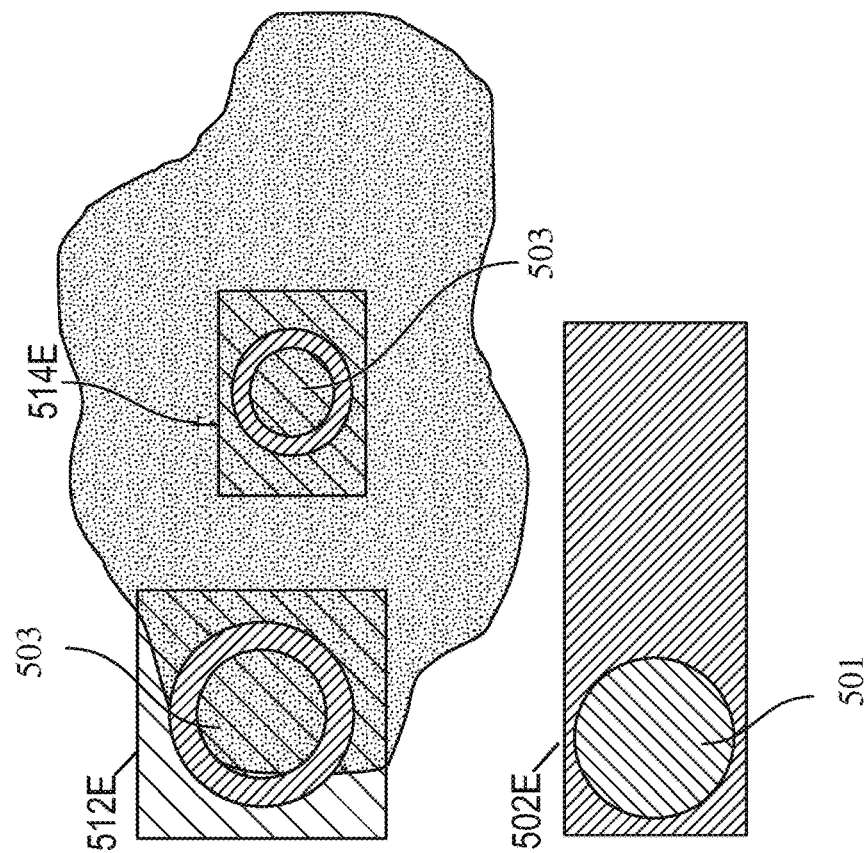

FIG. 5E illustrates a sensor enabled wound dressing that includes one or more sensors 512E or 514E positioned on or in the dressing according to some embodiments. Also illustrated is a controller 502E that is separate from the wound dressing according to some embodiments. The controller 502E can be configured to wirelessly transmit power (such as, from illustrated power source 501) to the one or more sensors 512E or 514E using any of the techniques described herein. For example, the one or more sensors 512E or 514E can each include a coil 503 for inductive coupling. The one or more sensors 512E or 514E may not include a power source 501. In certain implementations, one or more of the illustrated coils can function as an antenna for transmitting and/or receiving data wirelessly. In some implementations, the controller 502E can be positioned in or on the wound dressing.

FIG. 5F illustrates a sensor enabled wound dressing that includes one or more sensors 512F or 514F positioned on or in the dressing and a controller 502F according to some embodiments. Unlike the arrangement in FIG. 5E, the one or more sensors 512F or 514F include a power source 501, which can be recharged through wireless power transmission from the controller 502F as described herein. As is illustrated, the controller 502F is separate from the wound dressing. In certain implementations, one or more of the illustrated coils 503 can function as an antenna for transmitting and/or receiving data wirelessly. In some implementations, the controller 502F can be positioned in or on the wound dressing.

Figure 5H:
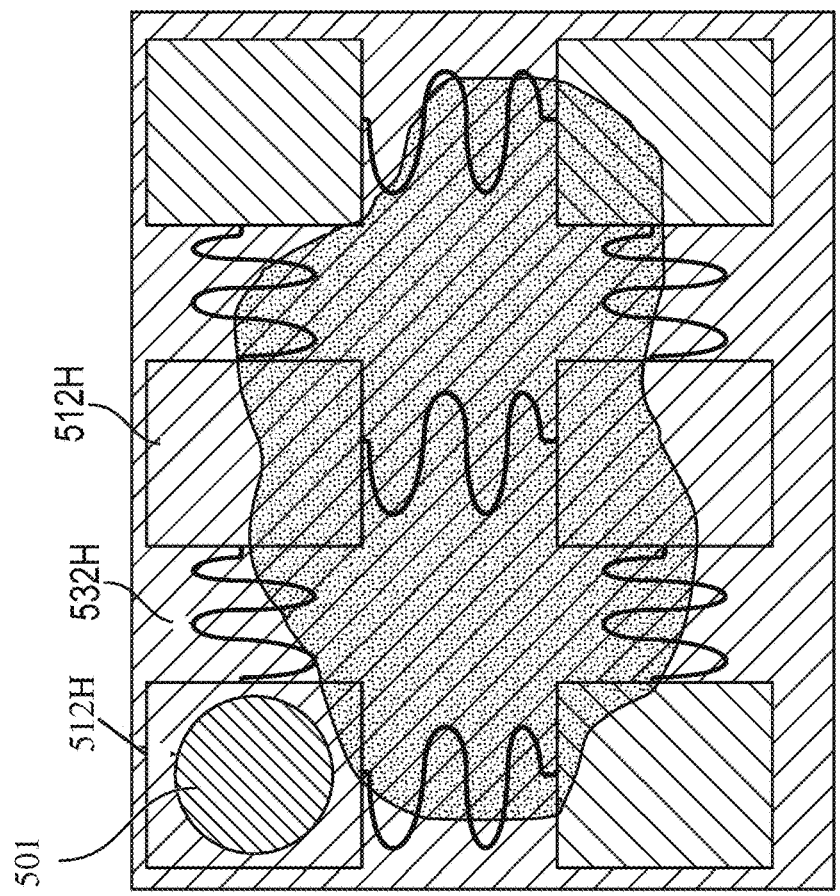
Figure 5G:
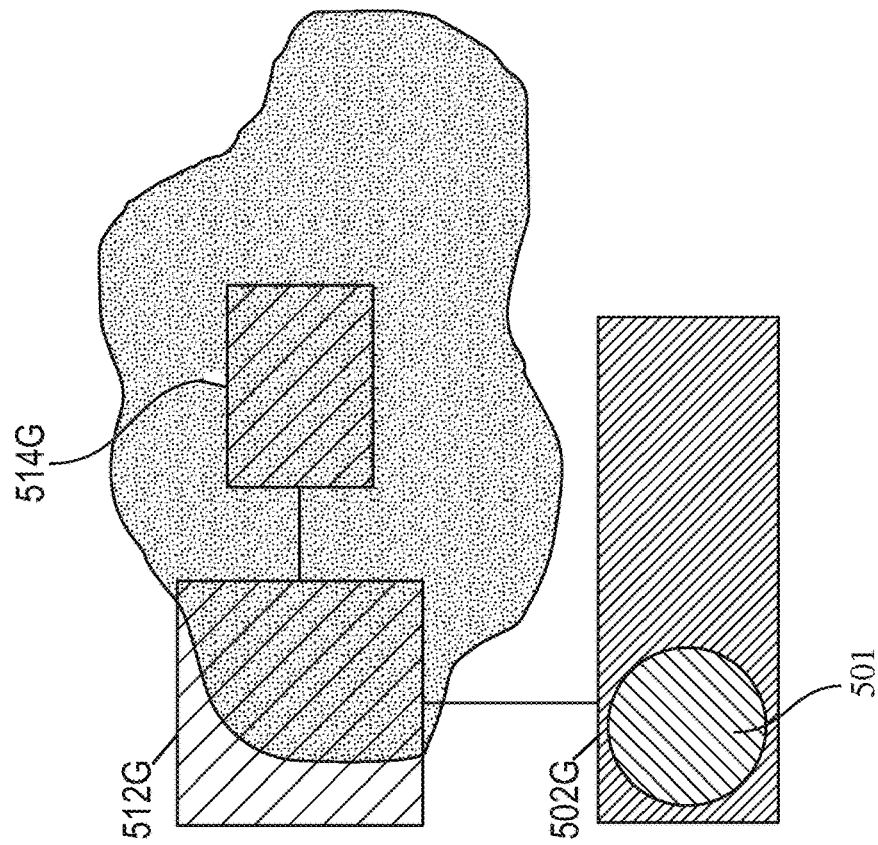

FIG. 5G illustrates a sensor enabled wound dressing that includes one or more sensors 512G or 514G positioned on or in the dressing and a controller 502G according to some embodiments. Unlike the arrangement in FIGS. 5E-5F, the one or more sensors 512G or 514G are connected to the controller 502G via one or more wires. The controller 502G can include a power source 501, which can be rechargeable or replaceable. In some cases, the one or more sensors 512G or 514G can be flexible or stretchable. For example, the one or more sensors 512G or 514G can be positioned on a flexible or stretchable substrate, such as TPU. In some cases, the one or more sensors 512G or 514G may not be flexible or stretchable. For example, the one or more sensors 512G or 514G can be positioned on a non-stretchable substrate, such as PET or Polyimide. As is illustrated, the controller 502G is separate from the wound dressing. In some implementations, the controller 502G can be positioned in or on the wound dressing. In certain implementations, one or more antennas can be positioned in or on the wound dressing or on the controller 502G for transmitting and/or receiving data wirelessly.

FIG. 5H illustrates a sensor enabled wound dressing that includes one or more sensors 512H and a power source 501, both positioned on or in the dressing, according to some embodiments. The power source 501 can be a rechargeable or replaceable power source as described herein. The power source 501 provides power to the one or more sensors 512H via one or more flexible or stretchable connections or tracks 532H. The one or more connections 532H can in addition or alternatively communicate data between the one or more sensors 512H. The one or more connections 532H can be mounted or positioned on stretchable material, such as PET or another stretchable material described herein. In some implementations, the one or more sensors 512H can incorporate components or tracks positioned on a non-stretchable substrate (as described herein). In certain implementations, the stretchable material that can be positioned (such as, being co-planar) between the non-stretchable substrates of the one or more sensors 512H. In some cases, the stretchable material that can be positioned as a laminated or partially or fully encapsulating layer.

FIG. 5I illustrates a sensor enabled wound dressing configured to be fluidically connected to a negative pressure wound therapy device 542I according to some embodiments. Device 542I is separate from the wound dressing and includes a power source 501 and a negative pressure source, such as a pump 505, configured to provide negative pressure to a wound. Power can be transmitted to the wound dressing from the device 542I as described herein. Electrical wiring and negative pressure connection(s) can be coaxial, with parallel axes, or the wiring can be spirally wrapped around the negative pressure connection(s). Wiring can be manufactured within the extrusion of the negative pressure connection(s), which can include one or more channels for transmission of gas and/or fluid. FIG. 5J illustrates a sensor enabled wound dressing that includes a power source 501 and a negative pressure source in or on the dressing.

In some implementations, any of the embodiments illustrated in FIGS. 5A-5J can be combined with any one or more of the other illustrated embodiments. For example, sensor enabled wound dressing illustrated in FIG. 5B can be combined with the sensor enabled wound dressing illustrated in FIG. 5H. Such combination will include a charger positioned on or in the dressing. As another example, sensor enabled wound dressing illustrated in FIG. 5H can be combined with the sensor enabled wound dressing illustrated in FIG. 5J. Such combination will include a negative pressure source positioned in or on the dressing.

In some embodiments, a rechargeable energy source, such as one or more of a super capacitor or electric double layer capacitor (EDLC), can be positioned in or on the dressing. Prior to deployment on a patient, the dressing can be stored without any power. The rechargeable energy source of the dressing can be charged prior to positioning the dressing on the patient. Such charging can be performed wirelessly. One or more indications can be provided to indicate that the power source has been charged. Power source can be charged via one or more energy harvesting techniques.

In some implementations, a super capacitor can be alternatively or additionally used for wireless communications. Wireless communication circuitry can operate more effectively, such as in terms of range and efficiency for one or more of transmission or reception, when powered by a pre-charged super capacitor. This can be due to, for example, lower internal resistance of a super capacitor that allows the super capacitor to supply high bursts of constricted current more efficiently than a battery.

Integrated Sensor Enabled Wound Dressing

In some embodiments, a sensor enabled wound dressing can be configured to operate without a separate controller, such as the controller 24 or any other controller described herein. Instead, an integrated wound dressing can include one or more electronic components of the controller, such as processor(s), antenna(s), power source(s), or the like positioned in or on the wound dressing, such as on a wound contact layer. An integrated wound dressing may not include a connector, such as the connector 28 or any other connector described herein. Some of the advantages of not including a separate controller and connector can include reduced risk of fluid ingress into the separate controller through the connector, reduced electromagnetic interference, noise, user error on connection, arcing (for example, as a result of separation of connections or traces to a level that cannot be achieved with a small connector), foreign (for example, conductive) object or material intrusion, or the like that may be introduced via the connector, or the like. One or more of these advantages can be achieved while also minimizing the size or weight of the system and/or removing a potentially non-flexible connecting element.

Although the arrangements of electronic components, including sensors and processors, are described in connection with positioning on a wound dressing, the arrangements described below (or elsewhere in this disclosure) are not limited to being positioned on a wound dressing. In some implementations, the components can be arranged on another dressing, structure, or substrate or could be provided separately for being positioned over any wound, as broadly defined herein. Component arrangements can be used for one or more of preventing or treating a wound.

Figure 6:
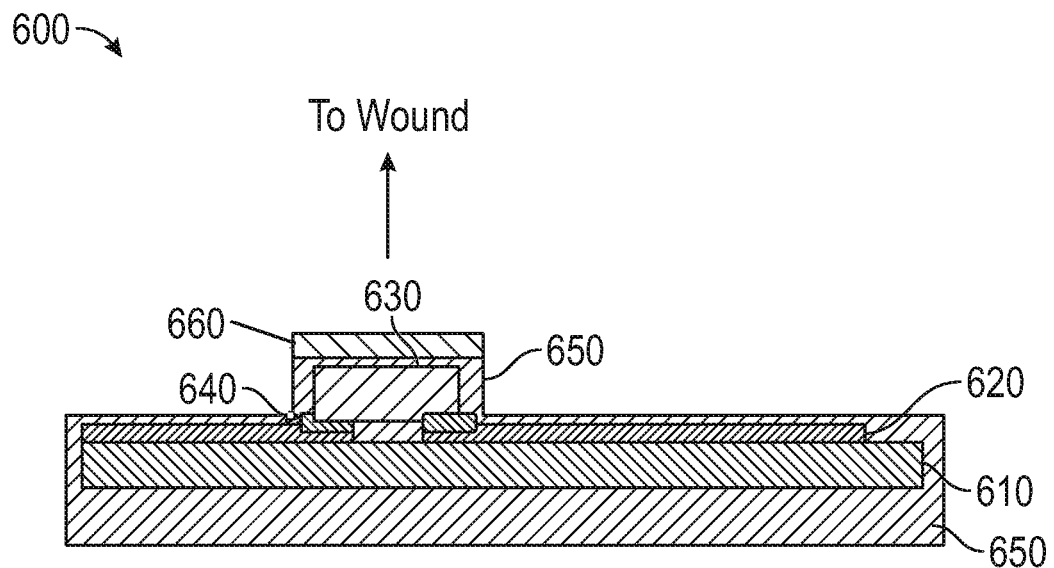
FIG. 6 illustrates an integrated sensor enabled wound dressing according to some embodiments.

FIG. 6 illustrates an integrated sensor enabled wound dressing 600 according to some embodiments. The dressing includes a substrate 610, which can be substantially flexible as described herein. The substrate 610 supports one or more electronic modules or components 630 and one or more electronic connections 620 as described herein. The one or more electronic components can be sensors, processors, power sources, or the like. The one or more electronic components can be connected to the one or more tracks via one or more connectors 640. Connectors 640 can be pins, leads, bumps, surface mounts (SMT), or the like. Additionally or alternatively a socket can be used to support and electronically connect the electronic components.

Electronic connections or tracks 620 can be tracks printed on the substrate 610, such as using conductive copper, conductive ink (such as silver ink, silver/silver chloride ink, copper ink, graphite ink, carbon ink, dielectric ink, etc.), or the like. At least some of the electronic connections 620 can be flexible or stretchable or substantially flexible or stretchable. Connectors 640 can be configured to electronically connect the electronic components 630 to the electronic connection 620 (as illustrated in FIG. 6), which in turn can be connected to other electronic modules (not shown) positioned on the substrate 610, on or in other components of the wound dressing, or external to the wound dressing.

One or more of the substrate 610, electronic components, or electronic connections can be partially or fully encapsulated with coating 650. Coating 650 can be conformal coating configured to coat or encapsulate one or more of the substrate 610 or components supported by the substrate, such as the electronic connections 620 or the electronic components 630. Coating 650 can provide biocompatibility, shield or protect the electronics from coming into contact with fluids, or the like. Coating 650 can be hydrophobic. As used herein, hydrophobic can encompass substantially preventing ingress of fluids, including water. Coating 650 can be one or more of a suitable polymer, adhesive, such as Dymax 1165 or 1072-M UV, light, or thermal curable or cured adhesive, Optimax adhesive (such as, NovaChem Optimax 8002-LV), parylene (such as, Parylene C), silicon, epoxy, urethane, acrylated urethane, or another suitable biocompatible and stretchable material. As used herein, biocompatible can mean being in compliance with one or more applicable standards, such as ISO 10993 or USP Class VI. Coating 650 can be thin, such as about 100 microns thick, less than about 100 microns thick, or more than about 100 microns thick. Coating 650 can be applied and cured using one or more of UV, light, or thermal curing. In some implementations, coating 650 can be applied on the other side of the substrate 610 (or side facing away from the wound) to the components particularly if the substrate is not impermeable to fluid. In some embodiments, coating 650 is optional.

The wound dressing 610 can also include one or more adhesive pads, tracks, or regions 660 applied to a wound facing side of the substrate 610 or the wound facing side of the coating 650. Adhesive material can be one or more of silicone, such as two-part silicone, one-part silicone, gel, epoxy, acrylic-based material, or another suitable material. Adhesive can be applied and cured using one or more of UV, light, or thermal curing. For example, adhesive can be printed, sprayed, coated, or the like and then cured by UV, light, thermal curing, catalytic, water vapor, or the like. In some embodiments, adhesive is optional.

In some embodiments, one or more adhesive regions 660 can be patterned to position or affix specific components in particular areas, regions, or locations in contact with or relative to the wound even while the substrate 610 is under stress or strain. While the substrate may strain between the adhesive regions, the electronic component 630, such as a sensor, will remain in the same location in contact with or relative to the wound (due to the adhesive region), thus maintaining the most repeatable measurement. Additionally, the connectors 640 of the electronic component 630 will not be put under as much stress because the body (for instance, the skin, which may strain about 20%) will relieve some of the stress (for example, due to the attachment of the wound contact layer to the wound by the one or more adhesive regions) and the substrate 610 will yield around the electronic module. Similar stress relief can be provided to one or more electronic connections 620 which can be overlaid by one or more adhesive regions. Any or all of the one or more adhesive regions 660 can be positioned on the coating 650, between the coating 650 and the substrate 610, between the one or more components 620 and the substrate 610 (such as to affix the one or more components to the substrate), or between the one or more components 620 and the coating 650.

Additional details of construction of the wound dressing, including conformal coating, adhesive regions, and non-stretchable regions, are described in International Patent Application No. PCT/EP2018/059333 titled COMPONENT STRESS RELIEF FOR SENSOR ENABLED NEGATIVE PRESSURE WOUND THERAPY DRESSINGS, filed on 11 Apr. 2018, which claims the benefit of U.S. Provisional Patent Application Nos. 62/484,316 titled COMPONENT STRESS RELIEF FOR SENSOR ENABLED NEGATIVE PRESSURE WOUND THERAPY DRESSINGS, filed on 11 Apr. 2017, 62/484,321 titled COMPONENT STRESS RELIEF FOR SENSOR ENABLED NEGATIVE PRESSURE WOUND THERAPY DRESSINGS, filed on 11 Apr. 2017, and 62/524,564 titled COMPONENT POSITIONING AND STRESS RELIEF FOR SENSOR ENABLED NEGATIVE PRESSURE WOUND THERAPY DRESSINGS, filed on 25 Jun. 2017 and International Patent Application No. PCT/EP2018/069883 titled BIOCOMPATIBLE ENCAPSULATION AND COMPONENT STRESS RELIEF FOR SENSOR ENABLED NEGATIVE PRESSURE WOUND THERAPY DRESSINGS, filed on 23 Jul. 2018, each of which is incorporated by reference in its entirety.

The one or more electronic components 630 can be configured to continue to operate properly even under stress or strain to which the substrate 610 may be subjected when the wound dressing 600 is positioned on a patient. Taking an example of an electronic component, a processor (such as, an application specific integrated circuit (ASIC)), the processor can include or be packaged on a "slivered" or very thin silicon wafer suitable for positioning on a wound contact layer that will be placed on a patient's wound. It may be advantageous to use a thin processor so as to not cause discomfort or pain to the patient. A thin wafer could be flexed when the wound contact layer is subjected to stress or strain, which can cause the wafer to break or otherwise malfunction thereby leading to the processor to not operate correctly. Silicon can be resilient or strong under compression, but brittle or weak under tension, such as when being bent. For example, the bend radius of a thin silicon wafer can be about 5 mm or more.

In some implementations, one or more electronic components 630 can be formed at least partially from reinforced material. For example, tension areas of a wafer under bending can be decreased by subjecting to or putting an electronic components, such as the wafer, under compression, which can be referred to as pre-straining. In some implementations, the wafer can be pre-strained, such as by applying compression to the wafer before positioning it on the substrate 610 or after positioning it on the substrate. In the latter case, a portion of or the entire substrate 610 can be compressed. The substrate can be slightly compressed prior to placement of the wafer. Wafer can be compressed and subsequently relaxed. Compression can be applied mechanically. In some cases, the substrate can be stretched prior to placement of the wafer. Stretching can be performed mechanically. After the wafer has been placed on the substrate, the substrate can be relaxed, which can apply compression to the wafer.

In certain embodiments, one or more of conformal coating (such as, the coating 650) or adhesive (such as, the adhesive 660) can apply compression to the wafer when being applied to the substrate. For example, the coating (or adhesive) material can shrink when cured using any of the processes described herein, thereby applying compression to the substrate or wafer.

In some cases, compression can be applied with a film. Film can be stretched and applied to the substrate or wafer. As described herein, the film can be applied to the substrate before the wafer is placed on the substrate, to the wafer before it is placed on the substrate, or the substrate and/or wafer after the wafer is placed on the substrate. Contraction of the film can cause the substrate or wafer to be compressed. Shrink wrap film can be applied to the substrate or the wafer, which causes compression of the substrate or wafer. In some cases, film can be shrunk by curing (instead of or in addition to stretching).

Pre-strained wafer can have improved resilience when subjected to stress or strain. Using the analogy of reinforced concrete, the wafer can be analogous to the concrete and one or more of the substrate, coating, or adhesive can be analogous to steel that reinforces the concrete.

The foregoing description is applicable to any electronic component that can be positioned on the substrate 610. For example, in some cases, at least some electronic components 630 can be positioned on a circuit board (such as, a printed circuit board (PCB) or printed circuit board assembly (PCBA)). The circuit board can include one or more connections between one or more electronic components positioned on the circuit board. The circuit board can be pre-strained as described herein so that it continues to operate properly even under stress or strain.

Additionally or alternatively, in some embodiments, one or more electronic components 630 include or are packaged on a flexible or substantially flexible substrate. For example, such substrate can be formed from one or more of PET, PEN, or Polyimide.

In some implementations, an integrated sensor enabled wound dressing includes one or more power sources configured to power one or more electronic components. As described herein in connection with electronic components, it may be advantageous to reduce the thickness of one or more components of the one or more power sources for positioning on a wound contact layer that will be placed on a patient's wound. For example, button or coin cell batteries, foil capsule batteries, paper batteries, flexible lithium batteries, lithium ceramic batteries, lithium polymer batteries, or the like can have significant thickness dedicated to a shell (in case of coin cell battery) or another structure that does not directly impact storage capacity. In case of a coin cell battery, for instance, capacity of the battery may go down significantly when the thickness of the shell is being reduced. The capacity of the battery may go down disproportionally quickly as the size of the cell enclosure is reduced because thickness of enclosure occupies a greater portion of the overall volume and cannot be reduced proportionally to the other elements of the battery. Similarly, in case of a paper battery, a significant portion of the thickness (such as, 300 to 400 μm or more) can be dedicated to components that do not provide any storage capacity.

In some embodiments, thickness of the one or more power sources can be reduced by positioning one or more power source components, such as battery chemistry or chemicals, directly on a substrate (such as, the substantially flexible wound contact layer) or one or more electronic connections. No separate case or enclosure may be necessary, which can reduce the thickness of the one or more power sources and allow for increase (or decrease) in capacity by increasing (or decreasing) the size of the power source components.

FIGS. 7A-7D illustrate power source integration in sensor enabled wound dressing 700 according to some embodiments. Wound dressing 700 includes a substrate 710 (which can include a wound contact layer as described herein), one or more electronic connections 715, one or more electronic components 732 positioned on one or more connectors 740 as explained in connection with FIG. 6. Power source (for example, battery) component 720 can be positioned on an electronic connection 715 as illustrated. In some implementations, the component 720 can be a cathode electrode as described herein. For example, the component 720 can be printed directly on the electronic connection using any of the techniques described herein. The entire component 720 can be positioned on the electronic connection. For example, the dimensions of the component 720, such as the width and height, can be smaller than or correspond to the dimensions of the electronic connection, such as the width and height. This can advantageously reduce or minimize the thickness of the power source. In some implementations, one or more power source components can alternatively or additionally positioned on the substrate 710.

Figure 7A:
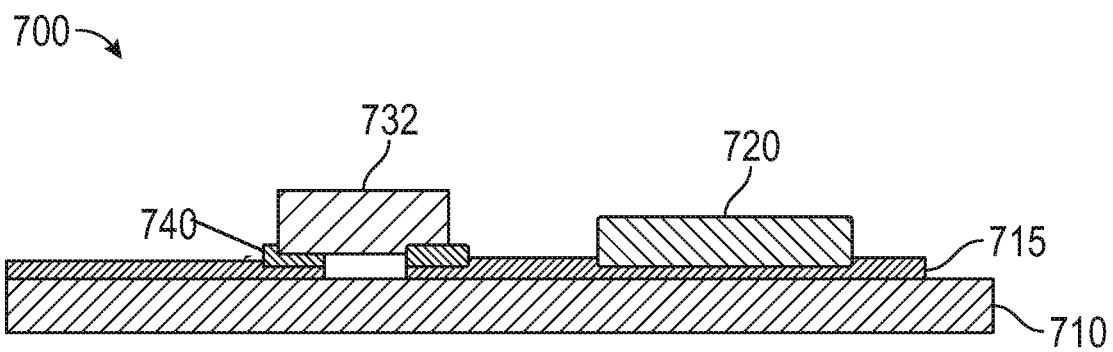
FIGS. 7A-7D and FIG. 8 illustrate power source integration in sensor enabled wound dressings according to some embodiments.
Figure 7B:
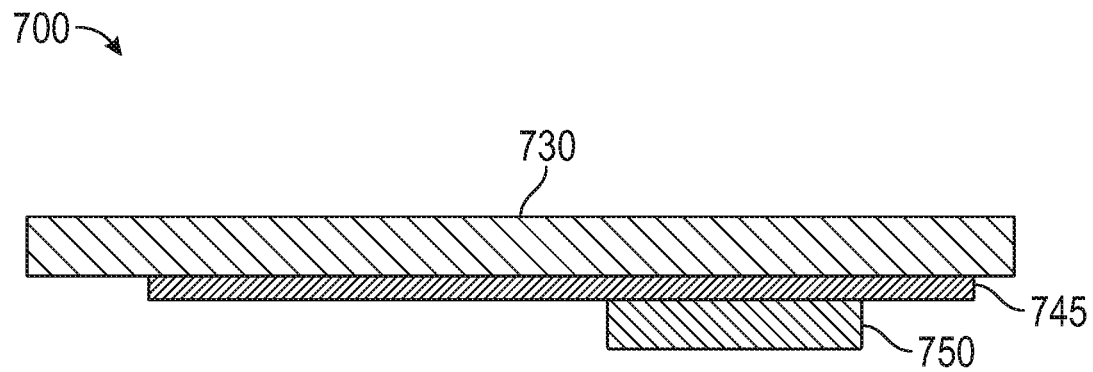

As described herein, in certain implementations, a wound contact layer can include a top portion 730 and bottom portion 710. As illustrated in FIG. 7B, the wound dressing 700 can include the top portion 730, an electronic connection 745, and a power source (for example, battery) component 750 positioned on the electronic connection. For example, the component 750 can be printed directly on the electronic connection using any of the techniques described herein. Connection 745 can be an anode of the power source, which can be connected to one or more electronic components to supply power. In some implementations, one or more power source components can alternatively or additionally positioned on the top portion 730, which can be film In some implementations, as described herein, a wound may be sealed by a film positioned above the substrate, and the layer 730 can be film.

In some embodiments, power source components 750 and 720 can form an integrated power source when the top portion 730 is positioned over the bottom portion 710 of the wound contact layer. For example, component 750 can be positioned directly or substantially directly above component 720. In some cases, one or more dielectric or insulating materials can be positioned between the two components 750 and 720 so that a power source is formed.

Figure 7C:
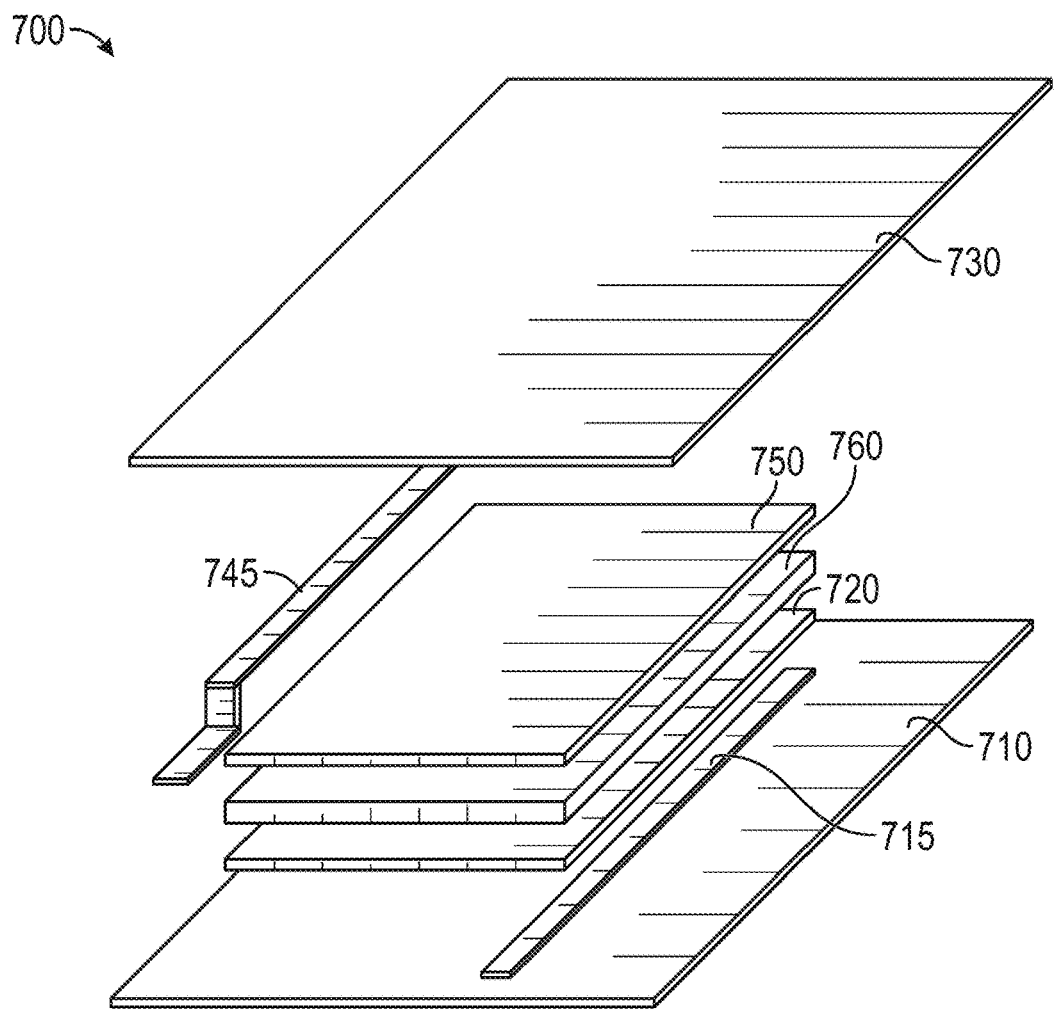
Figure 7D:
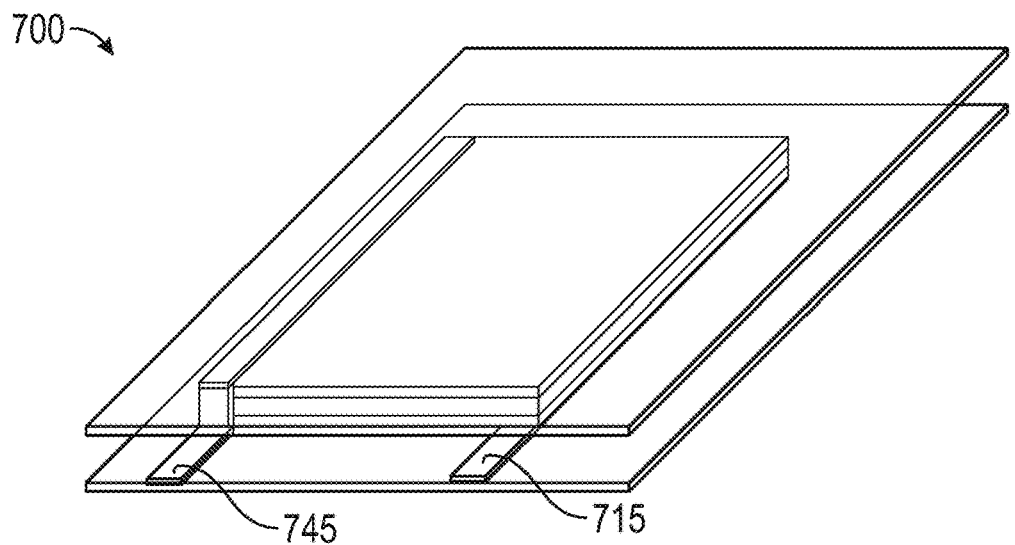

FIG. 7C illustrates an exploded view of the dressing 700 with the top portion 730 of the substrate positioned over the bottom portion 710 of the substrate. Power source components 750 and 720, which can respectively correspond to an anode and cathode of the power source (or vice versa) are illustrated as stacked over one another. Electrolyte material 760 is positioned between the components 750 and 720 to permit generation of power. Connections or electrodes 745 (connected to the power source component 750) and 715 (connected to the power source component 720) can be used to deliver power to one or more electronic components positioned in or on the dressing, as described herein. FIG. 7D illustrates assembled view of the dressing 700 showing the electrodes 745 and 715 configured to deliver power supplied by the integrated power source. In some implementations, multiple pairs of power source components can be utilized. Power source components can be protected from fluid or other substances by being sandwiched between the portions of the substrate and, in some cases, encapsulated in coating as described herein.

Figure 8:
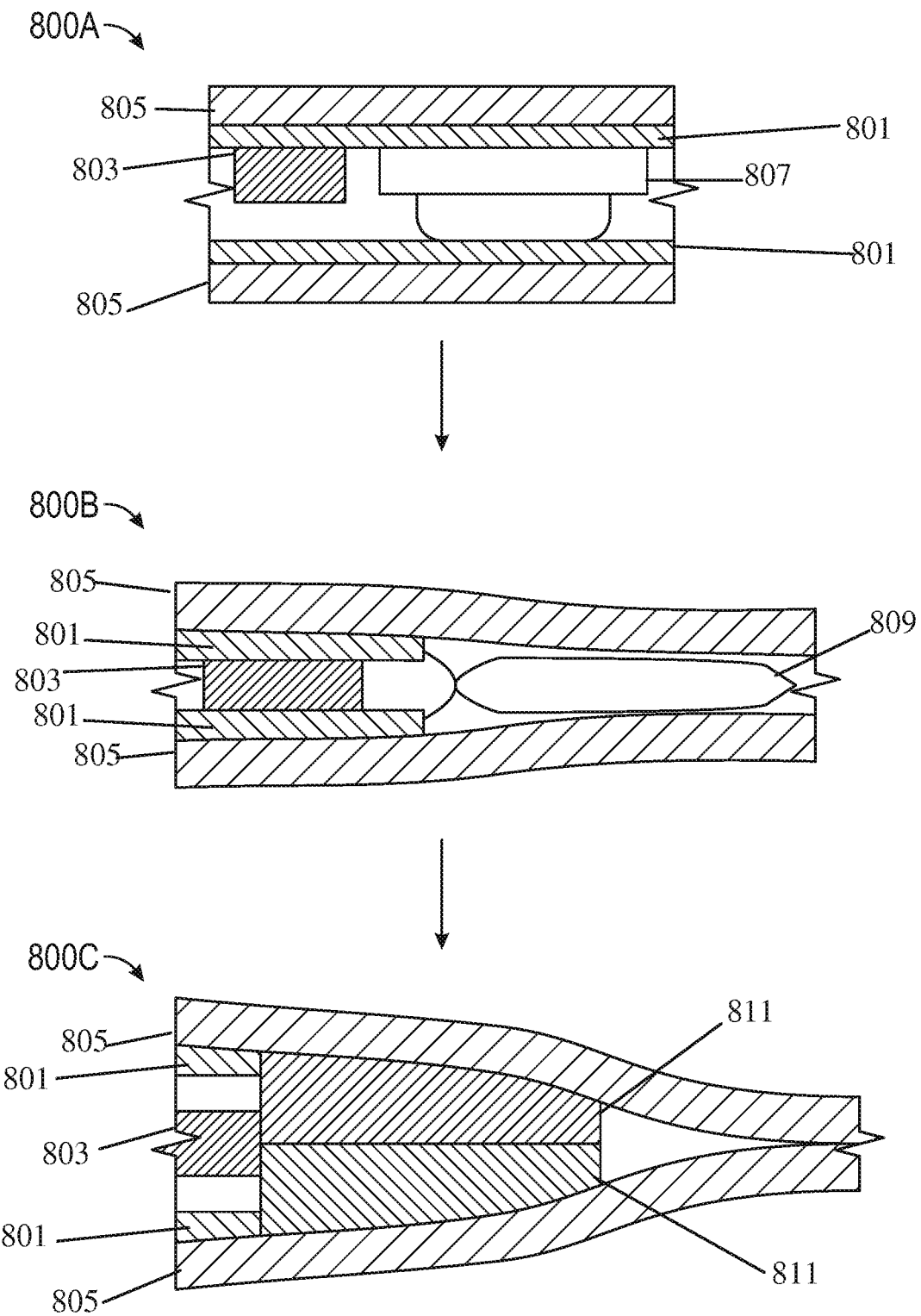

FIG. 8 illustrates power source integration in a sensor enabled wound dressing according to some embodiments. Schematic 800A illustrates integration of a button or coin cell battery 807 with two electrodes 801 (for example, cathode and anode), insulating material 803 positioned between the electrodes, and coating or encapsulant 805 surrounding the battery 807 and electrodes 801. Schematic 800B illustrates integration of a foil capsule or paper battery 809 with two electrodes 801 (for example, positive and ground), insulating material 803 positioned between the electrodes, and coating or encapsulant 805 surrounding the battery 809 and electrodes 801. Schematic 800C illustrates integration of a power source (such as, a battery) illustrated in FIGS. 7A-7D. Also shown are two electrodes 801 (for example, cathode and anode), insulating material 803 positioned between the electrodes, and coating or encapsulant 805 surrounding the battery chemistry 811 and electrodes 801. The battery in schematic 800C can be thinner than the batteries 807, 809 in schematics 800A and 800B. This can be possible at least partly because the battery chemistry 811 is stacked as described herein.

Figure 9:
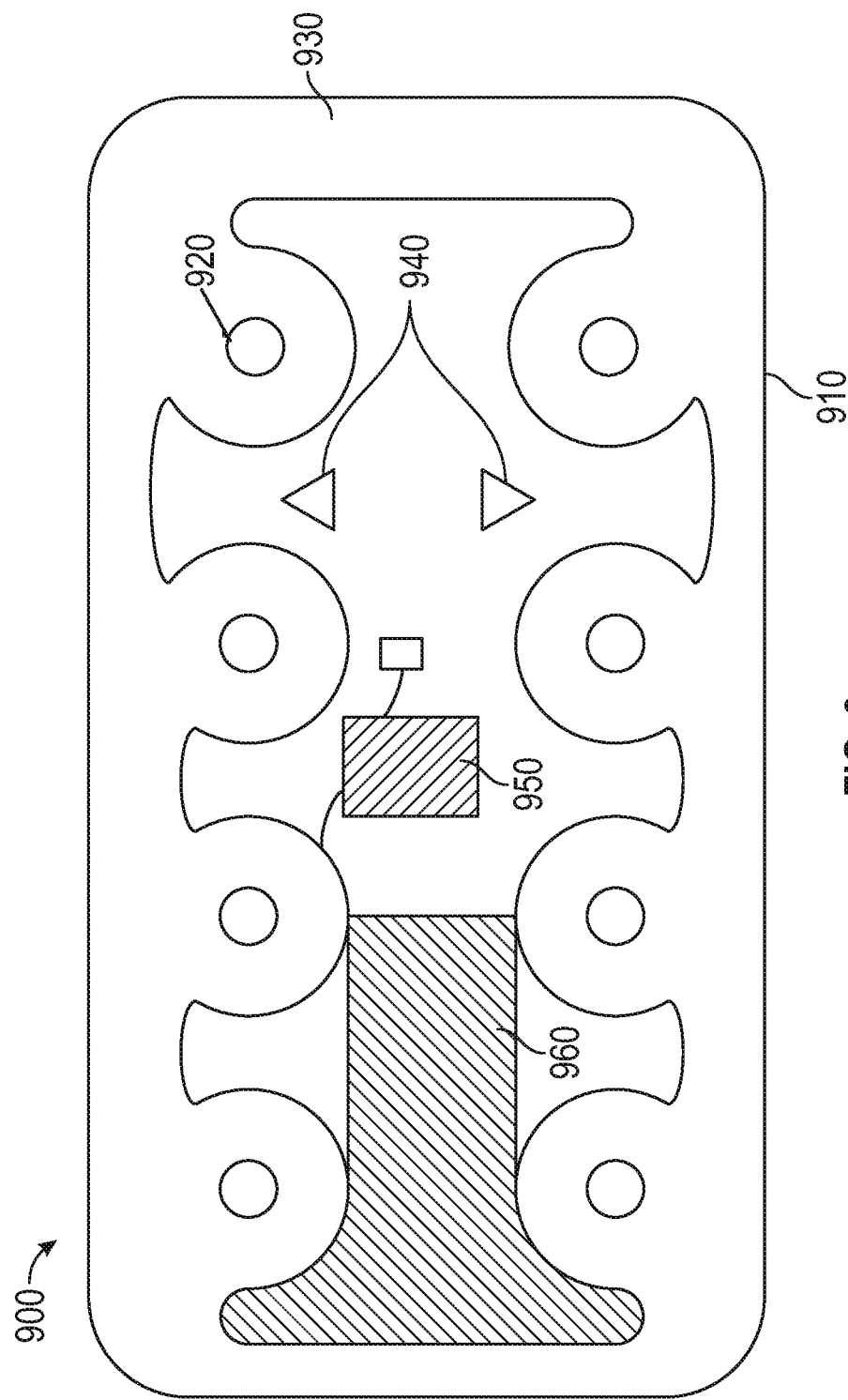
FIG. 9 illustrates an integrated sensor enabled wound dressing according to some embodiments.

FIG. 9 illustrates an integrated sensor enabled wound dressing 900 with a power source according to some embodiments. The wound dressing 900 includes a substantially flexible wound contact layer 910 as described herein. The wound contact layer 910 includes a plurality of perforations 920 configured to allow fluid, such as wound exudate, to pass through the wound contact layer for removal from the wound. The wound contact layer 910 includes a plurality of sensors 940 and a controller or processor 950, such as an ASIC, as described herein. The wound contact layer 910 includes a ground plane 930 that serves as a return path for current from the processor 950. Power and ground of one or more sensors can be isolated from the primary power and ground plane in order to isolate digital, analog, and/or patient contact paths for noise and safety purposes. The wound contact layer 910 includes a cathode electrode for a power source, such as the battery, as described herein. One or both of the ground electrode 960 or the ground plane 930 can be printed on the wound contact layer using any of the techniques described herein.

As described herein, in some embodiments, an integrated sensor enabled wound dressing can include one or more antennas configured to communicate data, such as measurements obtained by the sensors. The one or more antennas can include inductive coil(s) configured to receive power for recharging the power source(s) of the wound dressing. The one or more antennas can be printed on the wound contact layer as described herein.

In some embodiments, an integrated sensor enabled wound dressing can be initialized or activated using one or more of the following mechanisms. Activation can include activating a controller of the wound dressing in certain implementations. Controller can be activated by causing an electrical connection to be provided between two or more terminals of an electronic circuit. For example, the wound dressing can be flexed to activate the electronic circuit. As another example, a pull tab, switch, or another mechanism can be provided. Removing the pull tab can cause the electronic circuit to be activated by removing insulation or providing conductive material (such as, spreading silver ink or another conductive material) to create an electrical connection between the terminals. As yet another example, a bubble or another container with conductive material can be popped or burst, which would cause conductive material (such as, silver ink or another conductive material) to activate the circuit by providing an electrical connection between the terminals.

As yet another example, an active circuit element, such as transistor, can operate as a switch that provides electrical connection between the terminals. The active circuit element can be turned on (or placed into conductive mode of operation) by applying external electric field. For example, a gate of transistor can be charged through a capacitive connection thereby turning the transistor on. As yet another example, an external magnetic field can be used to activate a magnetic switch, such as reed switch. As yet another example, a cap or similar mechanism can be burst or snapped to exert pressure on a piezoelectric switch that can generate an electric signal to provide electrical connection between the terminals.

Enclosure for Electronic Components

In some implementations, one or more of at least some of the electronic components or at least some electronic connections of a sensor enabled wound dressing can be enclosed in an enclosure. Doing so can help protect the components or connections from fluid, reduce electromagnetic interference (EMI), protect against electrostatic discharge (ESD), including defibrillation pulses, or the like.

Figure 10:
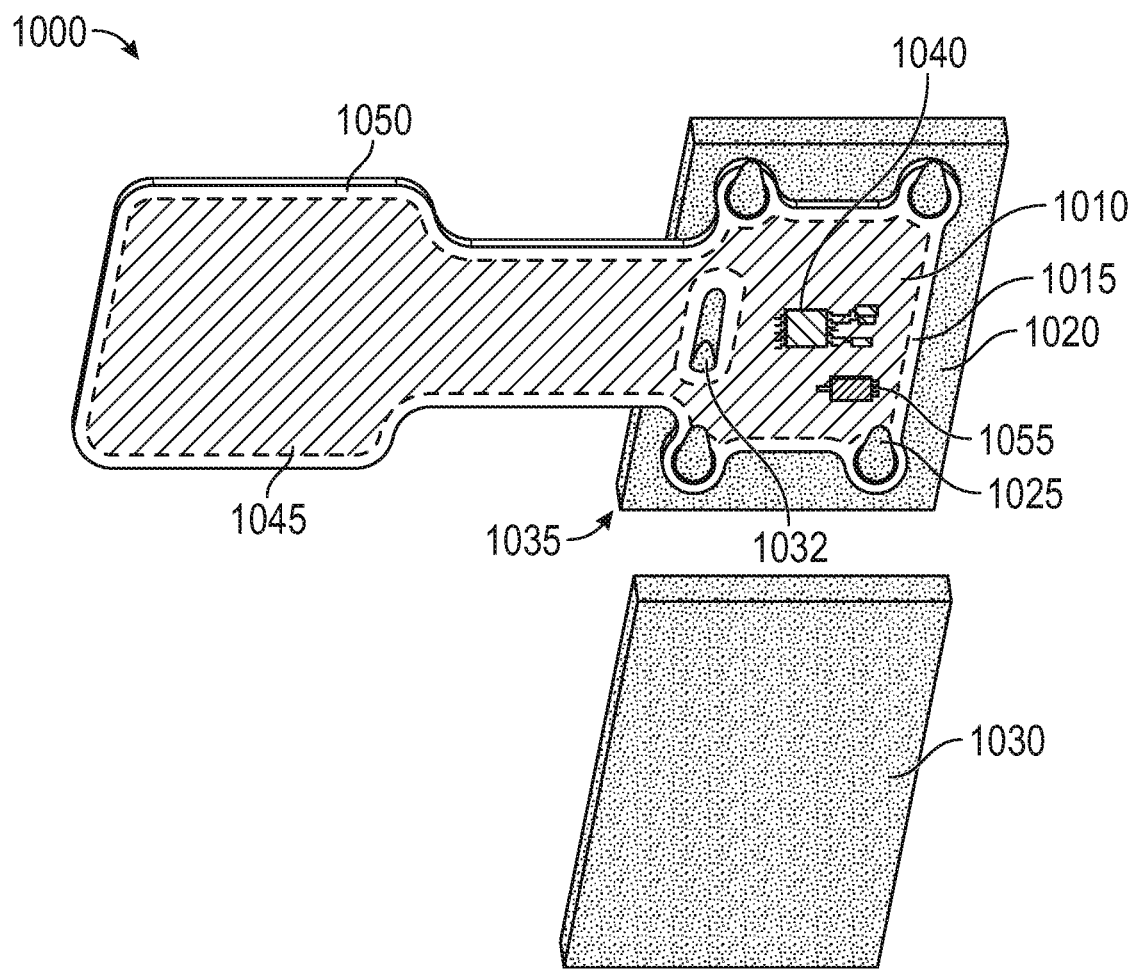
FIG. 10 illustrates a sensor enabled wound dressing with an enclosure according to some embodiments.

FIG. 10 illustrates a sensor enabled wound dressing 1000 with a housing or an enclosure according to some embodiments. The dressing include a controller 1015 with a circuit board 1010 that includes electronic components and connections 1040 and a power source 1055. The circuit board 1010 can be flexible or substantially flexible as described herein. The circuit board 1010 can be positioned on a bottom enclosure 1020, which can support the circuit board. Pins 1025 or other supporting elements or mechanisms, such as tabs, screws, recesses, etc. are positioned on the bottom enclosure 1020 to enable top enclosure 1030 to enclose at least a portion of the circuit board 1010 including the electronic components and connections 1040 and power source 1055. Top enclosure 1030 is configured to be supported by the pins 1025 when positioned over the bottom enclosure 1020 as directed by arrow 1035. Latch or lock 1032 or another closure mechanism is positioned on the bottom enclosure 1020 to retain in place or remove the top enclosure 1030. Such design can reduce effect of any EMI on the circuit board components enclosed in the enclosure. Pins can be made of non-conductive material. Any ESD through the pins 1025 of the enclosure may not arc against the circuit board components. In some cases, metal components (such as, metal screws) may be omitted to reduce the risk of arcing.

The dressing 1000 includes an area or portion 1045 supporting one or more sensors configured to obtain measurement of one or more of a wound or periwound as described herein. Dressing portion 1045 can include a substantially flexible wound contact layer as described herein. The wound contact layer can be separated from the circuit board 1010 by a distance 1050, which can help to protect the electronic components, connections, and the like from any EMI, electrosurgical spikes, defibrillation pulses or the like to which the wound contact layer may be subjected when positioned on a wound.

The enclosure can be designed to be small and light so as to be less obtrusive to a patient. Alternatively or additionally, such enclosure can reduce or minimize any pulling force on a wound contact layer, thereby reducing discomfort or pain to the patient caused by movement of the enclosure. In some implementations, the enclosure can be positioned external to a wound. For example, an external controller, such as the controller 24, can be positioned in the enclosure.

Monitoring Changes in Impedance

Figure 11A:
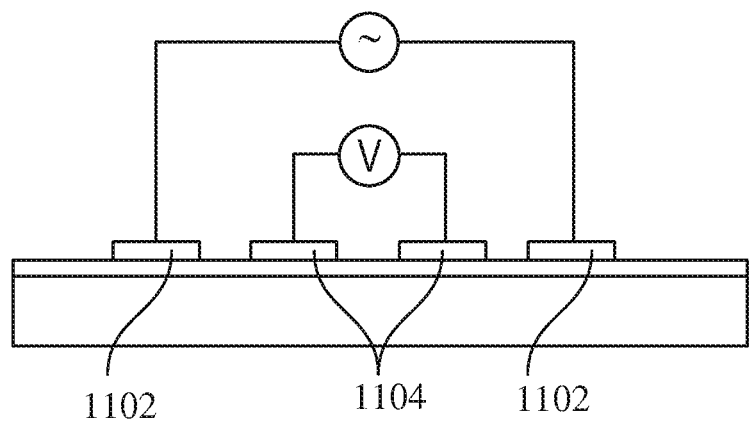
FIGS. 11A-11C illustrate electrical impedance measurements according to some embodiments.
Figure 11B:
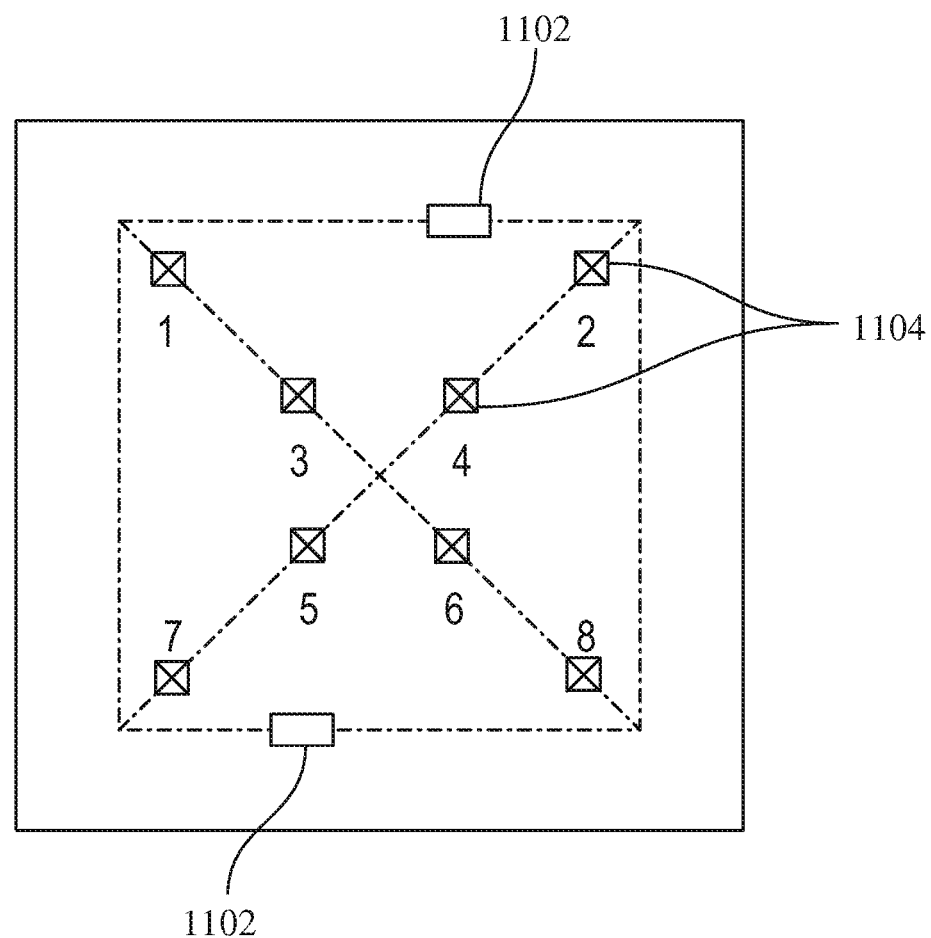

As disclosed herein, embodiments of a sensor enabled wound dressing, such as the wound dressing 22 of FIG. 1C, can measure one or more of impedance, temperature, light, or the like in relation to one or more of the wound or periwound. In some implementations, the sensors can be used to measure the change of impedance of a region of wound or periwound. For example, impedance measurement can be made utilizing a 4-point probe measurement as shown in FIG. 11A. A drive signal, such as AC drive signal, can be generated across excitation or drive circuits or pads 1102 and the voltage measurement can be made across separate measurement sensors or pads 1104. The pads can be positioned as illustrated in FIG. 11B. Eight measurement pads 1104 can be laid out as the corners of two concentric squares. The outer square can have approximately 80 mm side or any other suitable dimension. The inner square can have approximately 30 mm side or any other suitable dimension.

In some implementations, a complex voltage measurement can be taken as follows:

TABLE 1

Impedance measurement Between pads

| | |
|---|---|
| 1 | 2 |
| 1 | 3 |
| 1 | 7 |
| 2 | 4 |
| 2 | 8 |
| 3 | 4 |
| 3 | 5 |
| 3 | 6 |
| 4 | 5 |
| 4 | 6 |
| 5 | 6 |
| 5 | 7 |
| 6 | 8 |
| 7 | 8 |

Complex voltage measurement can identify the maximum and minimum voltages and the phase angle (or time) behind the drive signal. Additional details of impedance measurement are described in International Patent Application No. PCT/EP2018/069886, titled "Skewing Pads for Impedance Measurement," filed on 23 Jul. 2018, which claims the benefit of U.S. Provisional Patent Application No. 62/536,774, titled "Skewing Pads for Impedance Measurement," filed on 25 Jul. 2017, each of which is incorporated by reference in its entirety.

In some embodiments, impedance measurement is based on an AC measurement. An excitation signal can be coupled to the tissue capacitively through a sensor or pad with insulating coating. A second similar sensor or electrode can be placed some distance away and connected to ground. By applying an excitation signal, an AC current flows through the tissue between the sensors.

Second pair(s) of sensors or electrodes can be placed between the excitation electrodes, and can be used to sense voltage. These two electrodes can each be connected to one or more high impedance amplifiers, whose outputs can be fed to a differential amplifier. By measuring this output voltage, and dividing by the excitation current, the impedance between the measurement electrodes can be measured.

Figure 11C:
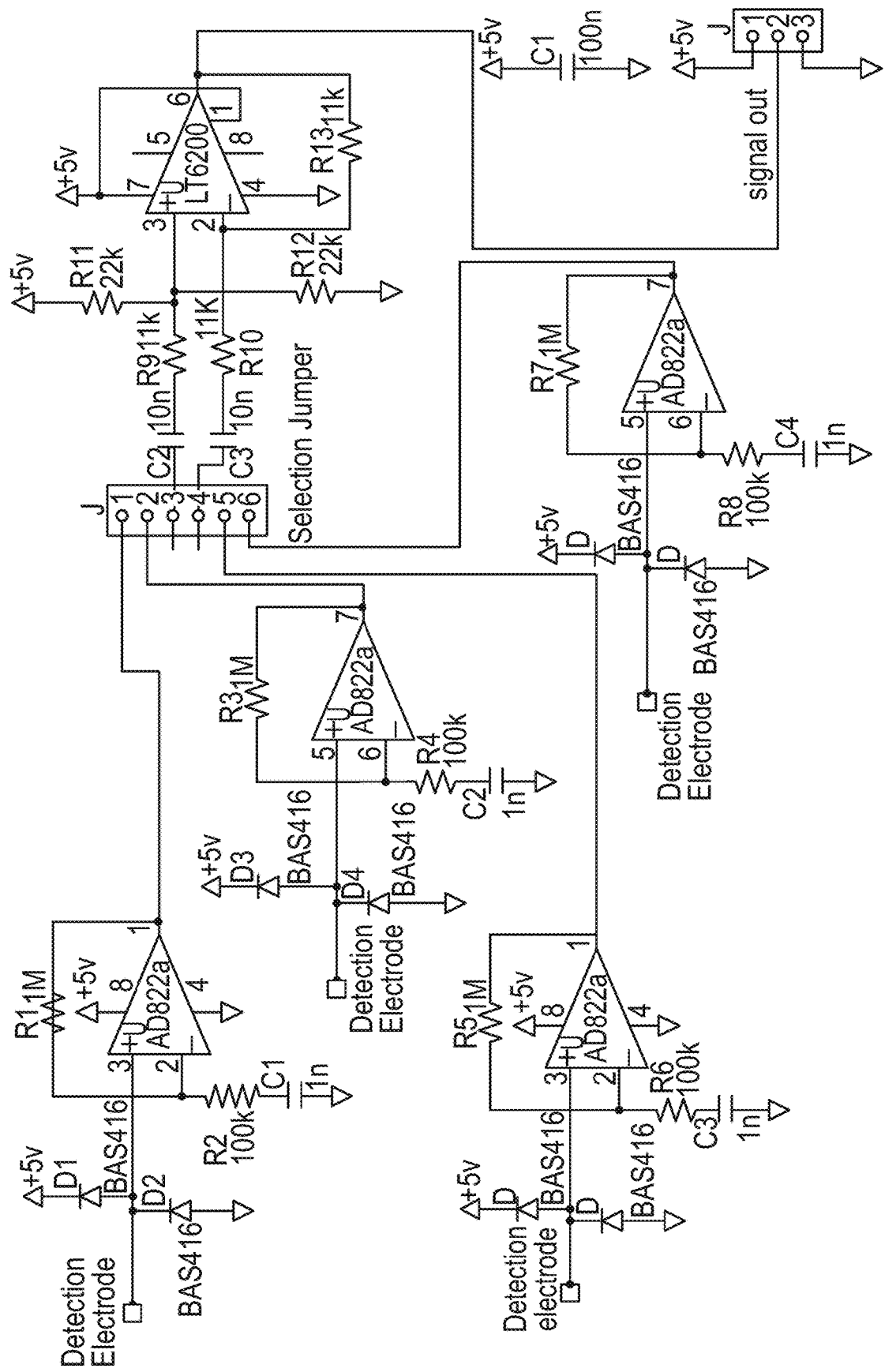

As is illustrated in FIG. 11C, voltage and current can be detected using a pair of lock-in amplifiers. As the measured impedance may be relatively high, particularly at the electrode to tissue junction, it may be advantageous that the measurement electrode amplifiers have high input impedance. First stage amplifiers can be chosen to have high input impedance. These can be configured as non-inverting amplifiers in order to take advantage of this high input impedance. The low-frequency gain can be rolled down using capacitors C1, C2, C3 or C4, as is illustrated in FIG. 11C.

In some cases, for single supply operation, the non-inverting input may need to be biased at mid-rail. The biasing may also need to provide a DC path for the input bias current of the op-amp. While this could be done using a resistive divider at the non-inverting input, it may lead to the following:

1. The bias network lowers the input impedance unless resistors of the order of the op-amp input impedance are used (and resistors of this value are impractically large).

2. Large bias resistors contribute a large thermal noise component which swamps the input noise voltage of the op-amp, reducing the overall signal-to-noise ratio.

In some embodiments, instead of using resistors, the input bias is achieved using a pair of reverse biased diodes D1, D2, D3, or D4 illustrated in FIG. 5C. The reverse biased diode presents a very high impedance (determined by the reverse leakage), without the high thermal noise contribution. Diode with a very low reverse leakage can be chosen. The reverse leakage also provides the DC path for the op-amp bias current.

In some embodiments, one or more measurements obtained by a sensor enabled wound dressing can be affected by noise or interference caused by straining, stretching, contracting, or tearing of the substantially flexible wound contact layer. For example, in case of impedance measurements, variations in the impedance or resistance of the electrical connections connecting the one or more sensors to one or more measurement circuits (such as, the circuits illustrated in FIG. 11C) can affect the overall measurement(s). In some cases, when an electrical connection is stretched within the limits of its elasticity (such that it does not break or permanently deform), it will become narrower and longer and its electrical resistance will increase. Conversely, when an electrical connection is compressed (such that it does not buckle), it will broaden and shorten and its electrical resistance will decrease. When the substantially flexible wound contact layer supporting a plurality of electrical connections is put under strain or stress (for example, due to patient movement), the impedance or resistance of the connections or components may change. As these changes in resistance can affect the measurements, including impedance measurements, it can be advantageous to monitor such changes in order to ensure accuracy as described herein.

Figure 12:
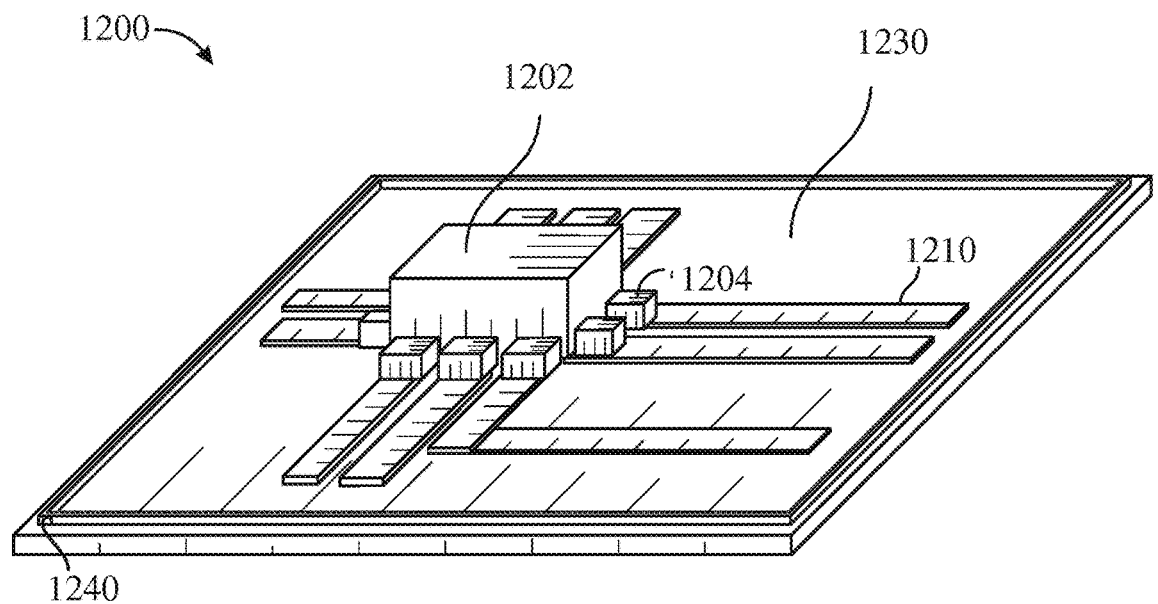
FIG. 12 illustrates a sensor enabled wound dressing configured to monitor changes in electrical impedance according to some embodiments.

FIG. 12 illustrates a sensor enabled wound dressing 1200 configured to monitor changes in the electrical impedance according to some embodiments. As is shown, a sheet or substrate 1230 supports one or more electronic components, including an electronic component or module 1202 with a plurality of connectors 1204 and a plurality of electronic connections 1210. The substrate 1230 can be a stretchable or substantially stretchable and can include a wound contact layer as described herein. The electronic module 1202 can be any electronic component described herein, such as a sensor, light source (such as an LED, impedance sensor, temperature sensor, etc.), controller or processor (such as a communication processor), or the like. Electronic connections 1210 can be tracks printed on the substrate 1230, such as using conductive copper, conductive ink (for example, silver ink, copper ink, graphite ink, etc.), or the like. At least some of the electronic connections 1210 can be flexible or stretchable or substantially flexible or stretchable. Connectors 1204 can be configured to electronically connect the electronic module 1202 to the electronic connection 1210 (as illustrated in FIG. 12), which in turn can be connected to other electronic modules (not shown) positioned on the substrate 1230, on or in other components of the wound dressing, or external to the wound dressing. Connectors 1204 can be pins, leads, bumps, or the like. Additionally or alternatively a socket can be used to support and electronically connect the electronic module 1202. As is used herein, printing material on a substrate can include one or more of laminating, adhering, or any other suitable technique.

As shown, the substrate 1230 can include a plurality of slits, holes, or perforations formed in the substrate 1230 according to some embodiments. The substrate 1230 can be perforated using one or more of a cold pin perforation, hot pin perforation, laser ablation perforation, ultrasonic or ultrasound perforation, or the like to make the wound contact layer permeable to liquid and gas. In some implementations, one or more utilized perforation processes can generate a flat or substantially substrate around the hole rather than an uneven surface (such as donut-shaped surface). Having a flat or substantially flat substrate can assist in generating a homogenous layer when bio compatible conformal coating is applied (such as, via spray, brush, pouring, or the like). Further, using a perforation process that leaves the surface of the substrate uneven or substantially uneven can introduce a greater risk of dislodging one or more components, such as the electronic connections 1210 or the electronic module 1202 when perforations are made around the components.

In certain implementations, perforations are made or patterned around one or more components placed on the substrate 1230, such as the electronic connections 1210, or the electronic module 1202. In some embodiments, the substrate can be perforated before one or more components are placed on the substrate. Although a single electronic module 1202 is illustrated, in certain implementations, a plurality of electronic modules can be used. Additional details of component or connection placement, perforation, or coating are described in International Patent Application No. PCT/EP2018/059333 titled COMPONENT STRESS RELIEF FOR SENSOR ENABLED NEGATIVE PRESSURE WOUND THERAPY DRESSINGS, filed on 11 Apr. 2018, which claims the benefit of U.S. Provisional Patent Applications Nos. 62/484,316 titled COMPONENT STRESS RELIEF FOR SENSOR ENABLED NEGATIVE PRESSURE WOUND THERAPY DRESSINGS, filed on Apr. 11, 2017; 62/484,321 titled COMPONENT STRESS RELIEF FOR SENSOR ENABLED NEGATIVE PRESSURE WOUND THERAPY DRESSINGS, filed on Apr. 11, 2017; 62/524,564 titled COMPONENT POSITIONING AND STRESS RELIEF FOR SENSOR ENABLED NEGATIVE PRESSURE WOUND THERAPY DRESSINGS, filed on Jun. 25, 2017; and International Patent Application No. PCT/EP2018/069883 titled BIOCOMPATIBLE ENCAPSULATION AND COMPONENT STRESS RELIEF FOR SENSOR ENABLED NEGATIVE PRESSURE WOUND THERAPY DRESSINGS, filed on 23 Jul. 2018, which claims the benefit of U.S. Provisional Patent Application Nos. 62/536,921 titled BIOCOMPATIBLE ENCAPSULATION OF COMPONENTS IN SENSOR ENABLED NEGATIVE PRESSURE WOUND THERAPY DRESSINGS, filed on Jul. 25, 2017; 62/536,926 titled BIOCOMPATIBLE ENCAPSULATION AND COMPONENT STRESS RELIEF FOR SENSOR ENABLED NEGATIVE PRESSURE WOUND THERAPY DRESSINGS, filed on Jul. 25, 2017; and 62/556,461 titled BIOCOMPATIBLE ENCAPSULATION AND COMPONENT STRESS RELIEF FOR SENSOR ENABLED NEGATIVE PRESSURE WOUND THERAPY DRESSINGS, filed on Sep. 10, 2017, each of which is incorporated by reference in its entirety.

In some embodiments, a conductive track 1240 (which can also be referred to as calibration track) encompassing or enclosing the plurality of electronic components is partially or completely positioned on the periphery of the substrate 1230. In some embodiments, the conductive track 1240 can be constructed substantially similarly to the one or more tracks 1210 and changes in the resistance of the conductive track 1240 can be measured and used as a proxy for changes in the resistance of the one or more tracks 1210. For example, the conductive track 1240 can be of the same or substantially same width as the one or more tracks 1210 and may be composed of conductive material, such as copper, conductive ink (such as silver ink, graphite ink, etc.), or the like. The conductive track 1240 can be connected to a monitoring circuit (not shown) that measures the change in the impedance or resistance of the conductive track 1240. The monitoring circuit can be part of a control module, such as a control module or controller. In some implementations, the monitoring circuit may additionally or alternatively measure other types of electrical measurements that have a defined mathematical relationship with resistance, such as voltage or current. For simplicity, the monitoring circuit is described as measuring resistance, but a skilled person would readily appreciate that the measurement can be of any associated measurable electrical property.

The conductive track 1240 can include longitudinal and perpendicular portions encompassing or encircling substantially the entire perimeter of the wound contact layer (as shown in FIG. 12), such that the conductive track 1240 can be subjected to (and therefore permit detection of resistance changes) of stretching or straining the dressing regardless of the direction or force. In some embodiments, other alternative or additional configurations of the conductive track 1240 may be employed, such as one or more separate tracks extending longitudinally, perpendicularly, or radially from the electronic component 1202 or one or more tracks 410.

In some embodiments, the monitoring circuit may acquire one or more resistance readings from the conductive track 1240 for calibration. Calibration can be performed at a stable and normal operating conditions of the wound dressing, such as in an environment without or substantially without stress or strain on the wound dressing. For example, calibration can be performed prior to applying the wound dressing on patients, such as during manufacturing, packaging, or the like. Calibration can provide a baseline reading, such as baseline resistance, from which changes in the conductive track 1240 resistance can be measured when the dressing is in use. In some embodiments, additional or alternative baseline reading may be acquired from the conductive track 1240 put under strain or stress.

In certain implementations, when the wound dressing is put under strain or stress, resistance of the conductive track 1240 changes from the baseline resistance. The monitoring circuit alone or in combination with a controller can make a comparison of the new measurement or reading against the baseline reading to measure the change in resistance and determine whether the change is within acceptable bounds to ensure that the measurement(s) obtained by one or more sensors are correct. In some embodiments, such determinations may be made by comparing the difference between the readings to one or more threshold values.

In some embodiments, when the monitoring circuit alone or in combination with a controller determines that the change is unacceptable, such as when the change exceeds one or more threshold values, one or more remedial measures can be performed. The one or more remedial measures may include (1) delaying or ignoring one or more new sensor readings until the resistance change becomes acceptable again, (2) informing a patient or caregiver to remove the source of the stress or strain, or (3) compensating the one or more new sensor readings to account for the change in resistance, such as by using calibration as described herein. Delaying one or more new sensor readings may involve deactivating one or more drive circuits for one or more sensors affected by the strain or stress or deactivating the one or more affected sensors. The one or more remedial measures can be performed by the one or more of the monitoring circuit or the controller.

The monitoring circuit can include various circuit elements. For example, the monitoring circuit can include a voltage divider, Wheastsone bridge, or the like to measure resistance change(s). The monitoring circuit can additionally or alternatively include one or more active elements. As another example, the monitoring circuit can include a current source supplying a known current to the conductive track with an active switch, such as a transistor switch. When resistance is increased beyond one or more thresholds, the switch can become activated and indicate unacceptable deviation(s) from the baseline resistance. As yet another example, a constant current source can be utilized and voltage needed to generate the constant current can identify the resistance. In some embodiments, the monitoring circuit can include a controller or microprocessor, which can compare and execute the remedial measures.

In some embodiments, a patient or caregiver may be alerted to remove the source of the stress or strain. For example, one or more of a visual, audible, tactile, or the like alarms can be generated.

Figure 13:
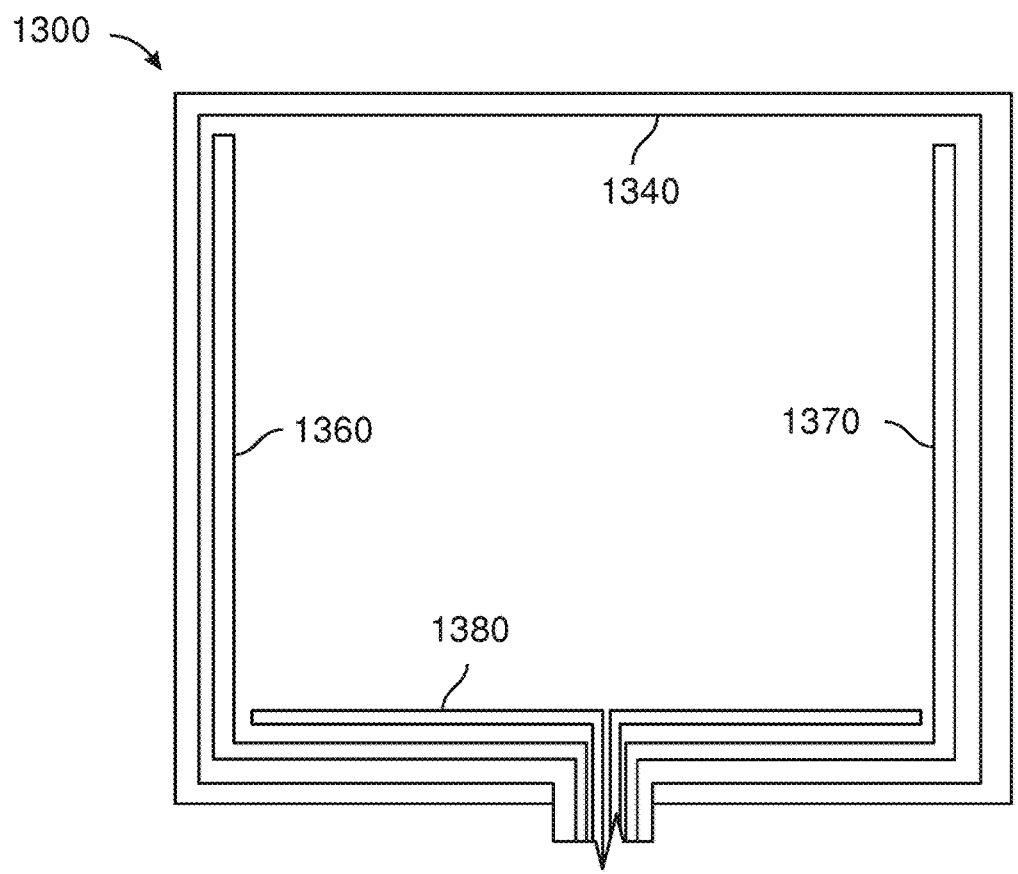
FIG. 13 illustrates arrangements for monitoring changes in electrical impedance according to some embodiments.

FIG. 13 illustrates arrangements of a plurality of conductive tracks positioned on a wound contact layer 1300 according to some embodiments. In addition to a conductive track 1340 that encompasses or encircles substantially the entire perimeter of the wound contact layer, conductive tracks 1360 and 1370 can be positioned, respectively, on the left and right sides of the wound contact layer to independently measure changes in resistance on the left and right sides. Tracks 1360 and 1370 can additionally extend to the bottom of the wound contact layer as illustrated. Also, a bottom conductive track 1380 can be positioned to independently measure changes in the resistance on the bottom side of the wound contact layer.

In some embodiments, track 1360 can indicate changes in resistance on the left side of the wound contact layer. Track 1370 can indicate changes in resistance on the right side of the wound contact layer. Track 1380 can indicate changes in resistance on the bottom side of the wound contact layer. Changes in resistance on the top side of the wound contact layer can be determined by subtracting from the measurement obtained using the track 1340 measurement obtained by the tracks 1360 and 1370. These operations can be performed by the monitoring circuit as described herein. The conductive tracks illustrated in FIG. 13 can be calibrated as described herein.

In certain embodiments, a separate conductive track can be positioned to measure resistance change of each electrical component (for instance, sensor) block or cluster of a plurality of clusters. For example, with reference to FIG. 1C, an outer conductive track can be positioned on the perimeter of the wound contact layer to measure resistance change of the outer four sensors, and an inner conductive track can be positioned around the four sensors in the middle of the wound contact layer to measure resistance change of those sensors. In such arrangements, it may be possible to adjust the measurements obtained by one or more sensors from a particular component cluster based to account for changes in the resistance measured by the conductive track associated with that cluster.

Figure 14A:
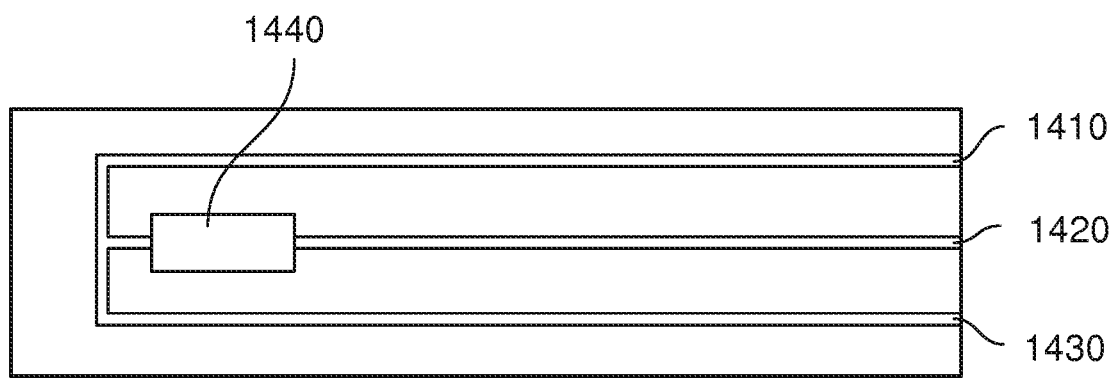
FIGS. 14A-14E illustrate arrangements of tracks for monitoring changes in electrical impedance according to some embodiments.
Figure 14B:
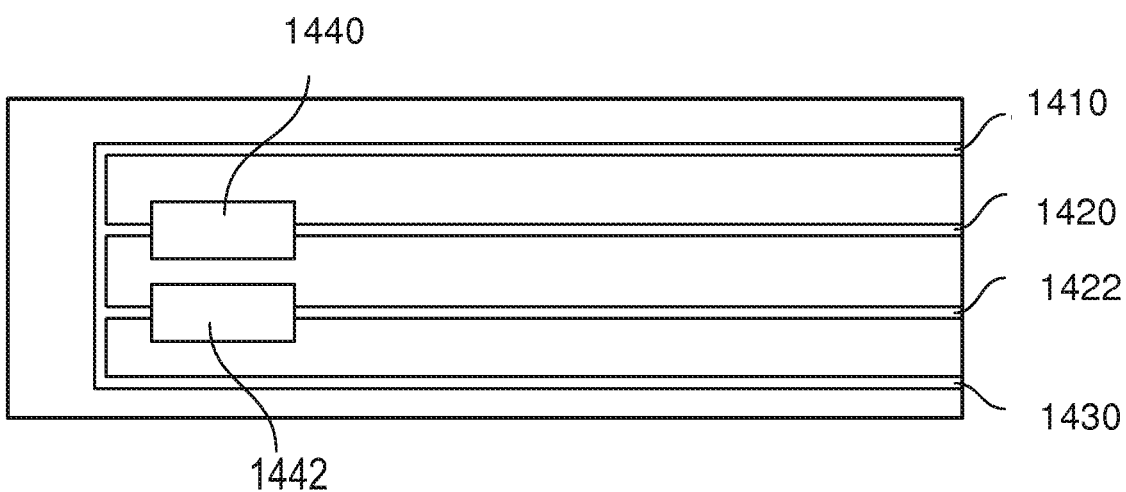

FIGS. 14A-14D illustrate arrangement of conductive tracks for measuring changes in electrical impedance according to some embodiments. As illustrated in FIGS. 14A-14B, in some implementations, power to one or more electrical components 1440 or 1442 (for example, one or more sensors) can be supplied by an electrical connection or track 1410. One or measurements taken by the components 1440 or 1442 can be supplied by electrical connections 1420 or 1422, respectively. Conductive track 1430 can be used to measure resistance changes for the components 1440 or 1442. Using such arrangement, resistance changes of a component cluster, such as a cluster including components 1440 and 1442, can be obtained using one conductive track 1430.

Figure 14C:
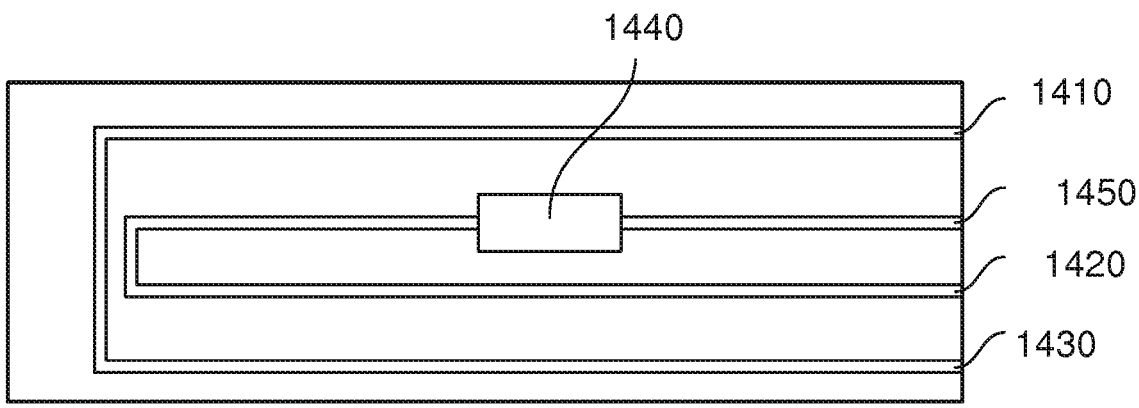
Figure 14D:
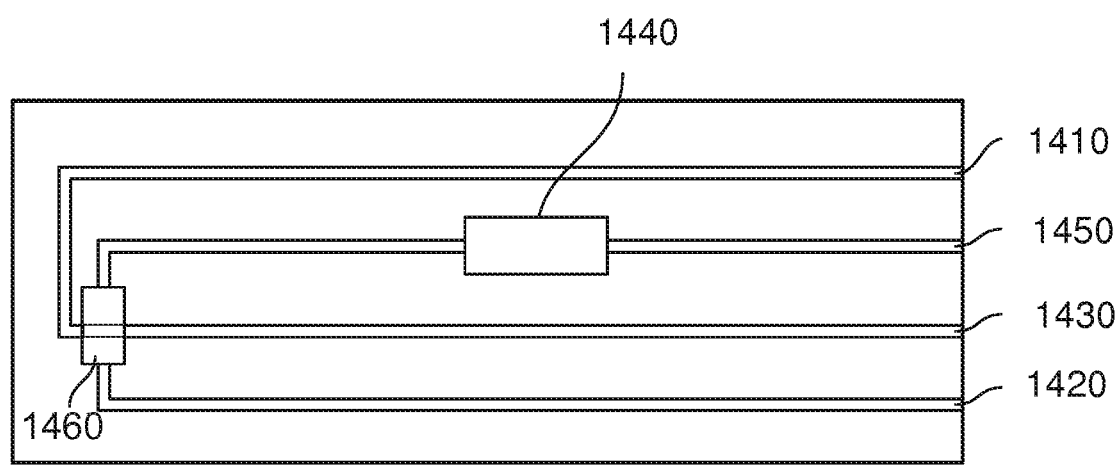

In some embodiments, as illustrated in FIGS. 14C-14D, power can be supplied separately to the one or more components, such as the component 1440, on track 1410 and to the one or more conductive tracks, such as the track 1430, on track 1450. Such arrangement can permit determination of resistance changes without affecting power supply to the electrical components, which can reduce interference or noise generated by the one or more tracks 1430. As illustrated in FIG. 14D, masking 1460 can be used for isolation in order to allow electrical tracks to cross without creating a short circuit. Alternatively or additionally, isolating circuit elements (such as diodes or transistors) can be used for isolation. In some cases, preferential paths for resistance measurement can be created using one or more isolating circuit elements.

Figure 14E:
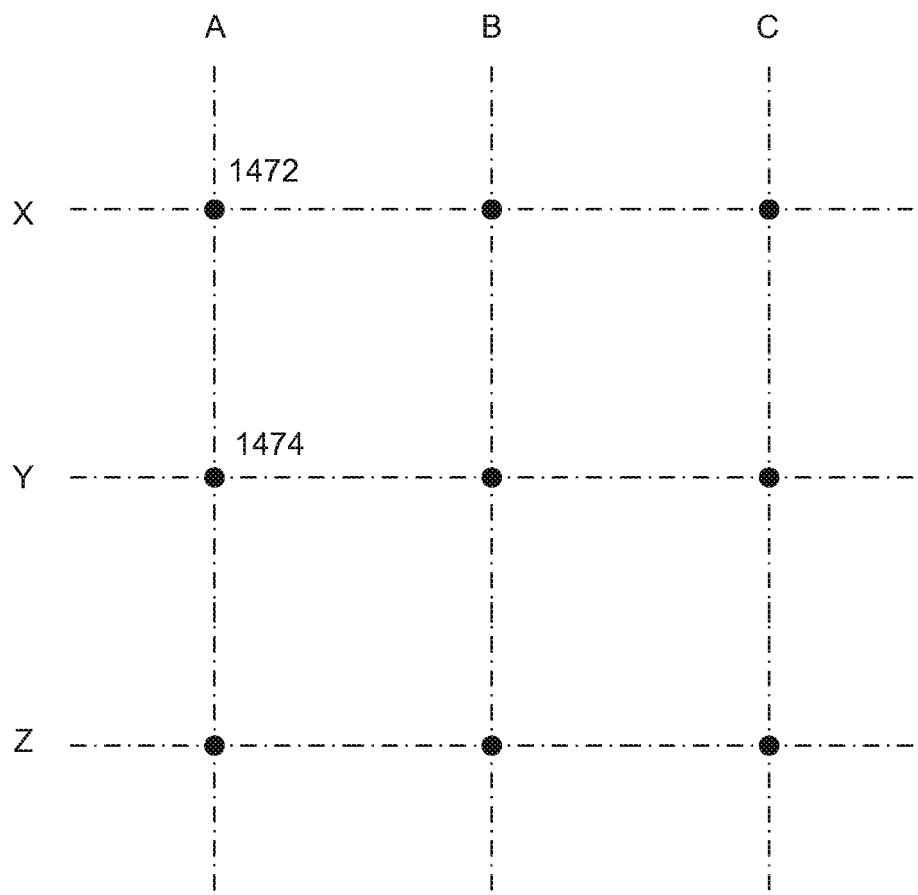

In certain cases, conductive tracks for measuring resistance changes can be arranged as a grid across a wound contact layer. Each of the conductive tracks or any combination of conductive tracks can measure resistance changes associated with a particular portion of the wound contact layer, which can include a set of sensors. For example, the grid of conductive tracks can include vertical tracks A, B, and C and horizontal tracks X, Y, and Z as illustrated in FIG. 14E. Measuring resistance changes between tracks A and X, such as at the intersection point 1472 of the tracks, can indicate resistance changes in the upper left portion of the grid. This resistance change can be associated with changes in the resistance of one or more sensors positioned in the upper left portion. Measuring resistance changes between tracks A and Y, such as at the intersection point 1474 of the tracks, can indicate resistance changes in the portion of the grid located below the upper left portion. This resistance change can be associated with changes in the resistance of one or more sensors positioned in the portion of the grid located below the upper left portion. Arrangement of conductive tracks can provide one or more paths for measuring resistance changes in portions of the wound contact layer.

In some implementations, the monitoring circuit or controller can compensate one or more new sensor readings based on the detected change(s) in resistance. The measurement of the one or more new sensors can be adjusted based at least one of the determined change(s) in resistance, deviation from the one or more thresholds, or the like. For example, one or more compensation factors (such as an offset or scale factor) can be applied to the one or more new sensor readings. In some embodiments, one or more sensors may be alternatively or additionally equipped with a strain gauge or similar circuit (not shown) to individually calibrate and compensate for the effect of resistance change on the sensor reading.

In certain implementations, changes in the impedance or resistance of one or more sensors due to straining, stretching, contracting, or tearing of the substrate can be additionally or alternatively detected and compensated for using any one or more of the approaches described herein. In some cases, one or more conductive tracks may have different dimensions or material compared to the sensor tracks, such that it is more or less sensitive to straining, stretching, contracting, or tearing.

In some embodiments, one or more conductive tracks can also improve protection against noise, including electrostatic discharge (ESD). For example, a conductive track can be positioned around the periphery of the substrate to protect against ESD. Additional conductive tracks can be connected to the conductive track positioned on the periphery. Such one or more conductive tracks can provide path for ESD spike to travel. The conductive track positioned on the periphery and one or more additional conductive tracks can be positioned away from one or more electronic components, such as sensors. The conductive track positioned on the periphery (or any other one or more conductive tracks) can be connected to one or more resistors to protect against ESD. The one or more resistors can be carbon resistors. In some cases, one or more calibration tracks can function as inductive coil(s) configured to receive power wirelessly.

Antennas for Remote Communication

In some embodiments, a controller or control module, such as the control module 330, configured to be connected to the wound dressing can include one or more antennas for wireless communication. The one or more antennas can be used to communicate measurement data collected by the one or more sensors of the wound dressing. The one or more antennas can additionally be used to receive power wirelessly from a power source or to transmit power to the wound dressing. For example, an antenna can include one or more loops that can facilitate wireless transmission or reception of power.

Figure 15A:
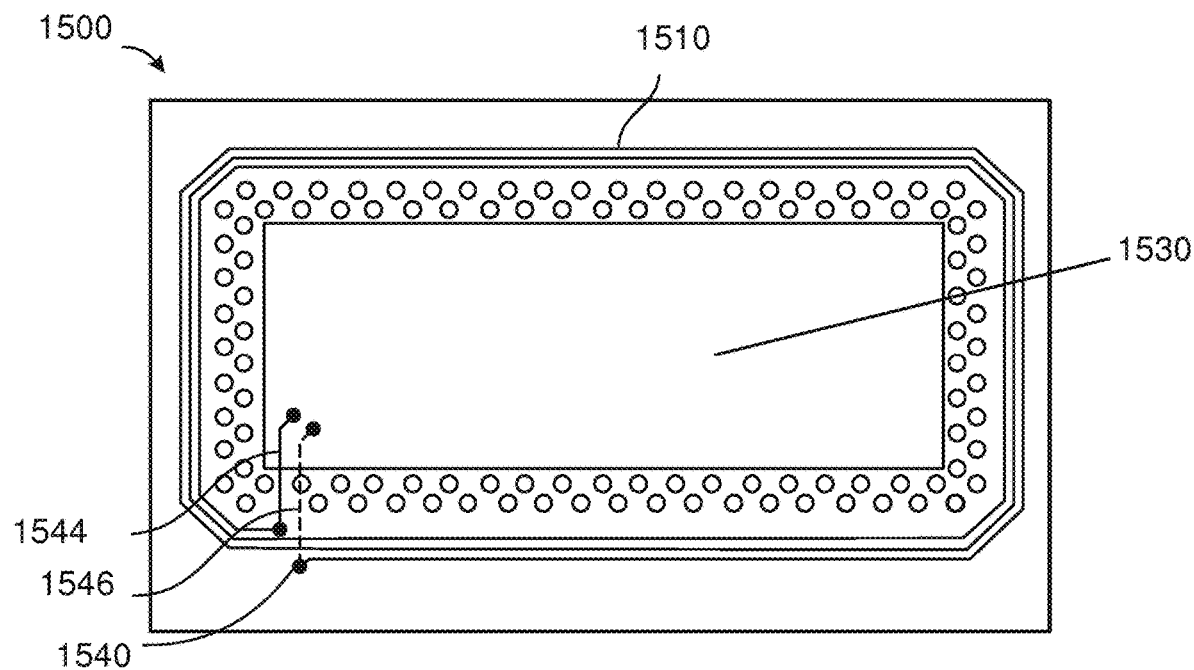
FIGS. 15A-15B, 16A-16B, and 17A-17B illustrates sensor enabled wound dressings with an antenna according to some embodiments.
Figure 15B:
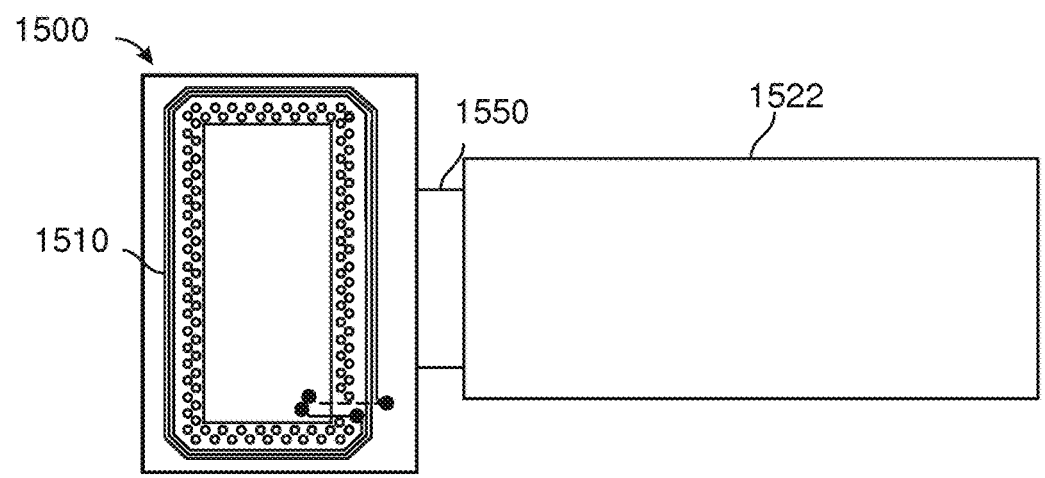

FIGS. 15A-15B illustrate a controller 1500 including an antenna 1510 enclosing a plurality of electrical components 1530, which can also include a battery. Antenna 1510 and/or any of antennas described herein, including antenna 1610 and antenna 1710, can surround one or more calibration tracks as described herein. The electronic components 1530 and antenna 1510 can be supported on a substrate, such as a circuit board. By fully or substantially enclosing the electrical components 1530, the antenna advantageously can provide a desirable communication range or have good reception/transmission characteristics regardless of the direction, which may be referred to as 360 degree coverage. The illustrated design can achieve these and other advantages while limiting interference with the electrical components and while conforming with applicable communication standards, such as ISO/IEC ((International Organization for Standardization (ISO) and the International Electrotechnical Commission (IEC)) antenna standards.

The antenna 1510 can include copper wire, substrate track or trace, or the like. The antenna 1510 can be etched or printed. For example, the antenna 1510 can include a printed trace on a substrate, and the printed trace can include conductive copper or conductive ink, such as silver ink, graphite ink, or the like.

As illustrated, the antenna 1510 can be shaped such that it encloses electrical components 1530 of the controller 1500. The pattern or shape of the antenna 1510 can vary depending on an embodiment. Accordingly, although the antenna 1510 is illustrated as being arranged in a generally rectangular (or roughly octagonal) configuration, the antenna 1510 may take on roughly any shape as it encloses or surrounds the electrical components 1530. For example, the antenna 1510 can be rectangular, square, round (circular or loop), L-, C-, W-, G-, D-, or U-shaped, include straight or curved corners, or the like. In some cases, as described herein, it may be advantageous for the antenna 1510 to include smooth turn/corner transitions rather than sharp corner turns.

The antenna 1530 can include a combination of one or more straight, bent, or curved portions. For example, the antenna 1510 can include a combination of one or of a straight trace, an inverted F-type trace, a meandered trace, a circular trace, a curved trace, a trace with twists, a spiral trace, or the like. In some cases, the antenna 1510 may be shaped such that it generally outlines an outer edge of the controller 1500 (such as, is positioned along the perimeter of the substrate) or encloses the electrical elements 1530.

The antenna 1510 can be configured as a near-field antenna. For example, the antenna 1510 may support near field communication (NFC) such that communication may be established when a communication device is brought within a particular range of the antenna 1510. The particular range may vary across embodiments. For example, the particular range may include, but is not limited to, about one wavelength of the antenna 1510 or within about 2, 4, 6, 8, 10, 12, 15, or 20 cm (+/− a few centimeters). In some embodiments, the antenna can provide spherical coverage rather than merely 360 degree planar coverage.

The antenna 1510 can be categorized as a Class 4 antenna as defined by ISO/IEC 14443 standard. For example, the antenna 1510 can be located within a zone defined by either: (1) an external rectangle of 50×27 mm and an internal rectangle of 35×13 mm, centered in the external rectangle, with 3 mm corner radii; or (2) or an external circle with diameter 41 mm and an internal circle with diameter 24 mm, concentric with the external circle. In some embodiments, the antenna 1510 can be categorized another class, such as a Class 1, 2, 3, 5, 6, or 7.

In some cases, the substrate of the controller 1500 can be a multilayer circuit board (such as, with 4 layers), and the antenna 1510 can include traces that occupy several layers of the multilayer circuit board. For example, the antenna 1510 may enclose electrical components 1530 on some or all of the multiple layers.

Vias 1540 may be used to interconnect the antenna 1510 portions on each of the layer. For example, the vias 1540 may provide an electrical connection between each of the portions of the antenna 1510 and, in some cases, can electrically connect the antenna 1510 and one or more of the electrical components 1530 (e.g., a radio frequency (RF) circuit or microprocessor, power source, such as a battery, or the like). The vias 1540 can advantageously isolate the antenna 1510 from the electrical components 1530, thereby reducing a likelihood of interference with the reception/transmission of the antenna 1510. In addition or alternatively, the vias 1540 can improve noise immunity with respect to transmitting or receiving using the antenna 1510. As illustrated in FIGS. 15A and 15B, in some cases, the controller 1500 includes four vias 1540 on each layer comprising a portion of the antenna 1510. For example, the vias 1540 may allow the antenna 1510 to electrically connect to an RF circuit whose connections are positioned on another layer or layers of the circuit board. For example, the two vias 1540 of the antenna 1510, which can correspond to positive and negative terminals, can be connected as shown by the connections 1544 and 1546, respectively, to the positive and negative terminals of the RF circuit, which is included in the plurality of electronic components 1530.

In some cases, certain elements of the controller 1500 may be encapsulated with an EMC shield. For example, a battery or other hardware can be so encapsulated in order to limit or reduce a likelihood of interference between antenna 1510 and the encapsulated components.

It may be advantageous for the antenna 1510 to enclose a majority of the area of the controller 1500 to provide the broadest coverage region. Accordingly, the antenna 1510 may extend approximately to the periphery or edges of the controller 1500, and, in some cases, the antenna loop make take on a shape similar to that of the controller 1500. Embodiments of the antenna 1510 provide for various configurations in which the antenna 1510 encloses portions of the controller 1510. For example, the antenna 1510 may be shaped such that it encloses a portion of the area of the controller, such as 10, 15, 20, 25, 30, 35, 40, 45, 50, 55, 60, 65, 70, 75, 80, 85, 90, 85, or about 100 percent (+/- a few percent) of the area of the controller 1500.

The performance of the antenna 1510 can be determined by a plurality of antenna parameters. For a rectangular antenna, these can include, among other things, overall dimensions of the antenna, average dimensions of the antenna, a track thickness, a track width, a size of a gap between the tracks, a number of turns of the antenna, an equivalent diameter of the track, or a turn exponent. Performance of a round antenna can be based on, among other things, a diameter of the antenna, a track thickness, a track width, a size of a gap between the tracks, a number of turns of the antenna, an equivalent diameter of the track, a turn exponent, an average diameter of the antenna, or average circumference of the antenna. As such, the performances of any antenna can be based on a shape of the antenna. Accordingly, as the shape of the antenna varies across various embodiments, applicable antenna parameters can vary.

The antenna 1510 can include a number of turns (sometimes referred to as loops or tracks). The number of turns of the antenna 1510 may vary across embodiments. For example, although the antenna 1510 illustrated in FIG. 5A includes 3 turns, in some embodiments, the antenna 510 may have fewer or more turns. For instance, the antenna may include 1, 2, 3, 4, 5, 7, 8, 9, 10, or more turns. Furthermore, the antenna may include one or more partial turns.

The thickness of the antenna 1510 and the size of the gaps between the tracks of the antenna may vary across embodiments. For example, the thickness of the antenna can be uniform throughout the length of the antenna. Alternatively, the thickness of the antenna may vary across the length of the antenna 1510. Similarly, the gaps between the tracks of the antenna 1510 can be uniform throughout or may vary across a length of the antenna 1510.

In some cases, a design in which an antenna 1510 encloses electrical components 1530 advantageously provides for more reliable and effective wireless communication as compared to designs in which an antenna is confined to a particular region of the substrate of the controller 1500 (for example, confined to a single corner).

For example, a user can scan, and thus communicate with, a controller 1500 using a near field communication (NFC) device. The NFC device can be configured to communicate with the controller via the antenna 1510 when the device is moved within a particular distance of the antenna 1510. Accordingly, by configuring the antenna 1510 such that it encloses the electrical components 1530, thereby enclosing a relatively broad area of the controller 1500, a user may reliably communicate with the controller 1500 by bringing the device within the communication range from virtually any direction or angle with respect to the controller 1500.

In contrast, if the antenna were confined or limited to a particular region of the substrate of the controller (for example, positioned in a corner), in some cases, the user may have difficulties communicating with the controller via the NFC device. For instance, the user may be scanning the device over the controller, but a communication link may not be established to the positioning of the antenna. Accordingly, by positioning the antenna 1510 such that it encloses the electrical components 1530 (for example, as illustrated in FIGS. 15A-15B) and encompasses a relatively wide area of the substrate, the user may be able to communicate with the controller 1500 via the NFC device, regardless over which region of the controller 1500 the user swipes the device. It will be appreciated that other forms of communication using the antenna 1510 are contemplated. For example, wireless communication can be performed over any wireless interface, such as via RFID, far field, or the like when a communication device is placed within communication range of the antenna 1510.

FIG. 15B illustrates the controller 1500 of FIG. 15A connected to a sensor enabled wound dressing 1522, which can be similar to the sensor enabled wound dressing 22 of FIG. 1C. As illustrated, the controller 1500 is connected to the sensor enabled wound dressing 1522 via a connector 1550. Connector 1550, which can be similar to the connector 28 of FIG. 1C, is configured to allow communications between the controller 500 and the wound dressing 1522. As described herein, information communicated between the controller 500 and the wound dressing 1522 via the connector 1500 can include, but is not limited to, sensor information, such as impedance, temperature, or light characteristics obtained from one or more of the wound or periwound.

Figure 16A:
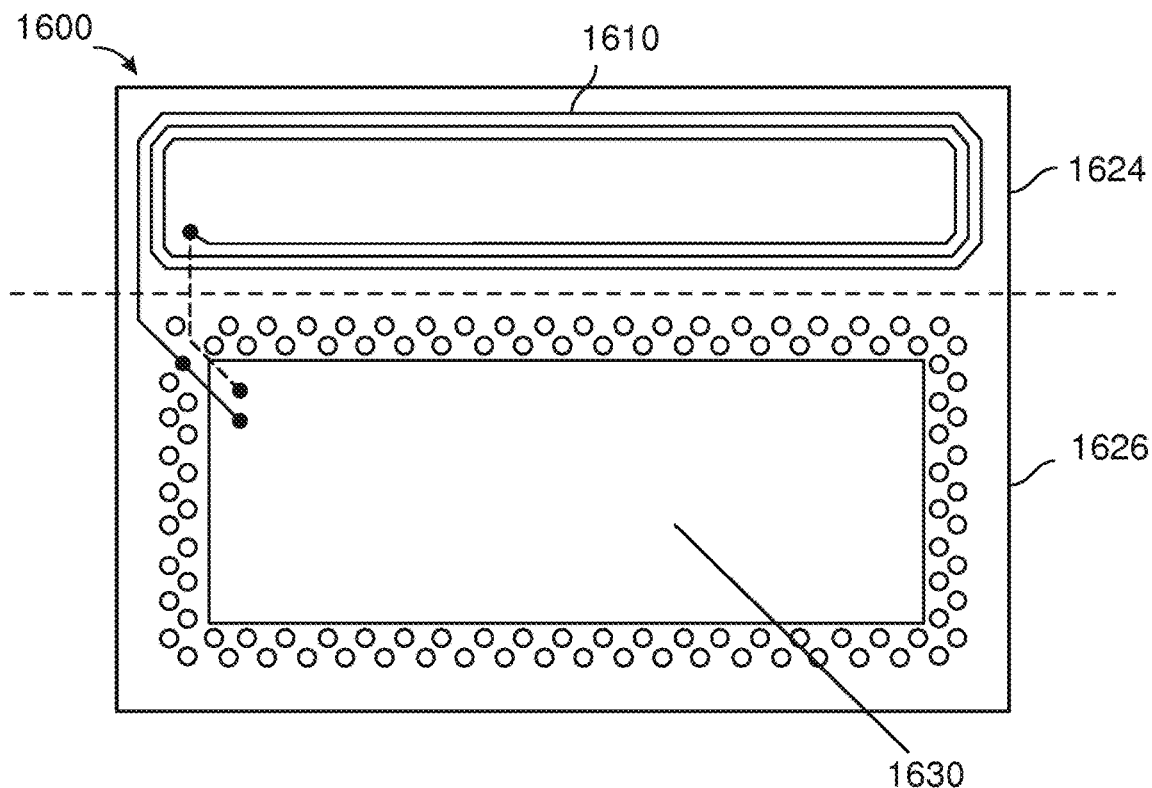
Figure 16B:
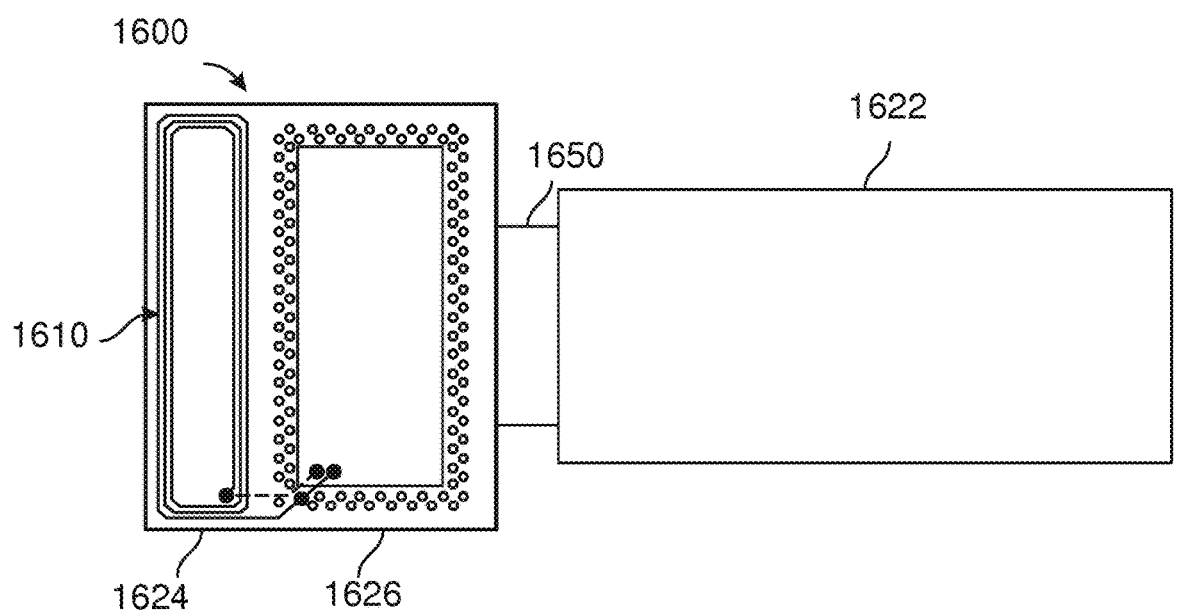

FIGS. 16A-16B illustrate a controller 1600 including an antenna 1610 and electrical components 1630. The antenna 1610 may have any of the features of antenna 1510 of FIGS. 15A and 15B, as described herein. However, in contrast to antenna 1510, antenna 1610 does not enclose the electrical components 1630. Rather, the antenna 1610 is remotely located from the one or more electrical components 1630. For example, the antenna 1610 can be positioned in a first region 1624 of the circuit board that different from a second region 1626 of the circuit board that the electrical components 1630 are positioned.

In some cases, by configuring the antenna 1610 such that it is remotely located from the one or more electrical components 1630, the likelihood of interference between the antenna 1610 and the electrical components 1630 is reduced. As illustrated, the coverage of the antenna 1610 can include a large portion of the controller 1600 opposite the electrical components. The controller can include multiple antennas 1610 in various positions on the controller 1600. Configuring an antenna 1610 in multiple locations can advantageously increase the coverage area of the antenna 1610. For example, multiple antennas can be placed in multiple corners of the controller 1600, thereby allowing the antenna 1610 to be read from any of those corners.

FIG. 16B illustrates the controller 1600 of FIG. 16A connected to a sensor enabled wound dressing 1622, which can be similar to the sensor enabled wound dressing 22 of FIG. 1C. As illustrated, unlike the antenna 1510 in FIG. 15A, the antenna 1610 is positioned remotely from the connector 1600. Because the antenna 1610 is located away from the connector 1600, this configuration can reduce a likelihood of introducing noise or interference from the antenna 1610, which may interfere with or degrade communications between the controller 1600 and the wound dressing 1622 via the connector 1650. Similarly, the illustrated configuration can reduce a likelihood of introducing noise or interference from the connector 1650, which may interfere with or degrade wireless communications of the controller 1600 via the antenna 1610.

Figure 17A:
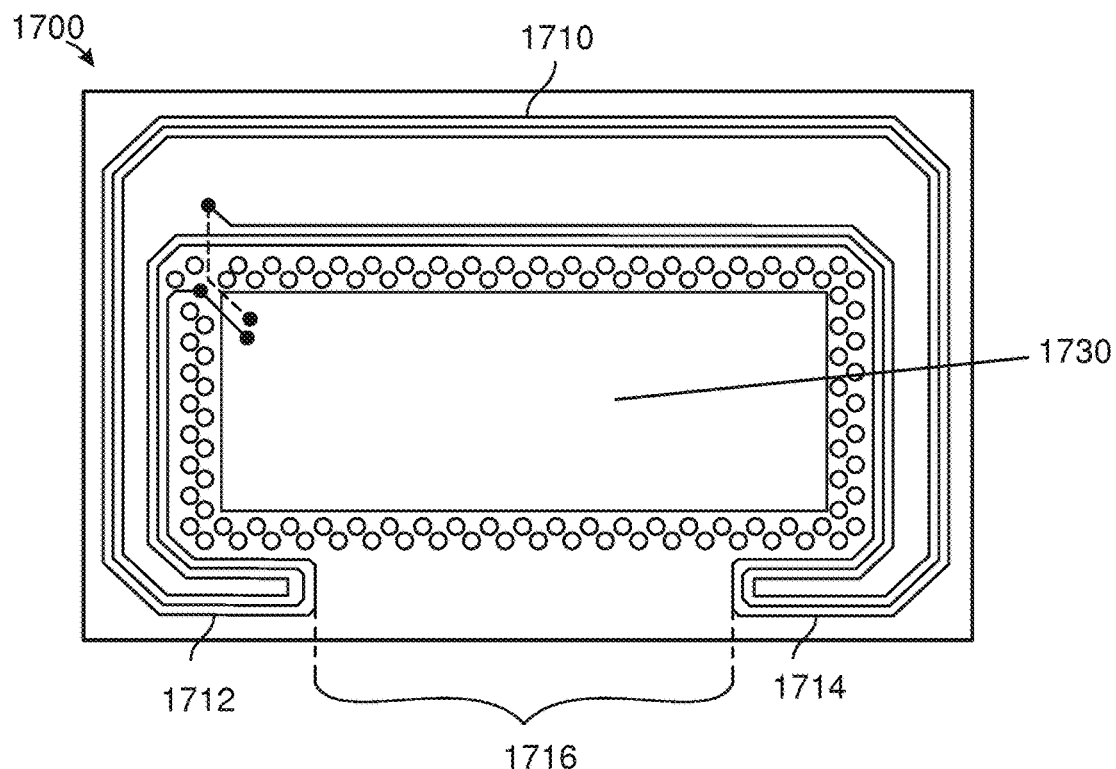
Figure 17B:
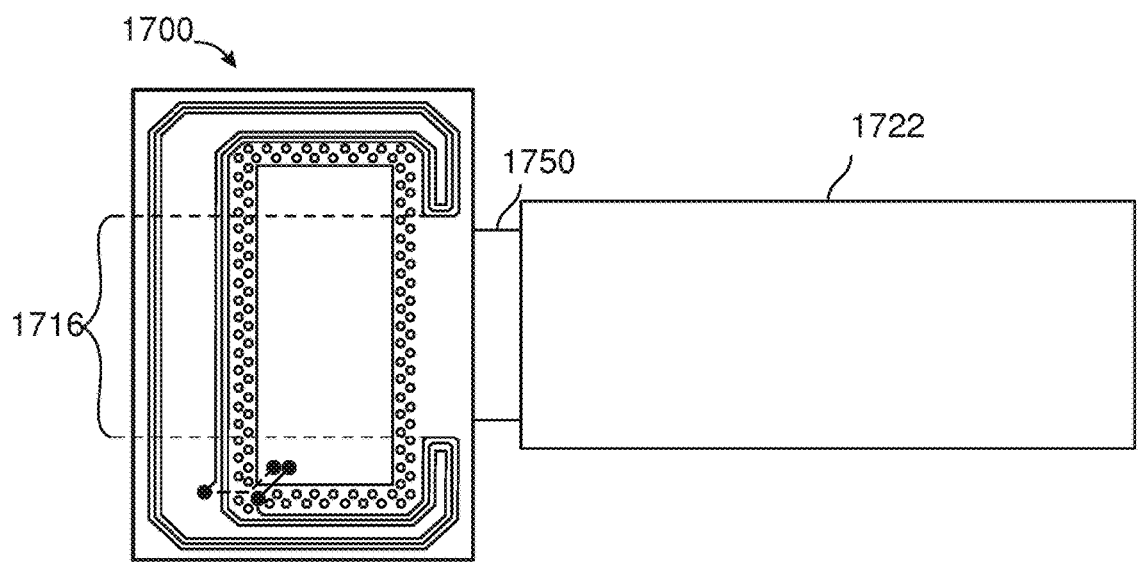

FIGS. 17A-17B illustrate a controller 700 including an antenna 1710 positioned such that it substantially encloses the electrical components 1730 (which can be similar to the electrical components 1530) with exception of an area 1716 over or through which the electrical components 1730 connect to the sensor enabled wound dressing 1722 via a connector 1750. The wound dressing 1722 can be similar to the sensor enabled wound dressing 22 of FIG. 1C. The antenna 1710 may have any of the features of antenna 1510 of FIGS. 15A and 15B, as described herein. However, in contrast to antennas 1510 and 1610, antenna 1710 substantially encloses the electrical components 1730 but does not overlap with the connector 1750 when the controller 1700 and sensor enabled wound dressing 1722 are connected. By positioning the antenna 1710 such that it substantially encloses the electrical components 1730 (such as, fully encloses the electrical components except for an opening in the area 1716), the antenna can advantageously provide for more reliable and efficient wireless communications as described herein. In addition, configuring the antenna 1710 such that it does not overlap (or overlaps minimally) with connector 1700 when the controller 1700 is connected to the wound dressing 1722 via the connector 1700, the design can advantageously reduce a likelihood of introducing noise or interference as described herein.

Although the embodiments described herein with respect to FIGS. 15A-17B describe an antenna incorporated into a controller, any of the one or more antennas as described herein may be incorporated into a wound dressing, such as being supported on a substantially flexible wound contact layer. For example, one or more antennas, as described herein, can be printed as one or more connections or traces on a wound contact layer, such as the substantially stretchable wound contact layer. In certain cases, the one or more antenna traces can be positioned on a substantially non-stretchable material (as described herein) such that the resonant frequencies of the one or more antennas remain fixed when the wound dressing, such as the wound dressing 22 in FIG. 1C, becomes is placed under stress when in use on a patient. Fixing the one or more resonant frequencies can be advantageous for certain communication protocols, such as RFID. The one or more antennas can be used to communicate measurement data collected by the one or more sensors without the controller. The one or more antennas can additionally be used to receive power wirelessly from a power source.

In some cases, a resonant frequency of an antenna positioned on a substantially flexible substrate can change as the substrate is stretched or torn, as described herein. Changes in the resonant frequency can be measured from one or more electromagnetic signals transmitted by the antenna. For example, the antenna can be connected to an oscillator driver. Alternating current output signals can be used for communication, while direct current output signals can be used for measuring the strain. In some cases, an antenna can be connected to a circuit whose one or more electrical properties change as a results of the strain. The circuit can include one or more calibration tracks, strain gauges, or the like, as described herein. The antenna and the circuit can form a resonant circuit whose resonant frequency can change as the substrate is stretched or torn, as described herein. Changes in the resonant frequency can be measures from one or more electromagnetic signals transmitted by the antenna. Changes in resonant frequency can be indicative of a degree of stretching or tearing of the substrate and the resistance change as described herein. Changes in resonant frequency of the antenna or the circuit including the antenna can be used with any of the embodiments described herein in order to measure changes in the resistance.

Additional Variations

In some embodiments, a wound monitoring and/or therapy system includes a wound dressing configured to be positioned over a wound, the wound dressing including a substantially stretchable wound contact layer supporting a plurality of electronic components and a plurality of electronic connections that connect at least some of the plurality of the electronic components. The plurality of electronic components can include a plurality of sensors configured to obtain measurement data of at least one of the wound or periwound. The plurality of electronic components can include at least one controller configured to control at least some of the plurality of sensors, the at least one controller configured to operate without failure when the at least one controller is flexed as a result of strain on the wound dressing.

The system of preceding paragraph can include one or more of the following features. The at least one controller can be subjected to compression in order to increase resiliency of the at least one controller to flexing. The at least one controller can be pre-strained. The wound dressing can include a coating covering at least some of the plurality of electronic components and at least some of the plurality of electronic connections, and the coating can compresses the at least one controller when applied to the wound dressing. The coating can be hydrophobic and bio compatible. The wound dressing can include an antenna configured to communicate measurement data to a remote computing device.

The system of one or more of preceding paragraphs can include one or more of the following features. The system can include a power source positioned on the wound contact layer and configured to power the plurality of electronic components. The power source may not be enclosed in a separate casing or enclosure. The wound contact layer can include first and second portions, the power source can include an anode supported by the first portion of the wound contact layer and a cathode supported by the second portion of the wound contact layer, and the power source can include an electrolyte layer positioned between the anode and cathode.

The system of one or more of preceding paragraphs can include one or more of the following features. The at least one controller can be configured to be activated by one or more of: flexing the wound dressing, activating an activation switch, bursting a bubble of conductive material, charging a transistor, initiating a magnetic trigger, or triggering a piezoelectric element. The system can be configured to not be physically connected to an external controller that controls any of the plurality of sensors or receives any of the measurement data.

In some embodiments, a wound monitoring and/or therapy system includes a wound dressing configured to be positioned over a wound, the wound dressing including a substantially stretchable wound contact layer supporting a plurality of electronic components and a plurality of electronic connections that connect at least some of the plurality of the electronic components. The plurality of electronic components can include a plurality of sensors configured to obtain measurement data of at least one of the wound or periwound and a control module configured to be connected to the wound dressing. The control module can include at least one controller configured to obtain the measurement data from the plurality of sensors and a power source configured to provide power to the at least one controller and the plurality of sensors, the at least one controller and power source enclosed in an enclosure.

The system of one or more of preceding paragraphs can include one or more of the following features. The enclosure can include a first portion supporting the at least one controller and power source and a second portion configured to be attached to at least one pin positioned on the first portion. The enclosure can be configured to substantially shield the at least one controller from electromagnetic interference (EMI) and electrostatic discharge (ESD).

In some embodiments, a wound monitoring apparatus includes a wound dressing configured to be positioned in contact with a wound, the wound dressing including a substantially stretchable wound contact layer supporting a plurality of sensors configured to obtain measurements of at least one of the wound or periwound and a plurality of conductive tracks electrically connecting the plurality of sensors. The wound contact layer can further support at least one calibration track electrically connected to a monitoring circuit configured to measure a first change in resistance of the at least one calibration track, the first change in resistance of the at least one calibration track corresponding to a change in resistance of at least some of the plurality of conductive tracks.

The apparatus of the preceding paragraph can include one or more of the following features. The at least one calibration track can be at least partially positioned on a perimeter of the wound contact layer. The at least one calibration track can include a plurality of calibration tracks, and wherein each of the calibration tracks is associated with a particular sensor of the plurality of sensors. The monitoring circuit can be further configured to measure a baseline resistance of the at least one calibration track when an intact wound contact layer is not stretched and determine the first change in resistance of the at least one calibration track based on a difference between the baseline resistance and resistance of the at least one calibration track due to stretching and/or tearing of the wound contact layer. The monitoring circuit can be further configured to adjust a measurement obtained by a sensor of a plurality of sensors based on the first change in resistance. The monitoring circuit can be further configured to, in response to a determination that the first change in resistance exceeds a threshold, control at least some of the plurality of sensors to defer the one or more measurements.

The apparatus of one or more preceding paragraphs can include one or more of the following features. The apparatus can include a controller configured to control the at least some of the plurality of sensors to obtain one or more measurements in response to a determination that a second change in resistance is below the threshold, the second change in resistance measured subsequent to the measurement of the first change in resistance. The at least some of the plurality of sensors can include one or more sensors configured to measure impedance. The at least one calibration track can include a plurality of calibration tracks configured to measure a plurality of first changes in resistance associated with a plurality of different regions of the wound contact layer. The at least one calibration track can be connected to a different power supply than the plurality of sensors.

In some embodiments, a method of operating a wound monitoring apparatus including a wound dressing including a substantially stretchable wound contact layer supporting a plurality of sensors configured to obtain measurements of at least one of a wound or periwound and a plurality of conductive tracks electrically connecting the plurality of sensor includes, with a monitoring circuit of the wound monitoring apparatus, measuring a first change in resistance of at least one calibration track positioned on the wound contact layer. The first change in resistance of the at least one calibration track can correspond to a change in resistance of at least some of the plurality of conductive tracks. The at least one calibration track can be at least partially positioned on a perimeter of the wound contact layer.

The method of one or more preceding paragraphs can include one or more of the following features. The at least one calibration track can include a plurality of calibration tracks, and wherein each of the calibration tracks is associated with a particular sensor of the plurality of sensors. The method can further include measuring a baseline resistance of the at least one calibration track when an intact wound contact layer is not stretched and determining the first change in resistance of the at least one calibration track based on a difference between the baseline resistance and resistance of the at least one calibration track due to stretching and/or tearing of the wound contact layer.

The method of one or more preceding paragraphs can include one or more of the following features. The method can include, by the monitoring circuit, adjusting a measurement obtained by a sensor of the plurality of sensors based on the first change in resistance. The method can include, by a controller of the wound monitoring apparatus, receiving the first change in resistance from the monitoring circuit, determining that the first change in resistance exceeds a threshold, and controlling at least some of the plurality of sensors to defer obtaining one or more measurements. The method can include, by the controller, determining that a second change in resistance measured subsequent to the measurement of the first change in resistance is below the threshold and controlling the at least some of the plurality of sensors to obtain one or more measurements. The at least some of the plurality of sensors comprise one or more sensors configured to measure impedance.

In some embodiments, a wound monitoring apparatus includes a wound dressing configured to be positioned in contact with a wound, the wound dressing including a substantially stretchable wound contact layer supporting a plurality of sensors configured to obtain measurements of the wound and a controller configured to be connected to the wound dressing and further configured to receive the measurements obtained by the plurality of sensors of the wound dressing. The controller can include a circuit board supporting a plurality of electrical components and an antenna configured to communicate with at least one of the wound dressing a remote computing device. The antenna can at least partially enclose the plurality of electrical components.

In some embodiments, a wound monitoring apparatus includes a wound dressing and a controller. The wound dressing can be configured to be positioned in contact with a wound, and the wound dressing can include a substantially stretchable wound contact layer supporting a plurality of sensors. The sensors can be configured to obtain measurements of the wound. The controller can be configured to be connected to the wound dressing. The controller can be further configured to receive the measurements obtained by the plurality of sensors of the wound dressing. The controller can include a circuit board supporting a plurality of electrical components and an antenna. The antenna can be configured to communicate with at least one of the wound dressing or a remote computing device. The antenna can at least partially enclose the plurality of electrical components.

The apparatus of one or more of the preceding paragraphs can also include any combination of the following features described in this paragraph, among others described herein. The antenna can enclose an entire region of the circuit board which includes the plurality of electrical components, except for a portion of the region that includes a plurality of connections that are configured to be connected to the wound dressing. The antenna can enclose an entire region of the circuit board that includes the plurality of electrical components.

In some embodiments, a wound monitoring apparatus includes a wound dressing and a controller. The wound dressing can be configured to be positioned in contact with a wound, and the wound dressing can include a substantially stretchable wound contact layer that supports a plurality of sensors. The sensors can be configured to obtain measurements of the wound. The controller can be configured to be connected to the wound dressing and can be further configured to receive the measurements obtained by the plurality of sensors of the wound dressing. The controller can include a circuit board that supports a plurality of electrical components and an antenna. The antenna can be configured to communicate with at least one of the wound dressing or a remote computing device, and the antenna is positioned in a first region of the circuit board different from a second region where the plurality of electrical components are positioned.

The apparatus of one or more of the preceding paragraphs can also include any combination of the following features described in this paragraph, among others described herein. The antenna can substantially enclose the entire first region. The antenna can be C-shaped. The antenna can be L-shaped. The antenna can be rectangular, square or round. The antenna can be positioned remotely from the plurality of electrical components. The antenna can include multiple loops. The antenna can include three loops The apparatus of one or more preceding paragraphs can also include any combination of the following features described in this paragraph, among others described herein. The wound contact layer can further support a plurality of conductive tracks electrically connecting the plurality of sensors. At least some of the conductive tracks can be configured to be electrically connected to the controller. The circuit board can include multiple layers, and at least some of the multiple layers of the multilayered circuit board support the antenna. The circuit board can include one or more vias configured to interconnect the antenna on each of the multiple layers.

The apparatus of one or more preceding paragraphs can also include any combination of the following features described in this paragraph, among others described herein. The antenna can be configured as a near-field antenna. The antenna can positioned within a region of the controller defined by an external rectangle of 50×27 mm and an internal rectangle of 35×13 mm, where the internal rectangle is centered in the external rectangle. The antenna can include 3 mm corner radii. The antenna can be located within a region of the controller defined by an external circle with diameter 41 mm and an internal circle with diameter 24 mm, where the internal circle is concentric with the external circle. The antenna can include copper wire, etched or printed antenna material.

Other Variations

In some embodiments, one or more sensors can be positioned in or on a layer or layers of a wound dressing or another structure that is not in direct contact with a wound. In such cases, the sensors can measure one or more of impedance, temperature, color, pressure, or the like associated with the wound and/or periwound. For example, one or more sensors can be positioned above a dressing layer that transports or absorbs wound exudate. In this example, the one or more sensors can measure one or more of impedance, temperature, color, or the like of the wound exudate. These measurements can be used to determine status of the wound, which (as described herein) can include healing of the wound or non-healing of the wound.

In some embodiments, one or more electronic components can be positioned on the side of a wound contact layer opposite the side that faces the wound. Systems and methods described herein are equally applicable to such arrangements. Any wound dressing embodiment described herein can include features of any of the other described wound dressing embodiments. Similarly, any controller described herein can include features of any of the other described wound dressing embodiments. Further, any device, component, or module described in a certain embodiment can include features of any of the other described embodiments of the device, component, or module.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A method of operating a wound monitoring and/or therapy apparatus comprising a wound dressing including a substantially stretchable substrate supporting a plurality of sensors configured to obtain measurements of at least one of a wound or periwound and a plurality of conductive tracks electrically connecting the plurality of sensors, the method comprising:
    with a monitoring circuit of the apparatus, measuring a first change in resistance of at least one calibration track positioned on the substrate, the first change in resistance of the at least one calibration track corresponding to a change in resistance of at least some of the plurality of conductive tracks.

2. The method of claim 1, wherein the at least one calibration track surrounds at least a portion of a perimeter of the substrate.

3. The method of claim 1, further comprising measuring a baseline resistance of the at least one calibration track when an intact substrate is not stretched and determining the first change in resistance of the at least one calibration track based on a difference between the baseline resistance and resistance of the at least one calibration track due to stretching and/or tearing of the substrate.

4. The method of claim 3, further comprising adjusting a measurement obtained by a sensor of the plurality of sensors based on the first change in resistance.

5. The method of claim 1, further comprising, by a controller of the apparatus:
    receiving the first change in resistance from the monitoring circuit;
    determining that the first change in resistance exceeds a threshold; and
    controlling at least some of the plurality of sensors to defer obtaining one or more measurements.

6. The method of claim 5, further comprising, by the controller:
    determining that a second change in resistance measured subsequent to the measurement of the first change in resistance is below the threshold; and controlling the at least some of the plurality of sensors to obtain one or more measurements.

7. The method of claim 5, wherein the at least one calibration track comprises a plurality of calibration tracks, and wherein each of the calibration tracks is associated with a particular sensor of the plurality of sensors or wherein the plurality of calibration tracks is configured to measure a plurality of first changes in resistance associated with a plurality of different regions of the substrate.

8. The method of claim 5, wherein the at least some of the plurality of sensors comprise one or more sensors configured to measure impedance.

9. A wound monitoring and/or therapy apparatus comprising:
- a wound dressing configured to be positioned in contact with a wound, the wound dressing comprising a substantially stretchable substrate supporting a plurality of sensors configured to obtain measurements of at least one of the wound or periwound and a plurality of conductive tracks electrically connecting the plurality of sensors; and
- at least one calibration track positioned on the substrate, the at least one calibration track electrically connected to a monitoring circuit configured to measure a first change in resistance of the at least one calibration track, the first change in resistance of the at least one calibration track corresponding to a change in resistance of at least some of the plurality of conductive tracks.

10. The apparatus of claim 9, wherein the at least one calibration track surrounds at least a portion of a perimeter of the substrate.

11. The apparatus of claim 9, wherein the at least one calibration track comprises a plurality of calibration tracks, and wherein each of the calibration tracks is associated with a particular sensor of the plurality of sensors or wherein the plurality of calibration tracks is configured to measure a plurality of first changes in resistance associated with a plurality of different regions of the substrate.

12. The apparatus of claim 9, wherein the monitoring circuit is further configured to measure a baseline resistance of the at least one calibration track when an intact substrate is not stretched and determine the first change in resistance of the at least one calibration track based on a difference between the baseline resistance and resistance of the at least one calibration track due to stretching and/or tearing of the substrate.

13. The apparatus of claim 12, wherein the monitoring circuit is further configured to adjust a measurement obtained by a sensor of the plurality of sensors based on the first change in resistance.

14. The apparatus of claim 9, further comprising a controller configured to, in response to a determination that the first change in resistance exceeds a threshold, control at least some of the plurality of sensors to defer the measurement of the first change in resistance.

15. The apparatus of claim 14, wherein the controller is further configured to control the at least some of the plurality of sensors to obtain one or more measurements in response to a determination that a second change in resistance is below the threshold, the second change in resistance measured subsequent to the measurement of the first change in resistance.

16. The apparatus of claim 14, wherein the at least some of the plurality of sensors comprise one or more sensors configured to measure impedance.

17. The apparatus of claim 9, wherein the at least one calibration track is connected to a different power supply than the plurality of sensors.

\* \* \* \* \*